United States Patent

Kurihara et al.

[11] Patent Number: 6,077,840
[45] Date of Patent: Jun. 20, 2000

[54] TETRAHYDROBENZINDOLONE DERIVATIVES

[75] Inventors: Kenichi Kurihara; Rie Shinei; Yasushi Kurata; Yuji Tabata; Kiyoshi Tanabe; Tsuneo Okonogi, all of Yokohama, Japan

[73] Assignee: Meiji Seika Kaisha, Ltd., Tokyo-to, Japan

[21] Appl. No.: 09/331,294

[22] PCT Filed: Dec. 18, 1997

[86] PCT No.: PCT/JP97/04683

§ 371 Date: Jun. 18, 1999

§ 102(e) Date: Jun. 18, 1999

[87] PCT Pub. No.: WO98/27059

PCT Pub. Date: Jun. 25, 1998

[30] Foreign Application Priority Data

Dec. 18, 1996 [JP] Japan .................................. 8-338280
Nov. 11, 1997 [JP] Japan .................................. 9-308891

[51] Int. Cl.[7] .................. A61K 31/535; A61K 31/40; A61K 31/44; A61K 31/50; C07D 233/02

[52] U.S. Cl. .................. 514/232.8; 514/411; 514/339; 514/323; 514/253; 548/311.4; 548/450; 546/276.7; 546/200; 544/372; 544/142

[58] Field of Search .................. 548/450, 311.4, 514/411, 339, 323, 253, 232.8; 546/276.7, 200, 142; 544/372, 142

[56] References Cited

U.S. PATENT DOCUMENTS 4,014,899 3/1977 Bowman et al. .................. 260/326.1

FOREIGN PATENT DOCUMENTS 7-215935 8/1995 Japan .
8-277253 10/1996 Japan .

*Primary Examiner*—Zinna Northington Davis
*Assistant Examiner*—Binta Robinson
*Attorney, Agent, or Firm*—Wenderoth, Lind & Ponack, L.L.P.

[57] ABSTRACT

Compounds represented by the following formula (I) or pharmaceutically acceptable salts thereof and a process for producing the same are disclosed. The compounds have progesterone receptor binding inhibitory activity and, hence, can be used as therapeutic and prophylactic agents for progesterone-related diseases. Specifically, they are useful as carcinostatic agents for breast cancer and ovarian cancer, therapeutic agents for hysteromyoma, endometriosis, meningioma, and myeloma, abortifacients, oral contraceptive pills, and therapeutic and prophylactic agents for osteoporosis and climacteric disturbance.

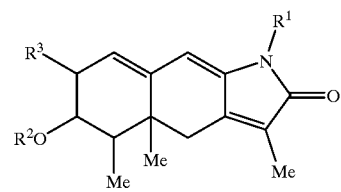

(I)

wherein $R^1$ represents alkyl or aralkyl; $R^2$ represents a hydrogen atom, alkylcarbonyl, cycloalkylcarbonyl, aromatic acyl, heteroaromatic acyl, saturated heterocyclic acyl, alkyl, alkenyl, aralkyl, carbamoyl, alkylcarbamoyl, aromatic carbamoyl, aralkylcarbamoyl, alkylaminocarbonyl, cycloalkylcarbamoyl, alkoxycarbonyl, aryloxycarbonyl, heteroaromatic thiocarbonyl, saturated heterocyclic thiocarbonyl, or alkyl-thiocarbamoyl: and $R^3$ represents a hydrogen atom, a hydroxyl group, alkyloxy, alkylcarbonyloxy, alkylthio, or arylthio.

10 Claims, 1 Drawing Sheet

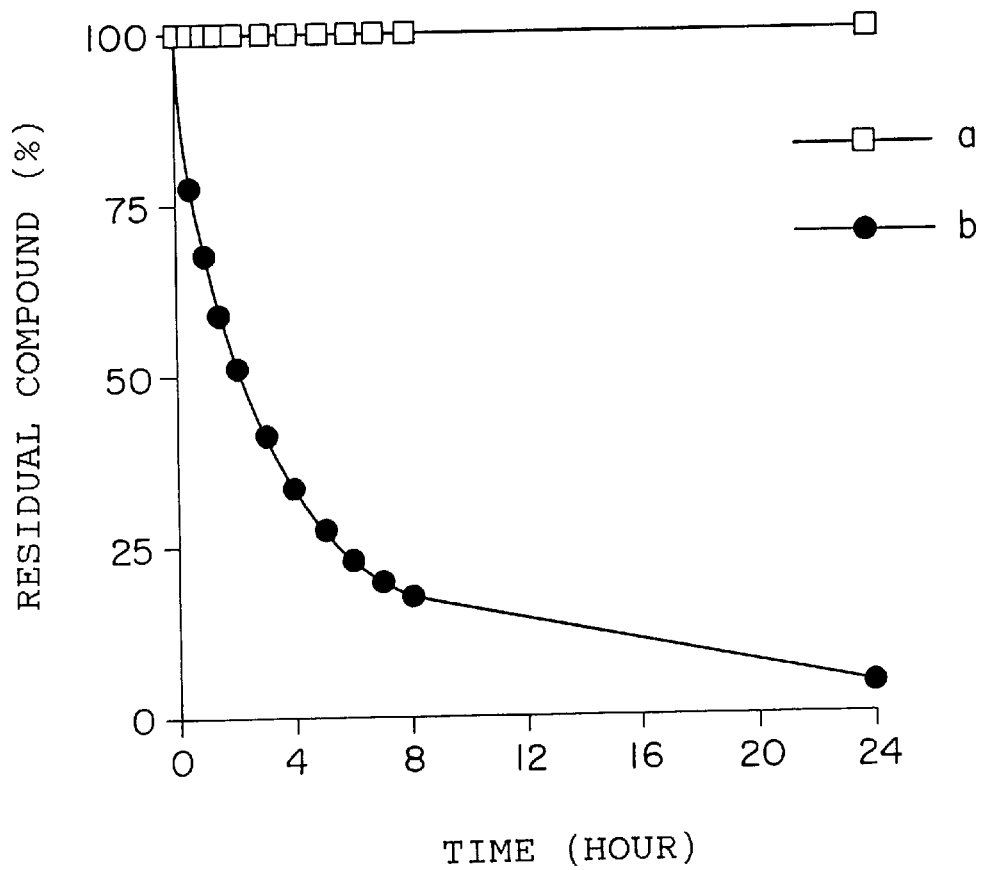
F I G. 1

TETRAHYDROBENZINDOLONE DERIVATIVES

This application is a 371 of PCT/JP97/04683 filed Dec. 18, 1997.

BACKGROUND OF THE INVENTION

1. Field of Invention

The present invention relates to compounds as a progesterone receptor binding inhibotor and pharmaceutical compositions containing the same.

2. Background Art

In recent years, even in Japan, the number of patients suffering from breast cancer has increased, and it is foreseen that the number of the patients suffering from breast cancer would become largest among the malignant tumors in women in the 21st century. Ovariectomy has for the first time been used as endocrinotherapy for breast cancer. Thereafter, adrenalectomy and hypophysectomy have been reported to be useful as therapy for breast cancer in progress, and, since then, surgical endocrinotherapy has been mainly used and made progress. In the surgical endocrinotherapy, an organ involved in the secretion of estrogen is removed to regress estrogen dependent breast cancer. This, however, results in loss of not only estrogen but also life-sustaining hormones, including steroid hormones, posing many problems associated with the quality of life.

Non-steroidal anti-estrogen agents typified by Tamoxifen Citrate which appeared in the latter half of 1970s have extensively used clinically by virtue of high effect against breast cancer and much lower side effect than conventional androgen and estrogen. Then, they have replaced the surgical endocrinotherapy used as main therapy for breast cancer.

More recently, agents having a new mechanism of action, such as medroxyprogesterone acetate (MPA) ("NYUGAN NO RINSHO", vol. 1, 201–213 (1986)), aromatase inhibitor, luteinizing hormone-releasing hormone (LH-RH) agonist ("GAN TO KAGAKU RYOHO", 16, 2729 (1994)) have been developed, resulting in diversified endocrinotherapy for breast cancer.

Further, in recent years, the treatment of breast cancer with an antiprogesterone agent based on progesterone receptor has been actively attempted. For example, Mifepristone (RU38486) (Cancer Res.), 49, 2851–2856, 1989, Onapristone (ZK98299) (J. Steroid Biochem. Molecu. Biol., 41, 339–348, 1992) and the like are under development. These novel types of agents as a progesterone receptor binding inhibotor are expected to be useful for the treatment of not only breast cancer but also for endometriosis, hysteromyoma, meningioma and the like. Further, side effects, attributable to weak estrogenagonist action which are developed by prolonged administration of Tamoxifen Citrate, such as endometrioma, thrombosis, and hepatoma, and, in addition, cancer resistant to Tamoxifen Citrate, have been reported as a new problem. Since antiprogesterone agents are different from Tamoxifen Citrate in mechanism of action, they are expected as novel therapeutic agents which can avoid the above problems.

However, all of them have a steroidal skeleton. Thus, they have been pointed out to have side effect characteristic of steroid. Therefore, in order to overcome these problems, an agent having progesterone receptor binding inhibitory activity without the steroid skeleton has been desired in the art.

Some of the present inventors have previously succeeded in isolation of substance PF1092, which, despite a non-steroid skeleton, is a inhibitor against binding of progesterone to progesterone receptor, from a cultured mixture of a strain belonging to the genus Penicillium (Japanese Patent Laid-Open No. 253467/1996 and EP722940A, which are incorporated herein by reference).

The substance PF1092 is a ligularenolide type sesquiterpene having in its molecule an enol lactone ring structure. Many sesquiterpenes each having in its molecule an oxygen atom derived from a lactone ring structure or a furan ring structure are known in the art.

To the best of the present inventors' knowledge, no ligularenolide type skeleton containing a hetero atom, other than an oxygen atom, independently of natural and non-natural types are known in the art.

SUMMARY OF THE INVENTION

The present inventors have conducted the synthesis of a novel compound, having a ligularenolide type skeleton, analogous to PF1092 and the confirmation of the activity thereof. As a result, they have found that these compounds have highly selective progesterone receptor binding inhibitory activity and better stability than compounds having a ligularenolide skeleton. The present invention has been made based on such finding.

Accordingly, an object of the present invention is to provide novel compounds which have a ligularenolide skeleton as highly selective progesterone receptor binding inhibitor.

Another object of the present invention is to provide therapeutic and prophylactic agents for progesterone-related diseases.

A further object of the present invention is to provide intermediates which may be preferably used for the synthesis of the novel compounds.

Thus, according to one aspect of the present invention, there is provided a compound represented by the following formula (I) or a pharmaceutically acceptable salt thereof:

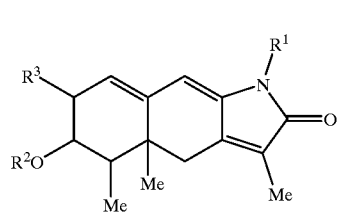

(I)

wherein
R$^1$ represents
  a hydrogen atom,
  optionally substituted $C_1$–$C_{10}$ alkyl,
  optionally substituted $C_2$–$C_{10}$ alkenyl,
  optionally substituted $C_2$–$C_{10}$ alkynyl,
  optionally substituted $C_3$–$C_{10}$ cycloalkyl, or
  optionally substituted $C_7$–$C_{15}$ aralkyl;
R$^2$ represents
  a hydrogen atom,
  optionally substituted $C_1$–$C_{10}$ alkylcarbonyl,
  optionally substituted $C_2$–$C_{10}$ alkenylcarbonyl,
  optionally substituted $C_2$–$C_{10}$ alkynylcarbonyl,
  optionally substituted $C_3$–$C_{15}$ cycloalkylcarbonyl,
  optionally substituted $C_7$–$C_{15}$ aralkylcarbonyl,
  optionally substituted $C_7$–$C_{15}$ aromatic acyl,
  optionally substituted $C_2$–$C_{15}$ heteroaromatic acyl having at least one hetero atom selected from the group consisting of nitrogen, oxygen, and sulfur atoms, optionally substituted $C_3$–$C_{15}$ saturated heterocyclic acyl having at least one hetero atom selected from the group consisting of nitrogen, oxygen, and sulfur atoms, optionally substituted $C_1$–$C_{10}$ alkyl, optionally substituted $C_2$–$C_{10}$ alkenyl, optionally substituted $C_2$–$C_{10}$ alkynyl, optionally substituted $C_3$–$C_{10}$ cycloalkyl, optionally substituted $C_7$–$C_{15}$ aralkyl, carbamoyl, optionally substituted N-$C_1$–$C_{10}$ alkylcarbamoyl, optionally substituted N-$C_6$–$C_{15}$ aromatic carbamoyl, optionally substituted N-$C_7$–$C_{15}$ aralkylcarbamoyl, optionally substituted N,N-di-$C_1$–$C_{10}$ alkylaminocarbonyl, optionally substituted N-$C_3$–$C_{10}$ cycloalkylcarbamoyl, optionally substituted $C_1$–$C_{10}$ alkoxycarbonyl, optionally substituted $C_6$–$C_{15}$ aryloxycarbonyl, optionally substituted $C_7$–$C_{15}$ aralkyloxycarbonyl, optionally substituted $C_1$–$C_{15}$ heteroaromatic thiocarbonyl having at least one hetero atom selected from the group consisting of nitrogen, oxygen, and sulfur atoms, optionally substituted $C_2$–$C_{15}$ saturated heterocyclic thiocarbonyl having at least one hetero atom selected from the group consisting of nitrogen, oxygen, and sulfur atoms, or optionally substituted N-$C_1$–$C_{10}$ alkyl-thiocarbamoyl; and $R^3$ represents a hydrogen atom, a hydroxyl group, optionally substituted $C_1$–$C_{10}$ alkyloxy, optionally substituted $C_2$–$C_{10}$ alkenyloxy, optionally substituted $C_2$–$C_{10}$ alkynyloxy, optionally substituted $C_3$–$C_{10}$ cycloalkyloxy, optionally substituted $C_7$–$C_{15}$ aralkyloxy, optionally substituted $C_1$–$C_{10}$ alkylcarbonyloxy, optionally substituted $C_2$–$C_{10}$ alkenylcarbonyloxy, optionally substituted $C_2$–$C_{10}$ alkynylcarbonyloxy, optionally substituted $C_3$–$C_{10}$ cycloalkylcarbonyloxy, optionally substituted $C_7$–$C_{15}$ aromatic acyloxy, optionally substituted $C_7$–$C_{15}$ aralkylcarbonyloxy, optionally substituted $C_1$–$C_{10}$ alkylthio, optionally substituted $C_2$–$C_{10}$ alkenylthio, optionally substituted $C_2$–$C_{10}$ alkynylthio, optionally substituted $C_3$–$C_{10}$ cycloalkylthio, optionally substituted $C_6$–$C_{15}$ arylthio, or optionally substituted $C_7$–$C_{15}$ aralkylthio.

According to another aspect of the present invention, there is provided a pharmaceutical composition, useful as a therapeutic or prophylactic agent for progesterone-related diseases, as an abortifacient, or as a contraceptive, comprising the compound as an active ingredient.

According to a further aspect of the present invention, there is provided a compound, useful as an intermediate for the synthesis of the compound represented by formula (I), represented by the following formula (II) or a pharmaceutically acceptable salt thereof:

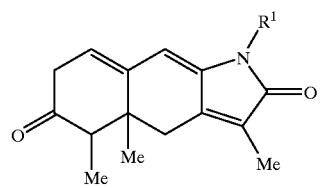

wherein $R^1$ represents a hydrogen atom, optionally substituted $C_1$–$C_{10}$ alkyl, optionally substituted $C_2$–$C_{10}$ alkenyl, optionally substituted $C_2$–$C_{10}$ alkynyl, optionally substituted $C_3$–$C_{10}$ cycloalkyl, or optionally substituted $C_7$–$C_{15}$ aralkyl.

BRIEF DESCRIPTION OF THE DRAWINGS

The FIGURE is a diagram showing the results of a test on the chemical stability of the compound according to the present invention, wherein compound (a) is the compound prepared in Example 24 and compound (b) is 3β-hydroxy-2α-methoxy-1(10),7(11),8-eremophilatrien-12,8-olide which is a compound provided by replacing the nitrogen atom in the compound (a) with an oxygen atom. In this test, an aqueous NaOH solution was added to methanol solutions of these respective compounds, and the amount of the compounds remaining undecomposed was measured with the elapse of time.

DETAILED DESCRIPTION OF THE INVENTION

Definition

As used herein, the terms "alkyl," "alkenyl," and "alkynyl" as a group or a part of a group respectively mean straight or branched chain alkyl, alkenyl, and alkynyl. The term "halogen atom" used herein means a fluorine, chlorine, bromine, or iodine atom. The term "aralkyl" used herein means benzyl, phenylethyl (phenethyl), methylbenzyl, naphthylmethyl or the like. The term "acyl" used herein means alkylcarbonyl, alkenylcarbonyl, alkynylcarbonyl, aralkylcarbonyl, cycloalkylcarbonyl, aromatic acyl, heteroaromatic acyl, or saturated heterocyclic acyl. The term "aryl" preferably means phenyl, naphthyl, tolyl or the like.

Compounds Represented by Formula (I)

In the formula (I), the $C_1$–$C_{10}$ alkyl represented by $R^1$ and $R^2$ is preferably $C_1$–$C_6$ alkyl, more preferably $C_1$–$C_5$ alkyl.

At least one hydrogen atom on the alkyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl. The $C_1$–$C_6$ alkyl in the optional substituent described-above and described-below represented by $R^1$, $R^2$, and $R^3$ is preferably $C_1$–$C_4$ alkyl.

The $C_2$–$C_{10}$ alkenyl represented by $R^1$ and $R^2$ is preferably $C_2$–$C_6$ alkenyl, more preferably $C_2$–$C_4$ alkenyl.

At least one hydrogen atom on the alkenyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkynyl represented by $R^1$ and R is preferably $C_2$–$C_6$ alkynyl, more preferably $C_2$–$C_4$ alkynyl.

At least one hydrogen atom on the alkynyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{10}$ cycloalkyl represented by $R^1$ and $R^2$ is preferably $C_3$–$C_7$ cycloalkyl, and examples thereof include cyclopropyl, cyclobutyl, cyclopentyl, and cyclohexyl.

At least one hydrogen atom on the cycloalkyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aralkyl represented by $R^1$ and $R^2$ include benzyl, phenylethyl, methylbenzyl, and naphthylmethyl.

At least one hydrogen atom on the aralkyl (preferably a hydrogen atom on the ring) may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_1$–$C_{10}$ alkylcarbonyl represented by $R^2$ is preferably $C_1$–$C_6$ alkylcarbonyl, more preferably $C_1$–$C_4$ alkylcarbonyl.

At least one hydrogen atom on the alkylcarbonyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkenylcarbonyl represented by $R^2$ is preferably $C_2$–$C_6$ alkenylcarbonyl, more preferably $C_2$–$C_4$ alkenylcarbonyl.

At least one hydrogen atom on the alkenylcarbonyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkynylcarbonyl represented by $R^2$ is preferably $C_2$–$C_6$ alkynylcarbonyl, more preferably $C_2$–$C_4$ alkynylcarbonyl.

At least one hydrogen atom on the alkynylcarbonyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{10}$ cycloalkylcarbonyl represented by $R^2$ is preferably $C_3$–$C_7$ cycloalkylcarbonyl, and examples thereof include cyclopropylcarbonyl, cyclobutylcarbonyl, cyclopentylcarbonyl, and cyclohexylcarbonyl.

At least one hydrogen atom on the cycloalkylcarbonyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_6$–$C_{15}$ aromatic acyl represented by $R^2$ include benzoyl, toluoyl, and naphthoyl.

At least one hydrogen atom on the aromatic acyl may be substituted, and examples of substituents usable herein include $C_1$–$C_6$ alkyl, a halogen atom (a chlorine, bromine, or iodine atom), nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aralkylcarbonyl represented by $R^2$ include benzylcarbonyl, phenylethylcarbonyl, methylbenzylcarbonyl, and naphthylmethylcarbonyl.

At least one hydrogen atom on the aralkylcarbonyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_2$–$C_{15}$ heteroaromatic acyl, having at least one hetero atom selected from the group consisting of nitrogen, oxygen, and sulfur atoms, represented by $R^2$ is preferably a five- or six-membered heteroaromatic acyl having one or two nitrogen, oxygen, or sulfur atoms (for example, furoyl, pyranylcarbonyl, thenoyl, or imidazolylcarbonyl), or a five- or six-membered heteroaromatic acyl containing a nitrogen atom and a sulfur atom (for example, thiazolylcarbonyl). The heteroaromatic ring of the heteroaromatic acyl may be condensed with other ring, for example, a benzene ring, and examples of the heteroaromatic ring condensed with other ring include benzothiophene.

At least one hydrogen atom on the heteroaromatic acyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{15}$ saturated heterocyclic acyl, having at least one hetero atom selected from the group consisting of nitrogen, oxygen, and sulfur atoms, represented by $R^2$ is preferably a five- or six-membered heterocyclic acyl containing one oxygen or sulfur atom (for example, pyrrolidinylcarbonyl, piperidinylcarbonyl, piperazinylcarbonyl, or morpholinylcarbonyl).

At least one hydrogen atom on the saturated heterocyclic acyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The carbamoyl represented by $R^2$ is N,N-dihydrocarbamoyl having no substituent.

The N-$C_1$–$C_{10}$ alkylcarbamoyl represented by $R^2$ is preferably N-$C_1$–$C_6$ alkylcarbamoyl, more preferably N-$C_1$–$C_4$ alkylcarbamoyl.

At least one hydrogen atom on the alkylcarbamoyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The N,N-di-$C_1$–$C_{10}$ alkylaminocarbonyl represented by $R^2$ is preferably N,N-di-$C_1$–$C_6$ alkylaminocarbonyl, more preferably N,N-di-$C_1$–$C_4$ alkylaminocarbonyl.

The N-$C_3$–$C_{10}$ cycloalkylcarbamoyl represented by $R^2$ is preferably N-$C_3$–$C_7$ cycloalkylcarbamoyl, and examples thereof include N-cyclopropylcarbamoyl, N-cyclobutylcarbamoyl, N-cyclopentylcarbamoyl, and N-cyclohexylcarbamoyl.

At least one hydrogen atom on the N-cycloalkylcarbamoyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the N-$C_6$–$C_{15}$ aromatic carbamoyl represented by $R^2$ include N-phenylcarbamoyl, N-toluylcarbamoyl, and N-naphthylcarbamoyl.

At least one hydrogen atom on the N-aromatic carbamoyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the N-$C_7$–$C_{15}$ aralkylcarbamoyl represented by $R^2$ include N-benzylcarbamoyl, N-phenylethylcarbamoyl, N-methylbenzylcarbamoyl, and N-naphthylmethylcarbamoyl.

At least one hydrogen atom on the N-aralkylcarbamoyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_1$–$C_{10}$ alkoxycarbonyl represented by $R^2$ is preferably $C_1$–$C_6$ alkoxycarbonyl, more preferably $C_1$–$C_4$ alkoxycarbonyl.

At least one hydrogen atom on the alkoxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aryloxycarbonyl represented by $R_2$ include phenyloxycarbonyl, toluyloxycarbonyl, and naphthyloxycarbonyl.

At least one hydrogen atom on the aryloxycarbonyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_8$–$C_{15}$ aralkyloxycarbonyl represented by $R^2$ include benzyloxycarbonyl, phenylethyloxycarbonyl, methylbenzyloxycarbonyl, and naphthylmethyloxycarbonyl.

At least one hydrogen atom on the aralkyloxycarbonyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_1$–$C_{15}$ heteroaromatic thiocarbonyl, having at least one hetero atom selected from the group consisting of nitrogen, oxygen, and sulfur atoms, represented by $R^2$ is preferably a five-membered or six-membered heteroaromatic thiocarbonyl having one oxygen or sulfur atom (for example, imidazolylthiocarbonyl).

At least one hydrogen atom on the heteroaromatic thiocarbonyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{15}$ saturated heterocyclic thiocarbonyl, having at least one hetero atom selected from the group consisting of nitrogen, oxygen, and sulfur atoms, represented by $R^2$ is preferably a five-membered or six-membered saturated heterocyclic thiocarbonyl having one oxygen or sulfur atom (for example, pyrrolidyl-thiocarbonyl, piperidyl-thiocarbonyl, piperazyl-thiocarbonyl, morpholyl-thiocarbonyl).

At least one hydrogen atom on the saturated heterocyclic thiocarbonyl may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_1$–$C_{10}$ alkyl-thiocarbamoyl represented by $R^2$ is preferably $C_1$–$C_6$ alkyl-thiocarbamoyl, more preferably N-$C_1$–$C_4$ alkyl-thiocarbamoyl.

At least one hydrogen atom on the alkyl-thiocarbamoyl may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_1$–$C_{10}$ alkyloxy represented by $R^3$ is preferably $C_1$–$C_6$ alkyloxy, more preferably $C_1$–$C_4$ alkyloxy.

At least one hydrogen atom on the alkyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkenyloxy represented by $R^3$ is preferably $C_2$–$C_6$ alkenyloxy, more preferably $C_2$–$C_4$ alkenyloxy.

At least one hydrogen atom on the alkenyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkynyloxy represented by $R^3$ is preferably $C_2$–$C_6$ alkynyloxy, more preferably $C_2$–$C_4$ alkynyloxy.

At least one hydrogen atom on the alkynyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{10}$ cycloalkyloxy represented by $R^3$ is preferably $C_3$–$C_7$ cycloalkyloxy, and examples thereof include cyclopropyloxy, cyclobutyloxy, cyclopentyloxy, and cyclohexyloxy.

At least one hydrogen atom on the cycloalkyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aralkyloxy represented by $R^3$ is preferably benzyloxy, phenylethoxy, methylbenzyloxy, and naphthylmethoxy.

At least one hydrogen atom on the aralkyloxy may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_1$–$C_{10}$ alkylcarbonyloxy represented by $R^3$ is preferably $C_1$–$C_6$ alkylcarbonyloxy, more preferably $C_1$–$C_4$ alkylcarbonyloxy.

At least one hydrogen atom on the alkylcarbonyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkenylcarbonyloxy represented by $R^3$ is preferably $C_2$–$C_6$ alkenylcarbonyloxy, more preferably $C_2$–$C_4$ alkenylcarbonyloxy.

At least one hydrogen atom on the alkenylcarbonyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkynylcarbonyloxy represented by $R^3$ is preferably $C_2$–$C_6$ alkynylcarbonyloxy, more preferably $C_2$–$C_4$ alkynylcarbonyloxy.

At least one hydrogen atom on the alkynylcarbonyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{10}$ cycloalkylcarbonyloxy represented by $R^3$ is preferably $C_3$–$C_{10}$ cycloalkylcarbonyloxy, and examples thereof include cyclopropylcarbonyloxy, cyclobutylcarbonyloxy, cyclopentylcarbonyloxy, and cyclohexylcarbonyloxy.

At least one hydrogen atom on the cycloalkylcarbonyloxy may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aromatic acyloxy represented by $R^3$ include benzoyloxy, toluoyloxy, and naphthoyloxy.

At least one hydrogen atom on the aromatic acyloxy may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aralkylcarbonyloxy represented by $R^3$ include benzylcarbonyloxy, phenylethylcarbonyloxy, methylbenzylcarbonyloxy, and naphthylmethylcarbonyloxy.

At least one hydrogen atom on the aralkylcarbonyloxy may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

The $C_1$–$C_{10}$ alkylthio represented by $R^3$ is preferably $C_1$–$C_6$ alkylthio, more preferably $C_1$–$C_4$ alkylthio.

At least one hydrogen atom on the alkylthio may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkenylthio represented by $R^3$ is preferably $C_2$–$C_6$ alkenylthio, more preferably $C_2$–$C_4$ alkenylthio.

At least one hydrogen atom on the alkenylthio may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_2$–$C_{10}$ alkynylthio represented by $R^3$ is preferably $C_2$–$C_6$ alkynylthio, more preferably $C_2$–$C_4$ alkynylthio.

At least one hydrogen atom on the alkynylthio may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, $C_3$–$C_{10}$ cycloalkyl (preferably $C_3$–$C_7$ cycloalkyl, for example, cyclopropyl), oxiranyl, 2-propenyl, and hydroxyiminomethyl.

The $C_3$–$C_{10}$ cycloalkylthio represented by $R^3$ is preferably $C_3$–$C_7$ cycloalkylthio, and examples thereof include cyclopropylthio, cyclobutylthio, cyclopentylthio, and cyclohexylthio.

At least one hydrogen atom on the cycloalkylthio may be substituted, and examples of substituents usable herein include a halogen atom, nitro, amino, $C_1$–$C_6$ alkyl disubstituted (for example, dimethyl-substituted) amino, carboxyl, $C_1$–$C_6$ alkoxy (for example, methoxy), $C_1$–$C_6$ alkoxy-substituted $C_1$–$C_6$ alkoxy, a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_6$–$C_{15}$ arylthio represented by $R^3$ include phenylthio, toluylthio, and naphthylthio.

At least one hydrogen atom on the arylthio may be substituted, and examples of substituents usable herein include $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, $C_1$–$C_6$ alkylsulfonyl (for example, methylsulfonyl), cyano, phenyl, and $C_3$–$C_{10}$ cycloalkyl (preferably $C_3$–$C_7$ cycloalkyl, for example, cyclopropyl), oxiranyl, 2-propenyl, and hydroxyiminomethyl.

Examples of the $C_7$–$C_{15}$ aralkylthio represented by $R^3$ include benzylthio, phenylethylthio, methylbenzylthio, and naphthylthio.

At least one hydrogen atom on the aralkylthio may be substituted, and substituents usable herein include, for example, $C_1$–$C_6$ alkyl, a halogen atom, nitro, amino, $C_1$–$C_6$ alkyl disubstituted (for example, dimethyl-substituted) amino, carboxyl, $C_1$–$C_6$ alkoxy (for example, methoxy), a hydroxyl group, sulfoxyl, $C_1$–$C_6$ alkylthio (for example, methylthio), mercapto, cyano, phenyl, and $C_3$–$C_{10}$ cycloalkyl (preferably $C_3$–$C_7$ cycloalkyl, for example, cyclopropyl).

Among the compounds represented by the formula (I) according to the present invention, a group of preferred compounds include those represented by the formula (I) wherein $R^1$ represents
  optionally substituted $C_1$–$C_{10}$ alkyl or
  optionally substituted $C_7$–$C_{15}$ aralkyl;
$R^2$ represents
  a hydrogen atom,
  optionally substituted $C_1$–$C_{10}$ alkylcarbonyl,
  optionally substituted $C_3$–$C_{10}$ cycloalkylcarbonyl,
  optionally substituted $C_7$–$C_{15}$ aromatic acyl,
  optionally substituted $C_2$–$C_{15}$ heteroaromatic acyl having at least one hetero atom selected from the group consisting of nitrogen, oxygen, and sulfur atoms,
  optionally substituted $C_3$–$C_{15}$ saturated heterocyclic acyl having at least one hetero atom selected from the group consisting of nitrogen, oxygen, and sulfur atoms,
  optionally substituted $C_1$–$C_{10}$ alkyl,
  optionally substituted $C_2$–$C_{10}$ alkenyl,
  optionally substituted $C_7$–$C_{15}$ aralkyl,
  carbamoyl,
  optionally substituted N-$C_1$–$C_{10}$ alkylcarbamoyl,
  optionally substituted N-$C_6$–$C_{15}$ aromatic carbamoyl,
  optionally substituted N-$C_7$–$C_{15}$ aralkylcarbamoyl,
  optionally substituted N,N-di-$C_1$–$C_{10}$ alkylaminocarbonyl,
  optionally substituted N-$C_3$–$C_{10}$ cycloalkylcarbamoyl,
  optionally substituted $C_1$–$C_{10}$ alkoxycarbonyl,
  optionally substituted $C_6$–$C_{15}$ aryloxycarbonyl,
  optionally substituted $C_1$–$C_{15}$ heteroaromatic thiocarbonyl having at least one hetero atom selected from the group consisting of nitrogen, oxygen, and sulfur atoms,
  optionally substituted $C_2$–$C_{15}$ saturated heterocyclic thiocarbonyl having at least one hetero atom selected from the group consisting of nitrogen, oxygen, and sulfur atoms, or
  optionally substituted N-$C_1$–$C_{10}$ alkyl-thiocarbamoyl; and
$R^3$ represents
  a hydrogen atom,
  a hydroxyl group,
  optionally substituted $C_1$–$C_{10}$ alkyloxy,
  optionally substituted $C_1$–$C_{10}$ alkylcarbonyloxy,
  optionally substituted $C_1$–$C_{10}$ alkylthio, or
  optionally substituted $C_6$–$C_{15}$ arylthio.

Among the above group of preferred compounds, a group of more preferred compounds include those represented by the formula (I) wherein
$R^1$ represents
  $C_1$–$C_{10}$ alkyl or
  $C_7$–$C_{15}$ aralkyl optionally substituted by $C_1$–$C_6$ alkoxy;
$R^2$ represents
  a hydrogen atom,
  $C_1$–$C_{10}$ alkylcarbonyl,
  $C_3$–$C_{15}$ cycloalkylcarbonyl,
  $C_6$–$C_{15}$ aromatic acyl optionally substituted by $C_1$–$C_6$ alkoxy or nitro,
  $C_2$–$C_{15}$ heteroaromatic acyl having at least one hetero atom selected from the group consisting of nitrogen, oxygen, and sulfur atoms,
  $C_3$–$C_{15}$ saturated heterocyclic acyl, having at least one hetero atom selected from the group consisting of nitrogen, oxygen, and sulfur atoms, optionally substituted by $C_1$–$C_6$ alkyl or $C_1$–$C_6$ alkoxy-$C_1$–$C_6$ alkyl,
  $C_1$–$C_{10}$ alkyl optionally substituted by $C_3$–$C_7$ cycloalkyl or hydroxyl,
  $C_2$–$C_{10}$ alkenyl optionally substituted by phenyl,
  $C_7$–$C_{15}$ aralkyl optionally substituted by $C_1$–$C_6$ alkoxy, carbamoyl,
  N-$C_1$–$C_{10}$ alkylcarbamoyl in which hydrogen atom(s) on the alkyl is optionally substituted by a hydroxyl group,
  N-$C_6$–$C_{15}$ aromatic carbamoyl,
  N-$C_7$–$C_{15}$ aralkylcarbamoyl,
  N,N-di-$C_1$–$C_{10}$ alkylaminocarbonyl,
  N-$C_3$–$C_{10}$ cycloalkylcarbamoyl,
  $C_1$–$C_{10}$ alkoxycarbonyl,
  $C_6$–$C_{15}$ aryloxycarbonyl,
  $C_1$–$C_{15}$ heteroaromatic thiocarbonyl having at least one nitrogen atom,
  $C_2$–$C_{15}$ saturated heterocyclic thiocarbonyl having at least one nitrogen atom, or
  N-$C_1$–$C_{10}$ alkyl-thiocarbamoyl; and
$R^3$ represents
  a hydrogen atom,
  a hydroxyl group,
  $C_1$–$C_{10}$ alkyloxy optionally substituted by $C_3$–$C_{10}$ cycloalkyl,
  $C_1$–$C_{10}$ alkylcarbonyloxy,
  $C_1$–$C_{10}$ alkylthio, or
  $C_6$–$C_{15}$ arylthio.

Another group of preferred compounds include those represented by the formula (I) wherein
$R^1$ represents
  $C_1$–$C_6$ alkyl or
  benzyl optionally substitute by $C_1$–$C_6$ alkoxy;
$R^2$ represents
  a hydrogen atom,
  $C_1$–$C_6$ alkylcarbonyl,
  $C_3$–$C_7$ cycloalkylcarbonyl,
  benzoyl optionally substituted by $C_1$–$C_6$ alkoxy or nitro,
  five- or six-membered heteroaromatic acyl having one or two nitrogen, oxygen, or sulfur atoms,
  five- or six-membered heteroaromatic acyl having nitrogen and sulfur atoms,
  five- or six-membered saturated heterocyclic acyl having a oxygen or sulfur atom,
  $C_1$–$C_6$ alkyl optionally substituted by $C_3$–$C_7$ cycloalkyl or hydroxy,
  $C_2$–$C_6$ alkenyl optionally substituted by phenyl,
  benzyl optionally substituted by $C_1$–$C_6$ alkoxy, carbamoyl,
  N-$C_1$–$C_6$ alkylcarbamoyl in which hydrogen atom(s) on the alkyl is optionally substituted by a hydroxyl group,
  N-phenylcarbamoyl,
  N-benzylcarbamoyl,
  N,N-di-$C_1$–$C_6$ alkylaminocarbonyl,
  N-$C_3$–$C_7$ cycloalkylcarbamoyl,
  $C_1$–$C_6$ alkoxycarbonyl,
  phenyloxycarbonyl,
  pyrimidylthiocarbonyl,
  pyrrolidylthiocarbonyl, or
  N-$C_1$–$C_6$ alkyl-thiocarbamoyl; and
$R^3$ represents
  a hydrogen atom,
  a hydroxyl group,
  $C_1$–$C_6$ alkyloxy optionally substituted by $C_3$–$C_7$ cycloalkyl,
  $C_1$–$C_6$ alkylcarbonyloxy,
  $C_1$–$C_6$ alkylthio, or
  phenylthio.

Since the compounds represented by the formula (I) according to the present invention have several asymmetric carbons, various isomers attributable to these carbons are considered. The present invention embraces these individual isomers and mixtures thereof.

The compounds represented by the formula (I) may be present in the form of a salt. Examples of the salt include pharmacologically acceptable salts, and specific examples thereof include lithium, sodium, potassium, magnesium, and calcium salts; salts with ammonium and suitable non-toxic amines, for example, $C_1$–$C_6$ alkylamine (for example, triethylamine) salts, $C_1$–$C_6$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenethylamine, N,N-dibenzylethylenediamine, or dibenzylamine) salts, and heterocyclic amines (for example, morpholine or N-ethylpyridine) salts; salts of hydrohalogenic acids such as hydrofluoric acid, hydrochloric acid, hydrobromic acid and hydroiodic acid; inorganic acid salts such as sulfate, nitrate, phosphate, perchlorate and carbonate; salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of amino acids such as arginic acid, aspartic acid and glutamic acid; and salts of organic acids such as methanesulfonic acid and p-toluenesulfonic acid.

Use of Compounds Represented by Formula (I)/Pharmaceutical Compositions

The compounds, represented by the formula (I), according to the present invention have progesterone receptor binding inhibitory activity and, hence, can be used as therapeutic and prophylactic agents for progesterone-related diseases. The progesterone receptor has been reported to be expressed in breast, uterus, ovary, bone, and central nerve. Therefore, the compounds represented by the formula (I) are useful as therapeutic and prophylactic agents for progesterone-related diseases in these organs. More specifically, they are useful as carcinostatic agents for breast cancer and ovarian cancer, therapeutic agents for hysteromyoma, endometriosis, meningioma, and myeloma, abortifacients, oral contraceptive pills, and therapeutic and prophylactic agents for osteoporosis and climacteric disturbance. In particular, the compounds represented by the formula (I) according to the present invention have no steroid skeleton and, hence, are considered to be advantageously free from side effect inherent in steroid such as found in conventional progesterone receptor binding inhibitors having a steroid skeleton.

A pharmaceutical composition comprising as an active ingredient a compound of the present invention can be administered either orally or parenterally (e.g., intravenous injection, intramuscular injection, subcutaneous administration, rectal administration, percutaneous administration) to humans or animals other than humans.

The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill, fine subtilaes, or a troche for oral administration; a preparation for rectal administration; an oleaginous suppository; and an aqueous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include lactose, fructose, glucose, starch, gelatin, magnesium carbonate, synthetic magnesium silicate, talc, magnesium stearate, methyl cellulose, carboxymethyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention is properly determined in consideration of the symptom and the age and sex of a patient for each case. When the compound is intravenously administered as the above therapeutic or prophylactic agent, especially contraceptive, or therapeutic agent for breast cancer or ovarian cancer, approximately 0.01 to 1000 mg, preferably 0.1 to 100 mg, of the compound is generally administered per day for adult human, at one time or several times. On the other hand, for intramuscular administration, approximately 0.01 to 1000 mg, preferably 0.1 to 100 mg, of the compound is generally administered per day for adult human, at one time or several times. For oral administration, approximately 0.5 to 2000 mg, preferably 1 to 1000 mg, of the compound is generally administered per day for adult human, at one time or several times.

Preparation of Compounds Represented by Formula (I)

The compounds represented by the formula (I) according to the present invention can be prepared from substance PF1092C as a starting compound through the following processes. The substance PF1092C can be prepared, for example, by Steps (A) to (D) described in Japanese Patent Laid-Open No. 253467/1996 or EP722940A.

Process (A)

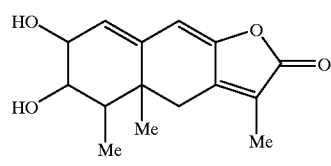

(III)

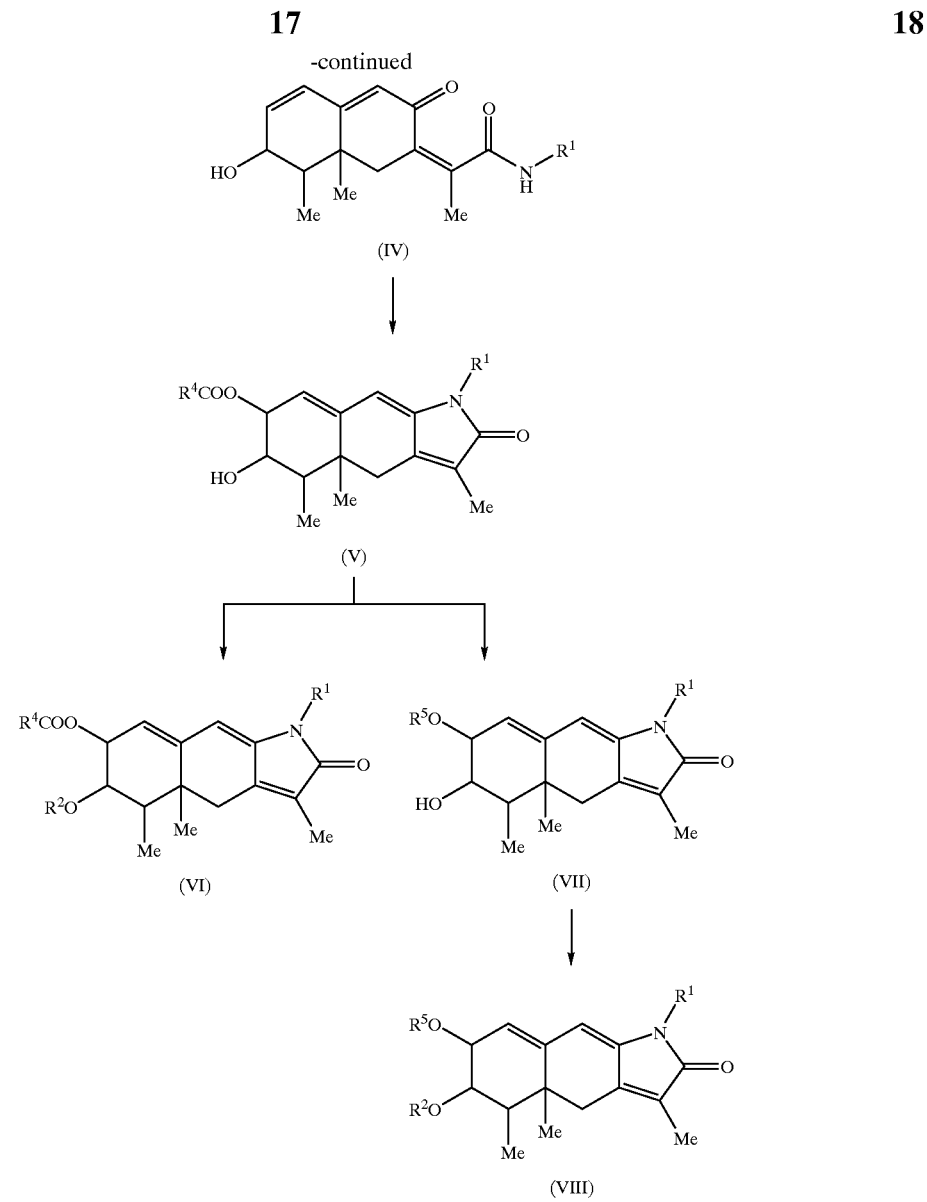

wherein
  R$^1$ and R$^2$ are as defined above in the formula (I);
  R$^4$ represents an optionally substituted C$_1$–C$_{10}$ alkyl, optionally substituted C$_2$–C$_{10}$ alkenyl, optionally substituted C$_2$–C$_{10}$ alkynyl, optionally substituted C$_3$–C$_{10}$ cycloalkyl, optionally substituted C$_6$–C$_{15}$ aryl, or optionally substituted C$_7$–C$_{15}$ aralkyl; and
  R$^5$ represents a hydrogen atom, an optionally substituted C$_1$–C$_{10}$ alkyl, optionally substituted C$_2$–C$_{10}$ alkenyl, optionally substituted C$_2$–C$_{10}$ alkynyl, optionally substituted C$_3$–C$_{10}$ cycloalkyl, or optionally substituted C$_7$–C$_{15}$ aralkyl.

In the process (A), the starting compound PF1092C represented by the formula (III) is reacted with a sulfonyl halide in the presence of a necessary or excess amount of a base. The reaction product is then immediately subjected to a coupling reaction with a primary amine represented by R$^1$—NH$_2$ (wherein R$^1$ is as defined above in the formula (I)) to give an amide compound represented by the formula (IV).

Bases usable in the sulfonylation include organic bases such as pyridine, lutidine, collidine, triethylamine, and dimethylaminopyridine. Preferably, diisopropylethylamine is used in an amount of one to three equivalents. Sulfonyl halides usable herein include p-toluenesulfonyl chloride and benzylsulfonyl chloride. Preferably, methanesulfonyl chloride is used in an amount of one to two equivalents.

The reaction proceeds in a good yield in a suitable solvent (for example, methylene chloride, chloroform, benzene, toluene, or xylene) at a temperature in the range of –30° C. to 10° C., and the reaction time is about 5 min to one hr.

Primary amines usable in the subsequent amidation include primary alkylamines having an organic group corresponding to R$^1$, such as methylamine, ethylamine, isopropylamine, benzylamine, and 4-methoxybenzylamine, and preferably, the primary amine is used in an amount of one to 10 equivalents.

The reaction proceeds in a good yield in a suitable solvent (for example, methylene chloride, chloroform, 1,4-dioxane, ether, or tetrahydrofuran (THF), preferably THF) at a temperature in the range of 0 to 50° C., and the reaction time is about 1 to 24 hr.

In the process (A), the compound represented by the formula (IV) is then subjected to a ring-closing reaction with a carboxylic acid to give a compound represented by the formula (V) with a carbonyloxy group having α configuration being stereoselectively introduced thereinto. In the ring-closing reaction, an aliphatic carboxylic acid or an aromatic carboxylic acid $R^4$—COOH having an organic group corresponding to desired $R^4$—CO— (wherein $R^4$ is as defined above) of the compound represented by the formula (V), such as acetic acid, propionic acid, or butyric acid is used in an amount of preferably five (5) equivalents to an excess amount. Therefore, the selection of the carboxylic acid in this step is important. The reaction proceeds in a solvent (for example, THF, 1,4-dioxane, or acetonitrile, preferably acetonitrile) at a temperature in the range of 0 to 100° C., and the reaction time is about 1 to 24 hr.

The step of introducing $R^2$ into the compound represented by the formula (V) to give the compound represented by the formula (VI) may be carried out by methods (1) to (5), described below, depending upon the type of the group $R^2$.

On the other hand, in the process (A), a compound represented by the formula (VII) with the substituent $R^5$O- held at the α configuration is derived from the compound represented by the formula (V) by a substitution reaction with a nucleophilic reagent. The nucleophilic reagent is determined by the side chain of $R^5$O introduced into the compound represented by the formula (VII). Therefore, $R^5$—OH (wherein $R^5$ is as defined above) is used as the nucleophilic agent, and specific examples of compounds usable herein include optionally substituted $C_1$–$C_{10}$ alkyl alcohols, optionally substituted $C_2$–$C_{10}$ alkenyl alcohols, optionally substituted $C_2$–$C_{10}$ alkynyl alcohols, optionally substituted $C_3$–$C_{10}$ cycloalkyl alcohols, and optionally substituted $C_7$–$C_{15}$ aralkyl alcohols. Further, for example, when $R^5$ represents a $C_1$–$C_{10}$ alkyl side chain, methanol, ethanol, propanol, isopropanol, or butanol is used as the nucleophilic reagent. This nucleophilic reagent can serve also as the solvent for the reaction and hence is preferably used in large excess. The reaction proceeds in a good yield at a temperature in the range of 20 to 100° C., and the reaction time is about 30 min to 24 hr.

When the $R^5$ in the compound represented by the formula (VII) represents a hydrogen atom, water may be used as the nucleophilic reagent. When THF, 1,4-dioxane, or acetonitrile, preferably acetonitrile, is used as the solvent, the reaction smoothly proceeds. Preferably, water is used in large excess. The reaction proceeds in a good yield at a temperature in the range of 20 to 100° C., and the reaction time is about 30 min to 24 hr.

The step of introducing $R^2$ into the compound represented by the formula (VII) to give the compound represented by the formula (VIII) may be carried out by methods (1) to (5), described below, depending upon the type of the group $R^2$.

Process (B)

The compounds represented by the formula (I) according to the present invention may be synthesized also by the following process.

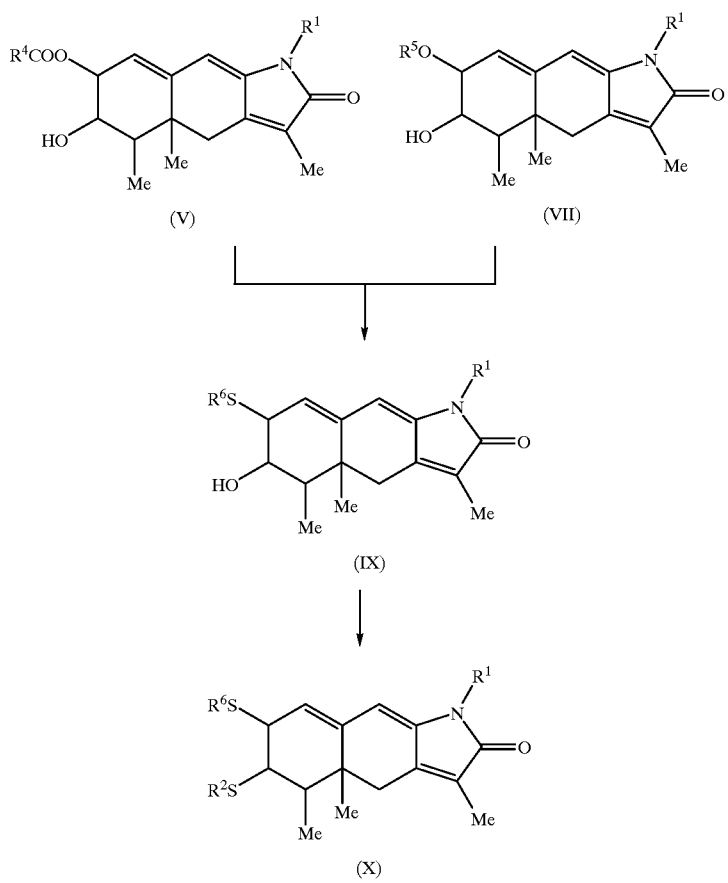

wherein

R$^1$ is as defined above in the formula (I); and

R$^6$ represents an optionally substituted C$_1$–C$_{10}$ alkyl, optionally substituted C$_2$–C$_{10}$ alkenyl, optionally substituted C$_2$–C$_{10}$ alkynyl, optionally substituted C$_3$–C$_{10}$ cycloalkyl, optionally substituted C$_6$–C$_{15}$ aryl, or optionally substituted C$_7$–C$_{15}$ aralkyl.

In the process (B), the compound represented by the formula (V) or (VII) is reacted with a thiol compound represented by the formula R$^6$-SH (wherein R$^6$ is as defined above) in the presence of a necessary amount of an organic acid to give a compound represented by the formula (IX). In this reaction, preferably, the compound R$^6$-SH is used in an amount of one equivalent to an excess amount. Organic acids usable in the reaction include camphorsulfonic acid, p-toluenesulfonic acid, and methanesulfonic acid. Preferably, methanesulfonic acid is used in an amount of 0.1 to 1 equivalent. The reaction proceeds in a suitable solvent (for example, chloroform, benzene, toluene, xylene, or methylene chloride with methylene chloride being preferred) at a temperature in the range of 0 to 100° C., and the reaction time is about one min to one hr.

The step of introducing the group R$^2$ into the compound represented by the formula (IX) to give the compound represented by the formula (X) may be carried out by methods (1) to (5), described below, depending upon the type of the group R$^2$.

Process (C)

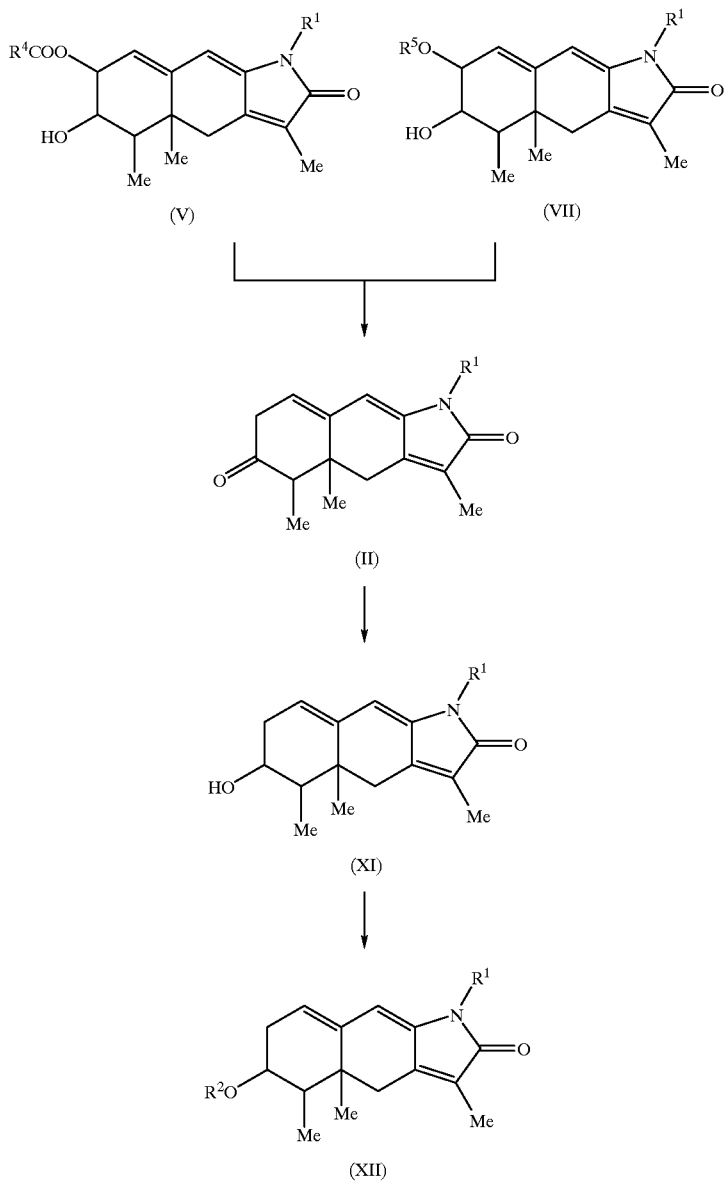

wherein R$^1$, R$^4$, and R$^5$ are as defined above.

In the process (C), the compound represented by the formula (V) or (VII) may be reacted with a necessary amount of an organic acid to give a compound represented by the formula (II). In this reaction, organic acids usable herein include camphorsulfonic acid, p-toluenesulfonic acid, and methanesulfonic acid. Preferably, methanesulfonic acid is used in an amount of 0.1 to 1 equivalent. The reaction proceeds in a good yield in a suitable solvent (for example, methylene chloride, chloroform, benzene, toluene, or xylene) at a temperature in the range of 20 to 10° C., and the reaction time is about one min to one hr.

Subsequently, the compound represented by the formula (II) may be reduced with sodium borohydride to give a compound represented by the formula (XI) with the 6-position being stereoselectively converted to a hydroxyl group of β configuration. Reducing agents usable in this reduction reaction include lithium borohydride, tetrabutyl ammonium borohydride, and sodium borohydride. Preferably, sodium borohydride is used in an amount of one to five equivalents. The reaction proceeds in a good yield in a solvent (for example, an alcoholic solvent, preferably methanol) at a temperature in the range of −10° C. to 50° C., and the reaction time is about one min to 3 hr.

The step of introducing the group $R^2$ into the compound represented by the formula (XI) to give the compound represented by the formula (XII) may be carried out by methods (1) to (5), described below, depending upon the type of the group $R^2$.

Process (D)

The compounds represented by the formula (I) according to the present invention may be synthesized also by the following process.

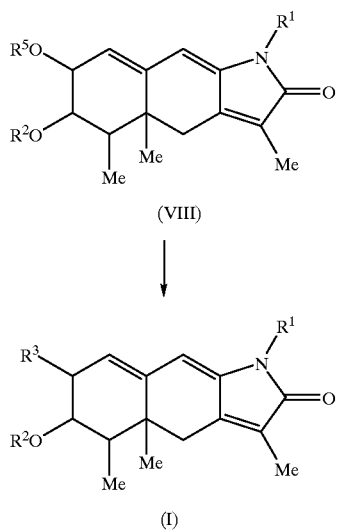

wherein $R^1$ is as defined above in the formula (I);

$R^2$ is as defined above in the formula (I) excluding the hydrogen atom; and $R^5$ is as defined above.

In this process, only the 7-position in the compound represented by the formula (VIII) is directly converted to a desired organic group (excluding a hydrogen atom) to give the compound represented by the formula (I) (wherein $R^1$ is defined above in the formula (I), $R^2$ is as defined above in the formula (I) excluding the hydrogen, atom, and $R^3$ is as defined above in the formula (I) excluding the hydrogen atom).

In particular, the starting compound represented by the formula (VIII) is subjected to a substitution reaction with a compound having an organic group corresponding to desired $R^3$ optionally in the presence of an acid in a necessary amount or an excess amount to give the compound represented by the formula (I). Examples of compounds having an organic group corresponding to $R^3$ include alcohols, thiols, carboxylic acids, and water. Preferably, the substitution reaction using an alkyl alcohol, an alkyl thiol, an aryl thiol or the like is carried out in the presence of an organic acid, such as camphorsulfonic acid, p-toluenesulfonic acid, or methanesulfonic acid. Preferably, methanesulfonic acid is used in an amount of 0.1 to 1 equivalent. On the other hand, when an aliphatic carboxylic acid or an aromatic carboxylic acid is used, there is no need to add any acid because the reagent per se acts as an acid catalyst. In the case of the substitution reaction using water, use of hydrochloric acid as the acid catalyst in excess is preferred. The reaction proceeds in a solvent (for example, methylene chloride, chloroform, benzene, toluene, xylene, or acetonitrile) at a temperature in the range of from 0 to 100° C., and the reaction time is about one min to one hr.

Introduction of $R^2$

The modification of a hydroxyl group at the 6-position, that is, the introduction of the modification group corresponding to $R^2$, of the compound represented by the formula (I) (wherein $R^1$ is as defined above, $R^2$ represents a hydrogen atom, and $R^3$ is as defined above in the formula (I) excluding the hydroxyl group) may be preferably carried out by any one of the following methods (1) to (5).

Method (1)

The compounds represented by the formula (I) [wherein $R^1$ is as defined above in the formula (I);

$R^2$ represents optionally substituted $C_1$–$C_{10}$ alkylcarbonyl, optionally substituted $C_2$–$C_{10}$ alkenylcarbonyl, optionally substituted $C_2$–$C_{10}$ alkynylcarbonyl, optionally substituted $C_3$–$C_{15}$ cycloalkylcarbonyl, optionally substituted $C_7$–$C_{15}$ aromatic acyl, optionally substituted $C_7$–$C_{15}$ aralkylcarbonyl, optionally substituted $C_2$–$C_{15}$ heteroaromatic acyl having at least one nitrogen, oxygen, and sulfur atom, or optionally substituted $C_3$–$C_{15}$ saturated heterocyclic acyl having at least one nitrogen, oxygen, or sulfur atom; and $R^3$ is as defined above in the formula (I) excluding the hydroxyl group] may be prepared by reacting the compound represented by the formula (I) (wherein $R^1$ is as defined above in the formula (I), $R^2$ represents a hydrogen atom, and R is as defined above in the formula (I) excluding the hydroxyl group) with a suitable acylating agent in the presence of a base.

The acylating agent may be properly selected according to the structure of desired $R^2$, and examples thereof include optionally substituted $C_1$–$C_{10}$ alkylcarbonyl halides (for example, acetyl chloride), optionally substituted $C_2$–$C_{10}$ alkenylcarbonyl halides, optionally substituted $C_2$–$C_{10}$ alkynylcarbonyl halides, $C_3$–$C_{15}$ cycloalkylcarbonyl halides, optionally substituted $C_7$–$C_{15}$ aralkylcarbonyl halides, optionally substituted $C_6$–$C_{15}$ aromatic acyl halides, optionally substituted $C_2$–$C_{15}$ heteroaromatic acyl halides having at least one nitrogen, oxygen, or sulfur atom, and acid anhydrides, such as acetic anhydride and propionic anhydride. Preferably, the acylating agent is used in an amount of 1 to 5 equivalents. The reaction may be carried out in a solvent, such as pyridine, which serves also as a base, or in a combination of an aprotic solvent, used in the conventional acylation, with an organic base. The reaction proceeds in a good yield at a temperature in the range of 20 to 60° C., and the reaction time is about 1 to 24 hr.

The production process of the compound wherein $R^2$ represents imidazol-1-ylcarbonyl among optionally substituted $C_2$–$C_{15}$ heteroaromatic acyls having at least one nitrogen, oxygen, or sulfur atom will be described in the method (3) below.

Method (2)

The compounds represented by the formula (I) [wherein
R$^1$ is as defined above in the formula (I);

R$^2$ represents optionally substituted C$_1$–C$_{10}$ alkyl, optionally substituted C$_2$–C$_{10}$ alkenyl, optionally substituted C$_2$–C$_{10}$ alkynyl, optionally substituted C$_3$–C$_{10}$ cycloalkyl, or optionally substituted C$_7$–C$_{15}$ aralkyl;

R$^3$ represents optionally substituted C$_1$–C$_{10}$ alkyloxy, optionally substituted C$_2$–C$_{10}$ alkenyloxy, optionally substituted C$_2$–C$_{10}$ alkynyloxy, optionally substituted C$_3$–C$_{10}$ cycloalkyloxy, or optionally substituted C$_7$C$_{15}$ aralkyloxy] may be prepared by reacting the compound represented by the formula(I) (wherein R$^1$ is as defined in claim 1, R$^2$ represents a hydrogen atom, and R$^3$ represents optionally substituted C$_1$–C$_{10}$ alkyloxy, optionally substituted C$_2$–C$_{10}$ alkenyloxy, optionally substituted C$_2$–C$_{10}$ alkynyloxy, optionally substituted C$_3$–C$_{10}$ cycloalkyloxy, or optionally substituted C$_7$–C$_{15}$ aralkyloxy) with a suitable alkylating agent in the presence of a base.

The alkylating agent may be properly selected according to the structure of desired R$^2$, and examples thereof include optionally substituted C$_1$–C$_{10}$ alkyl halides (for example, methyl iodide), optionally substituted C$_2$–C$_{10}$ alkenyl halides, optionally substituted C$_2$–C$_{10}$ alkynyl halides, optionally substituted C$_3$–C$_{10}$ cycloalkyl halides, and optionally substituted C$_7$–C$_{15}$ aralkyl halides. Preferably, the alkylating agent is used in an amount of one equivalent to an excess amount. Bases usable in the alkylation include metal hydrides, such as sodium hydride and potassium hydride. Preferably, the base is used in an amount of 1 to 20 equivalents. The reaction proceeds in a good yield in a suitable solvent (for example, a solvent used in the conventional alkylation, such as dimethylformamide (DMF), benzene, toluene, methylene chloride, or chloroform) at a temperature in the range of 20 to 100° C., the reaction time is about 30 min to 24 hr.

Method (3)

The compounds represented by the formula (I) [wherein R$^1$ is as defined above in the formula (I);

R$^2$ represents carbamoyl, optionally substituted C$_1$–C$_{10}$ alkylcarbamoyl, N, N-di-C$_1$–C$_{10}$ alkylaminocarbonyl, optionally substituted C$_3$–C$_{10}$ cycloalkylcarbamoyl, optionally substituted C$_6$–C$_{15}$ aromatic carbamoyl, or optionally substituted C$_7$–C$_{15}$ aralkylcarbamoyl; and R$^3$ is as defined above in the formula (I) excluding the hydroxyl group] may be prepared as follows.

The compound represented by the formula (I) (wherein R$^1$ is as defined above in the formula (I), R$^2$ represents a hydrogen atom, and R$^3$ is as defined above in the formula (I) excluding the hydroxyl group) is reacted with 1,1-carbonyldiimidazole to give a compound with the 6-position being imidazol-1-ylcarbonylated. Preferably, 1,1-carbonyldiimidazole is used in an amount of 1 to 3 equivalents. The reaction proceeds in a good yield in a suitable solvent (for example, methylene chloride, chloroform, benzene, toluene, or xylene) at a temperature in the range of –30° C. to 30° C., and the reaction time is about 30 min to 24 hr.

The compound thus prepared is optionally reacted with an equivalent of a methylating agent to give an onium ion which is then reacted with ammonia or an amine, such as C$_1$–C$_{10}$ alkylamine optionally having a primary or secondary substituent (for example, n-propylamine), N,N-di-C$_1$–C$_{10}$ alkylamine, optionally substituted C$_3$–C$_{10}$ cycloalkylamine, optionally substituted C$_7$–C$_{15}$ aralkylamine, optionally substituted C$_6$–C$_{15}$ aromatic amine, or optionally substituted C$_2$–C$_{15}$ saturated heterocyclic amine having at least one nitrogen, oxygen, or sulfur atom to give a compound with R$^2$ being carbamoylated.

The methylation which is first carried out is effective in the substitution reaction with an amine having poor reactivity. Use of about one equivalent of an alkylating agent having a high onium ionization capability, such as methyl triflate, is preferred. The reaction proceeds in a good yield in a solvent (for example, methylene chloride, chloroform, ether, or THF) at a temperature in the range of –20° C. to 30° C., and the reaction time is about 10 min to one hr.

The amount of the reagent used in the subsequent reaction with the amine is preferably one equivalent to an excess amount. The reaction proceeds in a good yield in a solvent (for example, toluene, benzene, xylene, or DMF) at a temperature in the range of 0 to 100 ° C., and the reaction time is about 30 min to 3 days.

Further, the compound represented by the formula(I) (wherein R$^1$ is as defined above in the formula (I), R$^2$ represents a hydrogen atom, and R$^3$ is as defined above in the formula (I) excluding the hydroxyl group) may be used as a starting compound and reacted with a reagent capable of carbamoylating the hydroxyl group in the presence of a necessary amount of a base to give a compound with R$^2$ being carbamoylated.

Bases usable in the carbamoylation include organic bases, such as pyridine, lutidine, collidine, triethylamine, and diisopropylethylamine. Preferably, 4-dimethylaminopyridine is used in a catalytic amount. An isocyanate, such as propyl isocyanate, is used as a carbamoylating reagent in an amount of preferably one equivalent to an excess amount. The reaction proceeds in a good yield in a solvent (for example, DMF, methylene chloride, chloroform, benzene, or toluene with DMF being preferred) at a temperature in the range of 25 to 120 ° C., and the reaction time is about 1 to 24 hr.

Method (4)

The compounds represented by the formula (I) [wherein R$^1$ is as defined above in the formula (I);

R$^2$ represents optionally substituted C$_1$–C$_{10}$ alkoxycarbonyl, optionally substituted C$_6$–C$_{15}$ aryloxycarbonyl, optionally substituted C$_7$–C$_{15}$ aralkyloxycarbonyl; and R$^3$ is as defined above in the formula (I) excluding the hydroxyl group] may be prepared by carbonating the compound represented by the formula (I) (wherein R$^1$ is as defined above in the formula (I), R$^2$ represents a hydrogen atom, and R$^3$ represents is as defined above in the formula (I) excluding the hydroxyl group).

Examples of carbonating reagents usable herein include optionally substituted C$_1$–C$_{10}$ alkoxycarbonyl halides (for example, ethoxycarbonyl chloride), optionally substituted C$_6$–C$_{15}$ aryloxycarbonyl halides, and optionally substituted C$_7$–C$_{15}$ aralkyloxycarbonyl halides. Preferably, the reagent is used in an amount of 1 to 5 equivalents. The reaction proceeds in a good yield in a solvent (pyridine serving also as a base, or a combination of an aprotic solvent and an organic base used in the conventional carbonation) at a temperature in the range of 20 to 60° C., and the reaction time is about 1 to 30 hr.

Method (5)

The compounds represented by the formula (I) [wherein R$^1$ is as defined above in the formula (I);

R$^2$ represents optionally substituted C$_1$–C$_{15}$ heteroaromatic thiocarbonyl group having at least one nitrogen, oxygen, or sulfur atom, optionally substituted C$_2$–C$_{15}$ saturated heterocyclic thiocarbonyl having at least one nitrogen, oxygen, or sulfur atom, or optionally substituted $C_1-C_{10}$ alkylthiocarbamoyl; and $R^3$ is as defined above in the formula (I) excluding the hydroxyl group] may be prepared as follows.

The compound represented by the formula (I) (wherein $R^1$ is as defined above in the formula (I), $R^2$ represents a hydrogen atom, and $R^3$ is as defined above in the formula (I) excluding the hydroxyl group) is reacted with 1,1'-thiocarbonyldiimidazole to prepare a compound with $R^2$ being imidazol-1-ylthiocarbonylated. In this reaction, preferably, 1,1'-thiocarbonyldiimidazole is used in an amount of 1 to 3 equivalents. The reaction proceeds in a good yield in a solvent (for example, methylene chloride, chloroform, benzene, toluene, or xylene) at a temperature in the range of 0 to 60° C., and the reaction time is about one hr to two days.

The compound thus prepared is then reacted with an amine, such as $C_1-C_{10}$ alkylamine optionally having a primary or secondary substituent, $C_3-C_{10}$ cycloalkylamine, optionally substituted $C_7-C_{15}$ aralkylamine, optionally substituted $C_6-C_{15}$ aromatic amine, or optionally substituted $C_2-C_{15}$ saturated heterocyclic amine having at least one nitrogen, oxygen, or sulfur atom to give a derivative with $R^2$ being thiocarbamoylated.

In this reaction, preferably, the amine is used in an amount of one equivalent to an excess amount. The reaction proceeds in a good yield in a solvent (for example, toluene, benzene, xylene, or DMF) at a temperature in the range of from 20 to 100° C., and the reaction time is about 30 min to 24 hr.

Besides the methods (1) to (5), for example, introduction of a modifying group by alkoxyalkylation, sulfonylation or the like under basic conditions and, in addition, the conventional substitution reaction for modifying a hydroxyl group, such as an acetal modification reaction, without creating side reactions, such as cleavage of a lactam ring, allyl rearrangement, and elimination, even under acidic conditions through selection of suitable conditions permit the introduction of $R^2$.

In the novel skeleton wherein $R^5$ represents a hydrogen atom, among the compounds represented by the formula (VII), both the 6- and 7-positions are a free secondary hydroxyl group. One of the hydroxyl groups is a hydroxyl group at the allyl position. Therefore, two hydroxyl groups may be freely modified by quite the same manner as used in the modification of a hydroxyl group in the prior application (WO 97/30040) utilizing the difference in reactivity.

Further, for the fundamental skeleton represented by the formulae (V) and (IX), for example, the alkylation of the hydroxyl group at the 6-position causes the side chain at the 7-position to undergo hydrolysis or alkylation under the reaction conditions. Thus, the modification of the hydroxyl group at the 6-position in the above manner leads to a fear of affecting the side chain at the 7-position. Therefore, when the modification cannot be directly carried out, the adoption of the above method is very effective. Further, the above method is useful also in the case where, in the synthesis of the compound represented by the formula (I) (wherein $R^1$ is as defined above in the formula (I), $R^2$ is as defined above in the formula (I) excluding the hydrogen atom, and R represents a hydroxyl group) by the protection of the hydroxyl group at the 7-position and the deprotection, a desired compound cannot be prepared due to rearrangement between the 6- and 7-positions depending upon reaction conditions or the type of the side chain. Further, also when the compound represented by the formula (VI) is used as the starting compound, the 7-position can be converted in quite the same manner as described above.

Compounds Represented by the Formula (II)/Intermediates for Synthesis

The present invention provides compounds represented by the formula (II) or pharmaceutically acceptable salts thereof. These compounds are useful as an intermediate for the synthesis of the compounds represented by the formula (I). Therefore, in the formula, $R^1$ is as defined above in $R^1$ in the formula (I), and preferred examples thereof also include those described above in R in the formula (I).

EXAMPLES

Example 1

Compound Represented by Formula (IV) wherein $R^1$ Represents Methyl

A compound represented by the formula (III) (200 mg=0.76 mmol) was dissolved in methylene chloride (4 ml), and the solution was cooled to −15° C. Methanesulfonyl chloride (88 μl=1.15 mmol) was added thereto in the presence of diisopropylethylamine (266 μl=1.53 mmol), and the mixture was stirred for 15 min. Methylene chloride (20 ml) was added thereto, the mixture was washed with saturated saline (20 ml), and the solvent was removed under reduced pressure. A 2 M methylamine/THF solution (2.29 ml) was added to the reaction product, and the mixture was stirred at room temperature for one hr. The solvent was removed under reduced pressure to give the title crude compound (209 mg, 100%). The compound thus prepared, due to its instability, was immediately used to the next reaction without purification.

Example 2

(4aR,5R,6R,7R)-7-Acetoxy-6-hydroxy-4a,5,6,7-tetrahydro-1,3,4a,5-tetramethylbenz[f]indol-2(4H)-one The compound (100 mg=0.36 mmol) prepared in Example 1 was dissolved in acetonitrile (5 ml), acetic acid (200 μl=3.30 mmol) was added to the solution, and the mixture was stirred at room temperature for 20 hr. Methylene chloride (20 ml) was added to the reaction solution, the mixture was washed with a saturated aqueous sodium hydrogencarbonate solution (20 ml×2) and saturated saline (20 ml), and the organic phase was dried over sodium sulfate. The solvent was removed under reduced pressure, and the residue was purified by preparative TLC to give the title compound (85 mg, 74%).

$^1$H NMR (CDCl$_3$) δ 1.14 (3H, s, 4a-CH$_3$), 1.20 (3H, d, J=7.2 Hz, 5-CH$_3$), 1.88 (3H, d, J=2.0 Hz, 3-CH$_3$), 1.90 (1H, dq, J=7.2, 2.9 Hz, 5-H), 2.06 (3H, s, OCOCH$_3$), 2.16 (1H, br d, J=16.0 Hz, 4-H), 2.82 (1H, d, J=16.0 Hz, 4-H), 3.10(3H, s, N—CH$_3$), 3.84 (1H, m, 6-H), 5.20 (1H, dd, J=4.8, 1.7 Hz, 7-H), 5.70 (1H, d, J=4.8 Hz, 8-H), 5.75 (1H, s, 9-H); MS (EI) m/z 317 (M)$^+$; $[\alpha]^{18}_D$ −608° (c 1.0, MeOH); mp 50–55° C.

Example 3

(4aR,5R,6R,7R)-7-Acetoxy-6-propionyloxy-4a,5,6,7-tetrahydro-1,3,4a,5-tetramethylbenz[f]indol-2(4H)-one The compound (22 mg=0.07 mmol) prepared in Example 2 was dissolved in pyridine (1 ml), propionyl chloride (21 μl=0.35 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (6 mg, 23%).

$^1$H NMR (CDCl$_3$) δ 1.09 (3H, d, J=7.2 Hz, 5-CH$_3$), 1.11 (3H, s, 4a-CH$_3$), 1.14 (3H, t, J=7.6 Hz, OCOCH$_2$CH$_3$), 1.88 (3H, d, J=1.9 Hz, 3-CH$_3$), 2.05 (3H, s, OCOCH$_3$), 2.10 (1H, dq, J=7.2, 2.8 Hz, 5-H), 2.17 (1H, br d, J=15.9 Hz, 4-H), 2.34 (2H, q, J=7.6 Hz, OCOCH$_2$CH$_3$), 2.83 (1H, d, J=15.9 Hz, 4-H), 3.10 (3H, s, N—CH$_3$), 5.08 (1H, m, 6-H), 5.13 (1H, dd, J=4.7, 1.6 Hz, 7-H), 5.73 (1H, s, 9-H), 5.76 (1H, d, J=4.7 Hz, 8-H); MS (FAB)m/z 374 (M+H)$^+$; [α]$^{20}_D$ −291° (c 1.0, MeOH).

Example 4

(4aR,5R,6R,7R)-7-Acetoxy-6-(2-furancarbonyloxy)-4a,5,6,7-tetrahydro-1,3,4a,5-tetramethylbenz[f]indol-2(4H)-one In the same manner as in Example 3, the compound (10 mg=0.03 mmol) prepared in Example 2 was dissolved in pyridine (1 ml), 2-furoyl chloride (9 μl=0.09 mmol) was added to the solution, and the mixture was stirred at room temperature for 15 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (6 mg, 49%).

$^1$H NMR (CDCl$_3$) δ 1.15 (3H, d, J=7.2 Hz, 5-CH$_3$), 1.21 (3H, s, 4a-CH$_3$), 1.89 (3H, d, J=1.9 Hz, 3-CH$_3$), 2.07 (3H, s, OCOCH$_3$), 2.20 (1H, dq, J=7.2, 2.8 Hz, 5-H), 2.21 (1H, br d, J=15.9 Hz, 4-H), 2.86 (1H, d, J=15.9 Hz, 4-H), 3.11 (3H, s, N—CH$_3$), 5.26 (1H, dd, J=4.7, 1.6 Hz, 7-H), 5.29 (1H, m, 6-H), 5.76 (1H, s, 9-H), 5.80 (1H, d, J=4.7 Hz, 8-H), 6.49 (1H, dd, J=3.5, 1.7 Hz, OCOC$_4$H$_3$O), 7.12 (1H, dd, J=3.5, 0.8 Hz, OCOC$_4$H$_3$O), 7.57 (1H, dd, J=1.7, 0.8 Hz, OCOC$_4$H$_3$O); MS (EI)m/z 411 (M)$^+$; [α]$^{20}_D$ −269° (c 0.6, MeOH).

Example 5

(4aR,5R,6R,7R)-7-Acetoxy-6-(imidazol-1-ylcarbonyloxy)-4a,5,6,7-tetrahydro-1,3,4a,5-tetramethylbenz[f]indol-2(4H)-one The compound (100 mg=0.32 mmol) prepared in Example 2 was dissolved in methylene chloride (3 ml), 1,1'-carbonyldiimidazole (204 mg=1.26 mmol) was added to the solution, and the mixture was stirred at room temperature for 17 hr. Methylene chloride was added to the reaction mixture, the mixture was washed with water, and the organic phase was dried over sodium sulfate. The solvent was removed under reduced pressure, and the residue was purified by column chromatography on silica gel to give the title compound (130 mg, 100%).

$^1$H NMR (CDCl$_3$) δ 1.19 (3H, s, 4a-CH$_3$), 1.22 (3H, d, J=7.1 Hz, 5-CH$_3$), 1.91 (3H, d, J=1.9 Hz, 3-CH$_3$), 2.11 (3H, s, OCOCH$_3$), 2.25 (1H, br d, J=16.0 Hz, 4-H), 2.27 (1H, dq, J=7.1, 3.0 Hz, 5-H), 2.89 (1H, d, J=16.0 Hz, 4-H), 3.13 (3H, s, N—CH$_3$), 5.26 (1H, m, 6-H), 5.38 (1H, dd, J=4.8, 1.5 Hz, 7-H), 5.77(1H, d, J=4.8 Hz, 8-H), 5.78 (1H, s, 9-H), 7.09 (1H, br s, OCOC$_3$N$_2$), 7.39 (1H, br s, OCOC$_3$N$_2$),8.10 (1H, br s, OCOC$_3$N$_2$); MS (TSP) m/z 412(M+H)$^+$.

Example 6

(4aR,5R,6R,7R)-7-Acetoxy-6-(pyrrolidin-1-ylcarbonyloxy)-4a,5,6,7-tetrahydro-1,3,4a,5-tetramethylbenz[f]indol-2(4H)-one The compound (20 mg=0.05 mmol) prepared in Example 5 was dissolved in toluene (0.5 ml), pyrrolidine (20 μl=0.24 mmol) was added to the solution, the mixture was stirred at room temperature for 2 hr. Ethyl acetate was added to the reaction mixture, the mixture was washed with water, and the organic phase was dried over sodium sulfate. The solvent was removed under reduced pressure, and the residue was purified by column chromatography on silica gel to give the title compound (15 mg, 75%).

$^1$H NMR (CDCl$_3$) δ 1.13 (3H, s, 4a-CH$_3$), 1.16 (3H, d, J=7.1 Hz, 5-CH$_3$), 1.83–1.90 (4H, m, OCOC$_4$H$_8$N), 1.90 (3H, d, J=1.9 Hz, 3-CH$_3$), 2.05 (3H, s, OCOCH$_3$), 2.12 (1H, dq, J=7.1, 3.0 Hz, 5-H), 2.19 (1H, br d, J=16.5 Hz, 4-H), 2.85 (1H, d, J=16.5 Hz, 4-H), 3.11 (3H, s, N—CH$_3$), 3.18–3.51 (4H, m, OCOC$_4$H$_8$N), 4.98 (1H, m, 6-H), 5.23 (1H, dd, J=4.8, 1.5 Hz, 7-H), 5.75 (1H, s, 9-H), 5.81 (1H, d, J=4.8 Hz, 8-H); MS (FAB) m/z 415 (M+H)$^+$.

Example 7

(4aR,5R,6R,7R)-6-Hydroxy-7-propionyloxy-4a,5,6,7-tetrahydro-1,3,4a,5-tetramethylbenz[f]indol-2(4H)-one The compound (100 mg=0.36 mmol) prepared in Example 1 was dissolved in acetonitrile(5 ml), propionic acid (270 μl=3.60 mmol) was added to the solution, and the mixture was stirred at room temperature for 20 hr. Methylene chloride (20 ml) was added to the reaction mixture, the mixture was washed with a saturated aqueous sodium hydrogencarbonate solution (20 ml×2) and saturated saline (20 ml), and the organic phase was dried over sodium sulfate. The solvent was removed under reduced pressure, and the residue was purified by preparative TLC to give the title compound (68 mg, 57%).

$^1$H NMR (CDCl$_3$) δ 1.12 (3H, t, J=7.5 Hz, OCOCH$_2$CH$_3$), 1.13 (3H, s, 4a-CH$_3$), 1.19 (3H, d, J=7.2 Hz, 5-CH$_3$), 1.87 (3H, d, J=2.0 Hz, 3-CH$_3$), 1.88 (1H, dq, J=7.2, 2.9 Hz, 5-H), 2.15(1H, br d, J=16.0 Hz, 4-H), 2.31 (1H, ap q, J=7.5 Hz, OCOCH$_2$CH$_3$), 2.34 (1H, ap q, J=7.5 Hz, OCOCH$_3$CH$_3$), 2.81 (1H, d, J=16.0 Hz, 4-H), 3.09(3H, s, N—CH$_3$), 3.81 (1H, m, 6-H), 5.21 (1H,dd, J=4.8, 1.7 Hz, 7-H), 5.70 (1H, d, J=4.8 Hz, 8-H), 5.75 (1H, s, 9-H); MS (EI)m/z 331 (M)$^+$.

Example 8

(4aR,5R,6R,7R)-6,7-Dipropionyloxy-4a,5,6,7-tetrahydro-1,3,4a,5-tetramethylbenz[f]indol-2(4H)-one The compound (27 mg=0.08 mmol) prepared in Example 7 was dissolved in pyridine (1 ml), propionyl chloride (25 μl=0.40 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (14 mg, 45%).

$^1$H NMR (CDCl$_3$) δ 1.08 (3H, d, J=7.2 Hz, 5-CH$_3$), 1.10 (3H, s, 4a-CH$_3$),1.12 (3H, t, J=7.5 Hz, OCOCH$_2$CH$_3$), 1.13 (3H, t, J=7.6 Hz, OCOCH$_2$CH$_3$), 1.87 (3H, d, J=1.9 Hz, 3-CH$_3$), 2.09(1H, dq, J=7.2, 2.8 Hz, 5-H), 2.16 (1H, br d, J=15.9 Hz, 4-H), 2.30 (1H, ap q,J=7.5 Hz, OCOCH$_2$CH$_3$), 2.31 (1H, ap q,J=7.5 Hz, OCOCH$_2$CH$_3$), 2.34 (2H, q, J=7.6 Hz, OCOCH$_2$CH$_3$), 2.82 (1H, d, J=15.9 Hz, 4-H), 3.09 (3H, s, N—CH$_3$), 5.07 (1H, m, 6-H), 5.13 (1H, dd, J=4.7, 1.6 Hz, 7-H), 5.73 (1H, s, 9-H), 5.76 (1H, d, J=4.7 Hz, 8-H); MS (FAB)m/z 388 (M+H)$^+$; [α]$^{18}_D$ −454° (c 1.0, MeOH).

Example 9
(4aR,5R,6R,7R)-6-(2-Furancarbonyloxy)-7-propionyloxy-4a,5,6,7-tetrahydro-1,3,4a,5-tetramethylbenz[f]indol-2(4H)-one The compound (25 mg=0.08 mmol) prepared in Example 7 was dissolved in pyridine (1 ml), 2-furoyl chloride (22 μl=0.23 mmol) was added to the solution, and the mixture was stirred at room temperature for 19 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (12 mg, 37%).

$^1$H NMR (CDCl$_3$) δ 1.12 (3H, t, J=7.5 Hz, OCOCH$_2$CH$_3$), 1.14 (3H, d, J=7.2 Hz, 5-CH$_3$), 1.20 (3H, s, 4a-CH$_3$), 1.88 (3H, d, J=1.9 Hz, 3-CH$_3$), 2.19 (1H, dq, J=7.2, 2.8 Hz, 5-H), 2.20 (1H, br d, J=15.9 Hz, 4-H), 2.33 (1H, ap q, J=7.5 Hz, OCOCH$_2$CH$_3$), 2.34 (1H, ap q, J=7.5 Hz, OCOCH$_2$CH$_3$), 2.85 (1H, d, J=15.9 Hz, 4-H), 3.10 (3H, s, N—CH$_3$), 5.27 (1H, m, 7-H), 5.27 (1H, m, 6-H), 5.76 (1H, s, 9-H), 5.80 (1H, d, J=4.7 Hz, 8-H), 6.49 (1H, dd, J=3.5, 1.7 Hz, OCOC$_4$H$_3$O), 7.12 (1H, dd, J=3.5, 0.8 Hz, OCOC$_4$H$_3$O), 7.57 (1H, dd, J=1.7, 0.8 Hz, OCOC$_4$H$_3$O); MS (FAB) m/z 426 (M+H)$^+$; [α]$^{18}_D$ −245° (c 1.0, MeOH).

Example 10
(4aR,5R,6R,7R)-6,7-Dihydroxy-4a,5,6,7-tetrahydro-1,3,4a,5-tetramethylbenz[f]indol-2(4H)-one The compound (100 mg=0.32 mmol) prepared in Example 2 was dissolved in acetonitrile (5 ml), water (5 ml) was added to the solution, and the mixture was stirred at room temperature for 20 hr. Methylene chloride (20 ml) was added thereto, and the mixture was washed with saturated saline (20 ml), and the organic phase was dried over sodium sulfate. The solvent was removed under reduced pressure, and the residue was purified by preparative TLC to give the title compound (63 mg, 71%).

$^1$H NMR (CDCl$_3$) δ 1.11 (3H, s, 4a-CH$_3$), 1.20 (3H, d, J=7.2 Hz, 5-CH$_3$), 1.86 (3H, d, J=1.9 Hz, 3-CH$_3$), 1.94 (1H, dq, J=7.2, 2.5 Hz, 5-H), 2.08 (1H, br d, J=15.9 Hz, 4-H), 2.80 (1H, d, J=15.9 Hz, 4-H), 3.10 (3H, s, N—CH$_3$), 3.87 (1H, m, 6-H), 4.17 (1H, dd, J=4.8, 1.9 Hz, 7-H), 5.73 (1H, s, 9-H), 5.80 (1H, d, J=4.8 Hz, 8-H); MS (EI) m/z 275 (M)$^+$; [α]$^{20}_D$ −455° (c 0.2, MeOH).

Example 11
(4aR,5R,6R,7R)-7-(t-Butyldimethylsilyloxy)-6-hydroxy-4a,5,6,7-tetrahydro-1,3,4a,5-tetramethylbenz[f]indol-2(4H)-one The compound (200 mg=0.73 mmol) prepared in Example 10 was dissolved in DMF (10 ml), t-butyldimethylsilyl chloride (650 mg=4.31 mmol) was added to the solution in the presence of imidazole (500 mg=7.34 mmol), and the mixture was stirred at room temperature for 15 hr. Ethyl acetate was added to the reaction mixture, the mixture was washed with water, and the organic phase was dried over sodium sulfate. The solvent was removed under reduced pressure, and the residue was purified by column chromatography on silica gel to give the title compound (282 mg, 100%).

$^1$H NMR (CDCl$_3$) δ 0.10 (3H, s, OTBDMS), 0.11 (3H, s, OTBDMS), 0.89 (9H, s, OTBDMS), 1.11 (3H, s, 4a-CH$_3$), 1.19 (3H, d, J=7.3 Hz, 5-CH$_3$), 1.88 (3H, d, J=1.9 Hz, 3-CH$_3$), 2.02 (1H, dq, J=7.3, 2.3 Hz, 5-H), 2.17 (1H, br d, J=15.7 Hz, 4-H), 2.79 (1H, d, J=15.7 Hz, 4-H), 3.11 (3H, s, N—CH$_3$), 3.74 (1H, m, 6-H), 4.16 (1H, dd, J=4.8, 2.1 Hz, 7-H), 5.56 (1H, d, J=4.8 Hz, 8-H), 5.75 (1H, s, 9-H); MS (TSP) m/z 390 (M+H)$^+$.

Example 12
(4aR,5R,6R,7R)-6-Acetoxy-7-hydroxy-4a,5,6,7-tetrahydro-1,3,4a,5-tetramethylbenz[f]indol-2(4H)-one The procedure of Example 3 was repeated, except that the compound (20 mg=0.05 mmol) prepared in Example 11 was dissolved in methylene chloride (1 ml), acetyl chloride (18 μl=0.25 mmol) was added to the solution in the presence of pyridine (42 μl=0.52 mmol), and the mixture was stirred at room temperature for 17 hr. Thus, a corresponding acetyl compound (12 mg, 55%) was prepared.

This compound (12 mg=0.03 mmol) was dissolved in THF (1 ml), a 1 M tetrabutylammonium fluoride/THF solution (50 μl=0.05 mmol) was added to the solution, and the mixture was stirred at room temperature for 2 hr. Ethyl acetate was added to the reaction mixture, the mixture was washed with water, and the organic phase was dried over sodium sulfate. The solvent was removed under reduced pressure, and the residue was purified by preparative TLC to give the title compound (3 mg, 34%).

$^1$H NMR (CDCl$_3$) δ 1.10 (3H, s, 4a-CH$_3$), 1.11 (3H, d, J=7.2 Hz, 5-CH$_3$), 1.89 (3H, d, J=2.0 Hz,3-CH$_3$), 2.08 (3H, s, OCOCH$_3$), 2.14 (1H, br d, J=15.8 Hz, 4-H), 2.15 (1H, dq, J=7.2, 2.8 Hz, 5-H), 2.83 (1H, d, J=15.8 Hz, 4-H), 3.12 (3H, s, N—CH$_3$), 4.15 (1H, m, 7-H), 4.95 (1H, m, 6-H), 5.74 (1H, s, 9-H), 5.77 (1H, d, J=4.6 Hz, 8-H); MS (TSP) m/z 318 (M+H)$^+$.

Example 13
(4aR,5R,6R,7R)-7-Hydroxy-6-propionyloxy-4a,5,6,7-tetrahydro-1,3,4a,5-tetramethylbenz[f]indol-2(4H)-one The procedure of Example 3 was repeated, except that the compound (25 mg=0.06 mmol) prepared in Example 11 was dissolved in methylene chloride (1 ml), propionyl chloride (28 μl=0.28 mmol) was added to the solution in the presence of pyridine (52 μl=0.64 mmol), and the mixture was stirred at room temperature for 17 hr. Thus, a corresponding propionyl compound (7 mg, 25%) was prepared.

The procedure of Example 12 was repeated, except that the compound (10 mg=0.02 mmol) prepared just above was dissolved in THF (1 ml), a 1 M tetrabutylammonium fluoride/THF solution (50 μl=0.05 mmol) was added to the solution, and the mixture was stirred at room temperature for 2 hr. Thus, the title compound (1.4 mg, 34%) was prepared.

$^1$H NMR (CDCl$_3$) δ 1.10 (3H, s, 4a-CH$_3$), 1.11 (3H, d, J=7.1 Hz, 5-CH$_3$), 1.15 (3H, t, J=7.6 Hz, OCOCH$_2$CH$_3$), 1.89 (3H, d, J=2.0 Hz, 3-CH$_3$), 2.16 (1H, br d, J=15.0 Hz, 4-H), 2.16 (1H, dq, J=7.1, 3.1 Hz, 5-H), 2.35 (1H, q, J=7.6 Hz, OCOCH$_2$CH$_3$), 2.36 (1H, q, J=7.6 Hz, OCOCH$_2$CH$_3$), 2.82 (1H, d, J=15.0 Hz, 4-H), 3.12 (3H, s, N—CH$_3$), 4.14 (1H, dd, J=4.6, 1.2 Hz, 7-H), 4.96 (1H, m, 6-H), 5.74 (1H, s, 9-H), 5.77 (1H, d, J=4.6 Hz, 8-H); MS (TSP) m/z 332 (M+H)$^+$.

Example 14
(4aR,5R,6R,7R)-6-Cyclopropylcarbonyloxy-7-hydroxy-4a,5,6,7-tetrahydro-1,3,4a,5-tetramethylbenz[f]indol-2(4H)-one The compound (17 mg=0.05 mmol) prepared in Example 27 was dissolved in acetonitrile (0.3 ml), 1 N hydrochloric acid (0.17 ml=0.17 mmol) was added to the solution, and the mixture was stirred at room temperature for 30 min. Methylene chloride was added to the reaction mixture, and the mixture was washed with a saturated aqueous sodium hydrogencarbonate solution. The organic phase was dried over sodium sulfate. The solvent was removed under reduced pressure, and the residue was purified by preparative TLC to give the title compound (10 mg, 60%).

$^1$H NMR (CDCl$_3$) δ 0.79–0.96 (4H, m, OCOC$_3$H$_5$), 1.04 (3H, s, 4a-CH$_3$), 1.05 (3H, d, J=7.1 Hz, 5-CH$_3$), 1.53 (1H, m, OCOC$_3$H$_5$), 1.82 (3H, d, J=2.0 Hz, 3-CH$_3$), 2.08 (1H, dq, J=7.1, 2.9 Hz, 5-H), 2.09 (1H, br d, J=16.0 Hz, 4-H), 2.76 (1H, d, J=16.0 Hz, 4-H), 3.05 (3H, s, N—CH$_3$), 4.07 (1H, br d, J=4.0 Hz, 7-H), 4.87 (1H, m, 6-H), 5.68 (1H, s, 9-H), 5.70 (1H, d, J=4.0 Hz, 8-H); MS (TSP) m/z 344 (M+H)$^+$.

Example 15
(4aR,5R,6R,7R)-6-Cyclohexylcarbonyloxy-7-hydroxy-4a,5,6,7-tetrahydro-1,3,4a,5-tetramethylbenz[f]indol-2(4H)-one The procedure of Example 3 was repeated, except that the compound (100 mg=0.26 mmol) prepared in Example 11 was dissolved in methylene chloride (3 ml), cyclohexanecarbonyl chloride (80 μl=0.60 mmol) was added to the solution in the presence of pyridine (80 μl=0.99 mmol), and the mixture was stirred at room temperature for 4 hr. Thus, a corresponding cyclohexylcarbonyl compound (62 mg, 48%) was prepared.

The procedure of Example 12 was repeated, except that the compound (60 mg=0.12 mmol) prepared just above was dissolved in THF (2 ml), a 1 M tetrabutylammonium fluoride/THF solution (0.30 ml=0.30 mmol) was added thereto, and the mixture was stirred at room temperature for one hr. After the purification by preparative TLC, the title compound (31 mg, 66%) was obtained.

$^1$H NMR (CDCl$_3$) δ 1.21–1.86 (10H, m, OCOC$_6$H$_{11}$), 1.10 (3H, d, J=7.2 Hz, 5-CH$_3$), 1.11 (3H, s, 4a-CH$_3$), 1.89 (3H, d, J=1.7 Hz, 3-CH$_3$), 2.31 (1H, m, OCOC$_6$H$_{11}$), 2.16 (1H, dq, J=7.2, 2.8 Hz, 5-H), 2.16 (1H, br d, J=15.4 Hz, 4-H), 2.82 (1H, d, J=15.4 Hz, 4-H), 3.12 (3H, s, N—CH$_3$), 4.09 (1H, dd, J=4.5, 1.2 Hz, 7-H), 4.95 (1H, m, 6-H), 5.75 (1H, s, 9-H), 5.77 (1H, d, J=4.5 Hz, 8-H); MS (TSP) m/z 386 (M+H)$^+$.

Example 16
(4aR,5R,6R,7R)-6-Benzoyloxy-7-hydroxy-4a,5,6,7-tetrahydro-1,3,4a,5-tetramethylbenz[f]indol-2(4H)-one The procedure of Example 3 was repeated, except that the compound (30 mg=0.08 mmol) prepared in Example 11 was dissolved in methylene chloride (1.5 ml), benzoyl chloride (45 μl=0.39 mmol) was added to the solution in the presence of pyridine (62 μl=0.77 mmol), and the mixture was stirred at room temperature for 17 hr. Thus, a corresponding benzoyl compound (16 mg, 41%) was prepared.

The procedure of Example 12 was repeated, except that the compound (16 mg=0.03 mmol) prepared above was dissolved in THF (1 ml), a 1 M tetrabutylammonium fluoride/THF solution (50 μl=0.05 mmol) was added thereto, and the mixture was stirred at room temperature for 30 min. Thus, the title compound (4 mg, 34%) was prepared.

$^1$H NMR (CDCl$_3$) δ 1.20 (3H, d, J=7.1 Hz, 5-CH$_3$), 1.25 (3H, s, 4a-CH$_3$), 1.91 (3H, d, J=1.9 Hz, 3-CH$_3$), 2.23 (1H, br d, J=16.0 Hz, 4-H), 2.29 (1H, dq, J=7.1, 3.1 Hz, 5-H), 2.88 (1H, d, J=16.0 Hz, 4-H), 3.13 (3H, s, N—CH$_3$), 4.31 (1H, dd, J=4.4, 1.2 Hz, 7-H), 5.22 (1H, m,6-H), 5.78 (1H, s, 9-H), 5.81 (1H, d, J=4.4 Hz, 8-H), 7.43–8.01 (5H, m, OCOC$_6$H$_5$); MS (FAB) m/z 380 (M+H)$^+$.

Example 17
(4aR,5R,6R,7R)-6-(2-Furancarbonyloxy)-7-hydroxy-4a,5,6,7-tetrahydro-1,3,4a,5-tetramethylbenz[f]indol-2(4H)-one The procedure of Example 3 was repeated, except that the compound (25 mg=0.06 mmol) prepared in Example 11 was dissolved in methylene chloride (1 ml), 2-furoyl chloride (32 μl=0.32 mmol) was added to the solution in the presence of pyridine (52 μl=0.64 mmol), and the mixture was stirred at room temperature for 17 hr. Thus, a 2-furoyl compound (23 mg, 77%) was prepared.

The procedure of Example 12 was repeated, except that the compound (15 mg=0.03 mmol) prepared just above was dissolved in THF (1.5 ml), a 1 M tetrabutylammonium fluoride/THF solution (50 μl=0.05 mmol) was added to the solution, and the mixture was stirred at room temperature for 30 min. Thus, the title compound (5 mg, 41%) was prepared.

$^1$H NMR (CDCl$_3$) δ 1.17 (3H, d, J=7.2 Hz, 5-CH$_3$), 1.22 (3H, s, 4a-CH$_3$), 1.90 (3H, d, J=2.0 Hz, 3-CH$_3$), 2.21 (1H, br d, J=16.0 Hz, 4-H), 2.36 (1H, dq, J=7.2, 2.9 Hz, 5-H), 2.86 (1H, d, J=16.0 Hz, 4-H), 3.13 (3H, s, N—CH$_3$), 4.29 (1H, m, 7-H), 5.17 (1H, m, 6-H), 5.77 (1H, s, 9-H), 5.80 (1H, d, J=4.9 Hz, 8-H), 6.51 (1H, dd, J=3.5, 1.6 Hz, OCOC$_4$H$_3$O), 7.13 (1H, dd, J=3.5, 0.7 Hz, OCOC$_4$H$_3$O), 7.59 (1H, dd, J=1.6, 0.7 Hz, OCOC$_4$H$_3$O); MS (FAB) m/z 370 (M+H)$^+$.

Example 18
(4aR,5R,6R,7R)-6-Butoxy-7-hydroxy-4a,5,6,7-tetrahydro-1,3,4a,5-tetramethylbenz[f]indol-2(4H)-one The procedure of Example 14 was repeated, except that the compound (20 mg=0.05 mmol) prepared in Example 37 was dissolved in acetonitrile (0.4 ml), a 1 N hydrochloric acid (0.20 ml=0.20 mmol) was added to the solution, and a mixture was stirred at room temperature for 30 min. Thus, the title compound (13 mg, 68%) was prepared.

$^1$H NMR (CDCl$_3$) δ 0.88 (3H, t, J=7.2 Hz, OCH$_2$CH$_2$CH$_2$CH$_3$), 1.05 (3H, s, 4a-CH$_3$), 1.14 (3H, d, J=7.1 Hz, 5-CH$_3$), 1.34 (2H, m, OCH$_2$CH$_2$CH$_2$CH$_3$), 1.50 (2H, m, OCH$_2$CH$_2$CH$_2$CH$_3$), 1.85 (3H, d, J=1.9 Hz, 3-CH$_3$), 1.88 (1H, dq, J=7.1, 2.8 Hz, 5-H), 1.99 (1H, br d, J=15.9 Hz, 4-H), 2.77 (1H, d, J=15.9 Hz, 4-H), 3.08 (3H, s, N—CH$_3$), 3.35 (1H, dt, J=9.2, 7.2 Hz, OCH$_2$CH$_2$CH$_2$CH$_3$), 3.35 (1H, m, 6-H), 3.62 (1H, dt, J=9.2, 7.2 Hz, OCH$_2$CH$_2$CH$_2$CH$_3$), 4.19 (1H, br s, 7-H), 5.69 (1H, s, 9-H), 5.78 (1H, d, J=4.7 Hz, 8-H); MS (EI) m/z 331 (M)$^+$; [α]$^{20}_D$ −168° (c 1.0, MeOH).

Example 19
(4aR,5R,6R,7R)-7-Hydroxy-6-(3-methylbutoxy)-4a,5,6,7-tetrahydro-1,3,4a,5-tetramethylbenz[f]indol-2(4H)-one The procedure of Example 14 was repeated, except that the compound (35 mg=0.10 mmol) prepared in Example 38 was dissolved in acetonitrile (0.7 ml), a 1 N hydrochloric acid (0.35 ml=0.35 mmol) was added to the solution, and the mixture was stirred at room temperature for 30 min. Thus, the title compound (22 mg, 65%) was prepared.

$^1$H NMR (CDCl$_3$) δ 0.85 (3H, d, J=6.6 Hz, OCH$_2$CH$_2$CH(CH$_3$)$_2$), 0.86 (3H, d, J=6.6 Hz, OCH$_2$CH$_2$CH(CH$_3$)$_2$), 1.03 (3H, s, 4a-CH$_3$), 1.13 (3H, d, J=7.1 Hz, 5-CH$_3$), 1.40 (2H, m, OCH$_2$CH$_2$CH(CH$_3$)$_2$), 1.66 (1H, m, OCH$_2$CH$_2$CH(CH$_3$)$_2$), 1.83 (3H, d, J=1.9 Hz, 3-CH$_3$), 1.87 (1H, dq, J=7.1, 2.8 Hz, 5-H), 1.96 (1H, br d, J=15.9 Hz, 4-H), 2.75 (1H, d, J=15.9 Hz, 4-H), 3.07 (3H, s, N—CH$_3$), 3.35 (1H, m, 6-H), 3.36 (1H, dt, J=9.3, 6.6 Hz, OCH$_2$CH$_2$CH(CH$_3$)$_2$), 3.63 (1H, dt, J=9.3, 6.6 Hz, OCH$_2$CH$_2$CH(CH$_3$)$_2$), 4.19 (1H, br s, 7-H), 5.68 (1H, s, 9-H), 5.77 (1H, d, J=4.7 Hz, 8-H); MS (EI) m/z 345 (M)$^+$; [α]$^{20}_D$ −102° (c 0.7, MeOH).

Example 20
(4aR,5R,6R,7R)-6-Cyclopropylmethoxy-7-hydroxy-4a,5,6,7-tetrahydro-1,3,4a,5-tetramethylbenz[f]indol-2(4H)-one The procedure of Example 14 was repeated, except that the compound (15 mg=0.04 mmol) prepared in Example 40 was dissolved in acetonitrile (0.3 ml), a 1 N hydrochloric acid (0.15 ml=0.15 mmol) was added to the solution, and the mixture was stirred at room temperature for 30 min. Thus, the title compound (7 mg, 49%) was prepared.

$^1$H NMR (CDCl$_3$) δ 0.19–0.47 (4H, m, OCH$_2$C$_3$H$_5$), 1.01 (1H, m, OCH$_2$C$_3$H$_5$), 1.08 (3H, s, 4a-CH$_3$), 1.16 (3H, d, J=7.1 Hz, 5-CH$_3$), 1.86 (3H, d, J=1.9 Hz, 3-CH$_3$), 1.89 (1H, dq, J=7.1, 2.8 Hz, 5-H), 2.03 (1H, br d, J=15.9 Hz, 4-H), 2.78 (1H, d, J=15.9 Hz, 4-H), 3.09 (3H, s, N—CH$_3$), 3.29 (1H, dd, J=10.3, 6.5 Hz, OCH$_2$C$_3$H$_5$), 3.42 (1H, m, 6-H), 3.46 (1H, dd, J=10.3, 6.5 Hz, OCH$_2$C$_3$H$_5$), 4.20 (1H, br s, 7-H), 5.70 (1H, s, 9-H), 5.79 (1H, d, J=4.7 Hz, 8-H); MS (EI) m/z 329 (M)$^+$; [α]$^{20}_D$ –149° (c 1.0, MeOH).

Example 21

(4aR,5R,6R,7R)-7-Hydroxy-6-(2-propenyloxy)-4a,5,6,7-tetrahydro-1,3,4a,5-tetramethylbenz[f]indol-2(4H)-one The procedure of Example 14 was repeated, except that the compound (20 mg=0.06 mmol) prepared in Example 41 was dissolved in acetonitrile (0.4 ml), 1 N hydrochloric acid (0.20 ml=0.20 mmol) was added to the solution, and the mixture was stirred at room temperature for 30 min. Thus, the title compound (16 mg, 85%) was prepared.

$^1$H NMR (CDCl$_3$) δ 1.07 (3H, s, 4a-CH$_3$), 1.15 (3H, d, J=7.1 Hz, 5-CH$_3$), 1.84 (3H, d, J=1.9 Hz, 3-CH$_3$), 1.90 (1H, dq, J=7.1, 2.8 Hz, 5-H), 1.99 (1H, br d, J=15.9 Hz, 4-H), 2.73 (1H, d, J=15.9 Hz, 4-H), 3.08 (3H, s, N—CH$_3$), 3.45 (1H, m, 6-H), 3.95 (1H, ddt, J=13.1, 5.5, 1.5 Hz, OCH$_2$CHCH$_2$), 4.15 (1H, ddt, J=13.1, 5.5, 1.5 Hz, OCH$_2$CHCH$_2$), 4.20 (1H, br s, 7-H), 5.12 (1H, ddt, J=17.2, 10.4, 1.5 Hz, OCH$_2$CHCH$_2$), 5.23 (1H, ddt, J=17.2, 10.4, 1.5 Hz, OCH$_2$CHCH$_2$), 5.69 (1H, s, 9-H), 5.78 (1H, d, J=4.7 Hz, 8-H), 5.88 (1H, ddt, J=17.2, 10.4, 5.5 Hz, OCH$_2$CHCH$_2$); MS (EI) m/z 315 (M)$^+$; [α]$^{20}_D$ –224° (c 1.0, MeOH).

Example 22

(4aR,5R,6R,7R)-7-Hydroxy-6-propylcarbamoyloxy-4a,5,6,7-tetrahydro-1,3,4a,5-tetramethylbenz[f]indol-2(4H)-one The procedure of Example 6 was repeated, except that the compound (34 mg=0.08 mmol) prepared in Example 5 was dissolved in toluene (1 ml), propylamine (33 μl=0.40 mmol) was added to the solution, and the mixture was stirred at room temperature for 3.5 hr. Thus, a corresponding propylcarbamoyl compound was prepared (20 mg, 61%).

This compound (20 mg=0.05 mmol) was dissolved in a solution of 1,4-dioxane (0.5 ml) in water (0.2 ml), a 1 N aqueous sodium hydroxide solution (49 μl=0.05 mmol) was added to the solution, and the mixture was stirred at room temperature for 15 hr. Ethyl acetate was added to the reaction mixture, the mixture was washed with water, and the organic phase was dried over sodium sulfate. The solvent was removed under reduced pressure, and the residue was purified by column chromatography on silica gel to give the title compound (14 mg, 82%).

$^1$H NMR (CDCl$_3$) δ 0.92 (3H, t, J=7.3 Hz, OCONHCH$_2$CH$_2$CH$_3$), 1.04 (3H, s, 4a-CH$_3$), 1.12 (3H, d, J=7.0 Hz, 5-CH$_3$), 1.53 (2H, seq, J=7.3 Hz, OCONHCH$_2$CH$_2$CH$_3$), 1.88 (3H, d, J=1.6 Hz, 3-CH$_3$), 2.14 (1H, dq, J=7.0, 2.8 Hz, 5-H), 2.15 (1H, br d, J=16.3 Hz, 4-H), 2.80 (1H, d, J=16.3 Hz, 4-H), 3.10 (3H, s, N—CH$_3$), 3.15 (2H, br dt, J=7.3 Hz, OCONHCH$_2$CH$_2$CH$_3$), 4.21 (1H, m, 7-H), 4.83 (2H, m, 6-H, OCONHCH$_2$CH$_2$CH$_3$), 5.74 (1H, s, 9-H), 5.78 (1H, d, J=4.5 Hz, 8-H); MS (TSP) m/z 361 (M+H)$^+$.

Example 23

(4aR,5R,6R,7R)-7-Hydroxy-6-(pyrrolidin-1-ylcarbonyloxy)-4a,5,6,7-tetrahydro-1,3,4a,5-tetramethylbenz[f]indol-2(4H)-one The procedure of Example 22 was repeated, except that the compound (15 mg=0.04 mmol) prepared in Example 6 was dissolved in a solution of 1,4-dioxane (0.5 ml) in water (0.2 ml), a 1 N aqueous sodium hydroxide solution (36 μl=0.04 mmol) was added thereto, and the mixture was stirred at room temperature for 15 hr. Thus, the title compound (12 mg, 92%) was prepared.

$^1$H NMR (CDCl$_3$) δ 1.09 (3H, s, 4a-CH$_3$), 1.15 (3H, d, J=7.1 Hz, 5-CH$_3$), 1.85–1.89 (4H, m, OCOC$_4$H$_8$N), 1.90 (3H, d, J=1.9 Hz, 3-CH$_3$), 2.18 (1H, dq, J=7.1, 3.3 Hz, 5-H), 2.19 (1H, br d, J=16.6 Hz, 4-H), 2.81 (1H, d, J=16.6 Hz, 4-H), 3.12 (3H, s, N—CH$_3$), 3.19–3.51 (4H, m, OCOC$_4$H$_8$N), 4.27 (1H, br d, J=4.5 Hz, 7-H), 4.80 (1H, m, 6-H), 5.75 (1H, s, 9-H), 5.78 (1H, d, J=4.5 Hz, 8-H); MS (TSP) m/z 373 (M+H)$^+$.

Example 24

(4aR,5R,6R,7R)-6-Hydroxy-7-methoxy-4a,5,6,7-tetrahydro-1,3,4a,5-tetramethylbenz[f]indol-2(4H)-one Methanol (10 ml) was added to the compound (100 mg=0.32 mmol) prepared in Example 2, and the mixture was stirred at 5° C. for 3 hr. The solvent was removed under reduced pressure, and the residue was purified by preparative TLC to give the title compound (90 mg, 100%).

$^1$H NMR (CDCl$_3$) δ 1.11 (3H, s, 4a-CH$_3$), 1.19 (3H, d, J=7.3 Hz, 5-CH$_3$), 1.86 (3H, d, J=2.0 Hz, 3-CH$_3$), 1.91 (1H, dq, J=7.3, 2.6 Hz, 5-H), 2.13 (1H, br d, J=16.0 Hz, 4-H), 2.78 (1H, d, J=16.0 Hz, 4-H), 3.09 (3H, s, N—CH$_3$), 3.43 (3H, s, O—CH$_3$), 3.70 (1H, dd, J=4.8, 1.9 Hz, 7-H), 3.91 (1H, br s, 6-H), 5.74 (1H, s, 9-H), 5.82 (1H, d, J=4.8 Hz, 8-H); MS (EI) m/z 289 (M)$^+$; [α]$^{18}_D$ –584° (c 0.8, MeOH); mp 165–170° C.

Example 25

(4aR,5R,6R,7R)-6-Acetoxy-7-methoxy-4a,5,6,7-tetrahydro-1,3,4a,5-tetramethylbenz[f]indol-2(4H)-one The compound (20 mg=0.07 mmol) prepared in Example 24 was dissolved in pyridine (1 ml), acetyl chloride (15 μl=0.21 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (12 mg, 53%).

$^1$H NMR (CDCl$_3$) δ 1.08 (3H, s, 4a-CH$_3$), 1.08 (3H, d, J=7.2 Hz, 5-CH$_3$), 1.86 (3H, d, J=1.9 Hz, 3-CH$_3$), 2.06 (3H, s, OCOCH$_3$), 2.08 (1H, dq, J=7.2, 2.8 Hz, 5-H), 2.12 (1H, br d, J=15.9 Hz, 4-H), 2.79 (1H, d, J=15.9 Hz, 4-H), 3.09 (3H, s,N—CH$_3$),3.49 (3H, s, O—CH$_3$), 3.60 (1H, dd, J=4.8, 1.3 Hz, 7-H), 5.08 (1H, m, 6-H), 5.72 (1H, s, 9-H), 5.74 (1H, d, J=4.8 Hz, 8-H); MS (EI) m/z 331 (M)$^+$; [α]$^{18}_D$ –291° (c 1.0, MeOH).

Example 26

(4aR,5R,6R,7R)-7-Methoxy-6-propionyloxy-4a,5,6,7-tetrahydro-1,3,4a,5-tetramethylbenz[f]indol-2(4H)-one The compound (14 mg=0.05 mmol) prepared in Example 24 was dissolved in pyridine (1 ml), propionyl chloride (7.4 μl=0.12 mmol) was added to the solution, and the mixture was stirred at room temperature for 18 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (5 mg, 30%).

¹H NMR (CDCl₃) δ 1.08 (3H, d, J=7.2 Hz, 5-CH₃), 1.09 (3H, s, 4a-CH₃), 1.14 (3H, t, J=7.5 Hz, OCOCH₂CH₃), 1.87 (3H, d, J=1.9 Hz, 3-CH₃), 2.08 (1H, dq, J=7.2, 2.8 Hz, 5-H), 2.13 (1H, br d, J=15.9 Hz, 4-H), 2.34 (2H, q, J=7.5 Hz, OCOCH₂CH₃), 2.79 (1H, d, J=15.9 Hz, 4-H), 3.10 (3H, s, N—CH₃), 3.50 (3H, s, O—CH₃), 3.60 (1H, dd, J=4.8, 1.3 Hz, 7-H), 5.09 (1H, m, 6-H), 5.73 (1H, s, 9-H), 5.75 (1H, d, J=4.8 Hz, 8-H); MS (FAB)m/z 346 (M+H)⁺; [α]$_D^{18}$ −280° (c 0.6, MeOH).

Example 27

(4aR,5R,6R,7R)-6-Cyclopropylcarbonyloxy-7-methoxy-4a, 5,6,7-tetrahydro-1,3,4a,5-tetramethylbenz[f]indol-2(4H)-one The compound (28 mg=0.10 mmol) prepared in Example 24 was dissolved in pyridine (1 ml), cyclopropylcarbonyl chloride (27 μl=0.29 mmol) was added to the solution, and the mixture was stirred at room temperature for 15 hr. Methylene chloride (20 ml) was added to the reaction mixture. The mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (35 mg, 100%).

¹H NMR (CDCl₃) δ 0.83–1.04 (4H, m, OCOC₃H₅), 1.09 (3H, d, J=7.2 Hz, 5-CH₃), 1.10 (3H, s, 4a-CH₃), 1.57 (1H, m, OCOC₃H₅), 1.87 (3H, d, J=1.9 Hz, 3-CH₃), 2.07 (1H, dq, J=7.2, 2.8 Hz, 5-H), 2.14 (1H, br d, J=15.9 Hz, 4-H), 2.80 (1H, d, J=15.9 Hz, 4-H), 3.09 (3H, s, N—CH₃), 3.49 (3H, s, O—CH₃), 3.60 (1H, dd, J=4.7, 1.3 Hz, 7-H), 5.07 (1H, m, 6-H), 5.73 (1H, s, 9-H), 5.75 (1H, d, J=4.7 Hz, 8-H); MS (EI) m/z 357 (M)⁺; [α]$_D^{20}$ −196° (c 1.0, MeOH).

Example 28

(4aR, 5R, 6R, 7R)-6-Benzoyloxy-7-methoxy-4a, 5, 6, 7-tetrahydro-1,3,4a,5-tetramethylbenz[f]indol-2(4H)-one The compound (28 mg=0.10 mmol) prepared in Example 24 was dissolved in pyridine (1 ml), benzoyl chloride (34 μl=0.29 mmol) was added to the solution, and the mixture was stirred at room temperature for 20 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (33 mg, 87%).

¹H NMR (CDCl₃) δ 1.17 (3H, d, J=7.2 Hz, 5-CH₃), 1.25 (3H, s, 4a-CH₃), 1.89 (3H, d, J=1.9 Hz, 3-CH₃), 2.20 (1H, br d, J=15.9 Hz, 4-H), 2.21 (1H, dq, J=7.2, 2.8 Hz, 5-H), 2.85 (1H, d, J=15.9 Hz, 4-H), 3.11 (3H, s, N—CH₃), 3.57 (3H, s, O—CH₃), 3.75 (1H, dd, J=4.7, 1.3 Hz, 7-H), 5.36 (1H, m, 6-H), 5.76 (1H, s, 9-H), 5.79 (1H, d, J=4.7 Hz, 8-H), 7.40–8.00 (5H, m, OCOC₆H₅); MS (FAB) m/z 394 (M+H)⁺; [α]$_D^{20}$ +12° (c 1.0, MeOH)

Example 29

(4aR,5R,6R,7R)-7-Methoxy-6-(4-methoxy)benzoyloxy-4a, 5,6,7-tetrahydro-1,3,4a,5-tetramethylbenz[f]indol-2(4H)-one The compound (28 mg=0.10 mmol) prepared in Example 24 was dissolved in pyridine (1 ml), 4-methoxybenzoyl chloride (50 mg=0.29 mmol) was added to the solution, and the mixture was stirred at room temperature for 22 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (35 mg, 85%).

¹H NMR (CDCl₃) δ 1.15 (3H, d, J=7.2 Hz, 5-CH₃), 1.24 (3H, s, 4a-CH₃), 1.88 (3H, d, J=1.9 Hz, 3-CH₃), 2.19 (1H, br d, J=15.9 Hz, 4-H), 2.19 (1H, dq, J=7.2, 2.8 Hz, 5-H), 2.84 (1H, d, J=15.9 Hz, 4-H), 3.11 (3H, s, N—CH₃), 3.57 (3H, s, O—CH₃), 3.74 (1H, dd, J=4.7, 1.3 Hz, 7-H), 3.84 (3H, s, OCOC₆H₄—OCH₃), 5.33 (1H, m, 6-H), 5.76 (1H, s, 9-H), 5.78 (1H, d, J=4.7 Hz, 8-H), 6.91 (2H, d, J=8.7 Hz, OCOC₆H₄—OCH₃), 7.93 (2H, d, J=8.7 Hz, OCOC₆H₄—OCH₃); MS (FAB) m/z 424 (M+H)⁺; [α]$_D^{20}$ +95° (c 1.0, MeOH).

Example 30

(4aR,5R,6R,7R)-7-Methoxy-6-(4-nitro)benzoyloxy-4a,5,6, 7-tetrahydro-1,3,4a,5-tetramethylbenz[f]indol-2(4H)-one The compound (28 mg=0.10 mmol) prepared in Example 24 was dissolved in pyridine (1 ml), 4-nitrobenzoyl chloride (54 mg=0.29 mmol) was added to the solution, and the mixture was stirred at room temperature for 18 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure, and the organic phase was dried over sodium sulfate. The solvent was removed under reduced pressure, and the residue was purified by preparative TLC to give the title compound (37 mg, 87%).

¹H NMR (CDCl₃) δ 1.17 (3H, d, J=7.2 Hz, 5-CH₃), 1.23 (3H, s, 4a-CH₃), 1.89 (3H, d, J=1.9 Hz, 3-CH₃), 2.21 (1H, br d, J=15.9 Hz, 4-H), 2.25 (1H, dq, J=7.2, 2.8 Hz, 5-H), 2.85 (1H, d, J=15.9 Hz, 4-H), 3.12 (3H, s, N—CH₃), 3.57 (3H, s, O—CH₃), 3.76 (1H, dd, J=4.7, 1.3 Hz, 7-H), 5.39 (1H, m, 6-H), 5.76 (1H, s, 9-H), 5.79 (1H, d, J=4.7 Hz, 8-H), 8.14 (2H, d, J=9.0 Hz, OCOC₆H₄—NO₂), 8.29 (2H, d, J=9.0 Hz, OCOC₆H₄—NO₂); MS (FAB) m/z 439 (M+H)⁺; [α]$_D^{20}$ +80° (c 1.0, MeOH).

Example 31

(4aR,5R,6R,7R)-7-Methoxy-4a,5,6,7-tetrahydro-1,3,4a,5-tetramethyl-6-(2-thiophenecarbonyloxy)benz[f]indol-2(4H)-one The compound (17 mg=0.06 mmol) prepared in Example 24 was dissolved in pyridine (1 ml), 2-thenoyl chloride (19 μl=0.18 mmol) was added thereto, and the mixture was stirred at room temperature for 18 hr. Methylene chloride (20 ml) was added to the reaction mixture, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (21 mg, 89%).

¹H NMR (CDCl₃) δ 1.16 (3H, d, J=7.2 Hz, 5-CH₃), 1.22 (3H, 5, 4a-CH₃), 1.88 (3H, d, J=1.9 Hz, 3-CH₃), 2.17 (1H, dq, J=7.2, 2.8 Hz, 5-H), 2.18 (1H, br d, J=15.9 Hz, 4-H), 2.83 (1H, d, J=15.9 Hz, 4-H), 3.10 (3H, s, N—CH₃), 3.55 (3H, s, O—CH₃), 3.76 (1H, br d, J=4.8 Hz, 7-H), 5.27 (1H, m, 6-H), 5.75 (1H, s, 9-H), 5.77 (1H, d, J=4.8 Hz, 8-H), 7.10 (1H, dd, J=4.9, 3.8 Hz, OCOC₄H₃S), 7.55 (1H, dd, J=4.9, 1.3 Hz, OCOC₄H₃S), 7.77 (1H, dd, J=3.8, 1.3 Hz, OCOC₄H₃S); MS (EI)m/z 399 (M)⁺; [α]$_D^{18}$ +36° (c 1.0, MeOH); mp 148–153° C.

Example 32
(4aR,5R,6R,7R)-6-(2-Furancarbonyloxy)-7-methoxy-4a,5, 6,7-tetrahydro-1,3,4a,5-tetramethylbenz[f]indol-2(4H)-one The compound (12 mg=0.04 mmol) prepared in Example 24 was dissolved in pyridine (1 ml), 2-furoyl chloride (11 μl=0.12 mmol) was added to the solution, and the mixture was stirred at room temperature for 6 hr. Methylene chloride (20 ml) was added to the reaction solution, and the mixture was washed with a saturated aqueous sodium hydrogencarbonate solution (20 ml×2) and saturated saline (20 ml). The solvent was removed under reduced pressure. The organic phase was dried over sodium sulfate, and the solvent was removed under reduced pressure. The residue was purified by preparative TLC to give the title compound (12 mg, 75%).

$^1$H NMR (CDCl$_3$) δ 1.15 (3H, d, J=7.2 Hz, 5-CH$_3$), 1.21 (3H, s, 4a-CH$_3$), 1.88 (3H, d, J=1.9 Hz, 3-CH$_3$), 2.17 (1H, dq, J=7.2, 2.8 Hz, 5-H), 2.17 (1H, br d, J=15.9 Hz, 4-H), 2.83 (1H, d, J=15.9 Hz, 4-H), 3.10 (3H, s, N—CH$_3$), 3.54 (3H, s, O—CH$_3$), 3.73 (1H, dd, J=4.8, 1.3 Hz, 7-H), 5.30 (1H, m, 6-H), 5.75 (1H, s, 9-H), 5.77 (1H, d, J=4.8 Hz, 8-H), 6.49 (1H, dd, J=3.5, 1.7 Hz, OCOC$_4$H$_3$O), 7.10 (1H, dd, J=3.5, 0.8 Hz, OCOC$_4$H$_3$O), 7.57 (1H, dd, J=1.7, 0.8 Hz, OCOC$_4$H$_3$O); MS (FAB) m/z 384 (M+H)$^+$; [α]$^{18}_D$ 0° (c 1.0, MeOH); mp 155–158° C.

Example 33
(4aR,5R,6R,7R)-7-Methoxy-6-(3-pyridinecarbonyloxy)-4a, 5,6,7-tetrahydro-1,3,4a,5-tetramethylbenz[f]indol-2(4H)-one The procedure of Example 3 was repeated, except that the compound (30 mg=0.10 mmol) prepared in Example 24 was dissolved in pyridine (0.5 ml), nicotinoyl chloride hydrochloride (56 mg 0.31 mmol) was added to the solution, and the mixture was stirred at 5° C. for 20 hr. Thus, the title compound (22 mg, 54%) was prepared.

$^1$H NMR (CDCl$_3$) δ 1.17 (3H, d, J=7.1 Hz, 5-CH$_3$), 1.23 (3H, s, 4a-CH$_3$), 1.88 (3H, d, J=1.9 Hz, 3-CH$_3$), 2.20 (1H, br d, J=15.9 Hz, 4-H), 2.23 (1H, dq, J=7.1, 2.8 Hz, 5-H), 2.85 (1H, d, J=15.9 Hz, 4-H), 3.11 (3H, s, N—CH$_3$), 3.57 (3H, s, OCH$_3$), 3.76 (1H, dd, J=4.7, 1.4 Hz, 7-H), 5.38 (1H, m, 6-H), 5.75 (1H, s, 9-H), 5.78 (1H, d, J=4.7 Hz, 8-H), 7.40–8.76(4H, m, OCOC$_5$H$_4$N); MS (EI) m/z 363 (M)$^+$; [α]$^{20}_D$ -7° (c 1.0, MeOH).

Example 34
(4aR,5R,6R,7R)-6,7-Dimethoxy-4a,5,6,7-tetrahydro-1,3,4a, 5-tetramethylbenz[f]indol-2(4H)-one The compound (20 mg=0.07 mmol) prepared in Example 24 was dissolved in DMF (400 μl), and 60% sodium hydride (NaH) (14 mg=0.35 mmol) as an oil was gradually added to the solution under ice cooling. After foaming subsided, methyl iodide (22 μl=0.35 mmol) was added thereto, and the mixture was stirred at room temperature for 2 hr. Methylene chloride (20 ml) was added to the reaction mixture, and the mixture was washed with water (20 ml) and saturated saline (20 ml). The solvent was removed under reduced pressure, the organic phase was dried over sodium sulfate, and the solvent was removed under reduced pressure. The residue was purified by preparative TLC to give the title compound (13 mg, 62%).

$^1$H NMR (CDCl$_3$) δ 1.05 (3H, s, 4a-CH$_3$), 1.16 (3H, d, J=7.1 Hz, 5-CH$_3$), 1.85 (3H, d, J=2.0 Hz, 3-CH$_3$), 1.89 (1H, dq, J=7.1, 2.8 Hz, 5-H), 2.09 (1H, br d, J=15.9 Hz, 4-H), 2.77 (1H, d, J=15.9 Hz, 4-H), 3.08 (3H, s, N—CH$_3$), 3.28 (1H, m, 6-H), 3.40 (3H, s, O—CH$_3$), 3.43 (3H, s, O—CH$_3$), 3.74 (1H, dd, J=4.8, 1.4 Hz, 7-H), 5.72 (1H, s, 9-H), 5.81 (1H, d, J=4.8 Hz, 8-H); MS (EI) m/z 303 (M)$^+$; [α]$^{18}_D$ -340° (c 1.0, MeOH).

Example 35
(4aR,5R,6R,7R)-6-Ethoxy-7-methoxy-4a,5,6,7-tetrahydro-1,3,4a,5-tetramethylbenz[f]indol-2(4H)-one The compound (25 mg=0.09 mmol) prepared in Example 24 was dissolved in dimethylformamide (500 μl), and 60% sodium hydride (NaH) as an oil (18 mg=0.45 mmol) was gradually added to the solution under ice cooling. After foaming subsided, ethyl iodide (35 μl=0.45 mmol) was added thereto, and the mixture was stirred at room temperature for 2.5 hr. Methylene chloride (20 ml) was added to the reaction mixture, and the mixture was washed with water (20 ml) and saturated saline (20 ml). The solvent was removed under reduced pressure. The organic phase was dried over sodium sulfate, and the solvent was removed under reduced pressure. The residue was purified by preparative TLC to give the title compound (10 mg, 36%).

$^1$H NMR (CDCl$_3$) δ 1.06 (3H, s, 4a-CH$_3$), 1.14 (3H, d, J=7.1 Hz, 5-CH$_3$), 1.17 (3H, t, J=7.0 Hz, OCH$_2$CH$_3$), 1.85 (3H, d, J=2.0 Hz, 3-CH$_3$), 1.87 (1H, dq, J=7.1, 2.8 Hz, 5-H), 2.09 (1H, br d, J=15.9 Hz, 4-H), 2.77 (1H, d, J=15.9 Hz, 4-H), 3.08 (3H, s, N—CH$_3$), 3.38 (1H, m, 6-H), 3.42 (1H, dq, J=7.0, 2.3 Hz, OCH$_2$CH$_3$), 3.42 (3H, s, O—CH$_3$), 3.66 (1H, dq, J=7.0, 2.3 Hz, OCH$_2$CH$_3$), 3.70 (1H, dd, J=4.8, 1.4 Hz, 7-H), 5.72 (1H, s, 9-H), 5.81 (1H, d, J=4.8 Hz, 8-H); MS (EI) m/z 317 (M)$^+$; [α]$^{18}_D$ -300° (c 1.0, MeOH).

Example 36
(4aR,5R,6R,7R)-7-Methoxy-6-propoxy-4a,5,6,7-tetrahydro-1,3,4a,5-tetramethylbenz[f]indol-2(4H)-one The compound (50 mg=0.17 mmol) prepared in Example 24 was dissolved in dimethylformamide (500 μl), and 60% sodium hydride (NaH) as an oil (35 mg 0.87 mmol) was gradually added to the solution under ice cooling. After foaming subsided, n-propyl iodide (84 μl=0.87 mmol) was added thereto, and the mixture was stirred at room temperature for 4 hr. Methylene chloride (20 ml) was added to the reaction mixture, the mixture was washed with water (20 ml) and saturated saline (20 ml), and the solvent was removed under reduced pressure. The organic phase was dried over sodium sulfate, and the solvent was removed under reduced pressure. The residue was purified by preparative TLC to give the title compound (14 mg, 24%).

$^1$H NMR (CDCl$_3$) δ 0.91 (3H, t, J=6.4 Hz, OCH$_2$CH$_2$CH$_3$), 1.07 (3H, s, 4a-CH$_3$), 1.14 (3H, d, J=7.1 Hz, 5-CH$_3$), 1.55 (2H, seq, J=6.4 Hz, OCH$_2$CH$_2$CH$_3$), 1.85 (3H, d, J=2.0 Hz, 3-CH$_3$), 1.87 (1H, dq, J=7.1, 2.8 Hz, 5-H), 2.09 (1H, br d, J=15.9 Hz, 4-H), 2.77 (1H, d, J=15.9 Hz, 4-H), 3.08 (3H, s, N—CH$_3$), 3.30 (1H, dt, J=9.0, 6.4 Hz, OCH$_2$CH$_2$CH$_3$), 3.37 (1H, m, 6-H), 3.42 (3H, s, OCH$_3$), 3.57 (1H, dt, J=9.0, 6.4 Hz, OCH$_2$CH$_2$CH$_3$), 3.70 (1H, dd, J=4.8, 1.4 Hz, 7-H), 5.72 (1H, s, 9-H), 5.80 (1H, d, J=4.8 Hz, 8-H); MS (EI) m/z 331 (M)$^+$; [α]$^{18}_D$ -309° (c 1.0, MeOH).

Example 37
(4aR,5R,6R,7R)-6-Butoxy-7-methoxy-4a,5,6,7-tetrahydro-1,3,4a,5-tetramethylbenz[f]indol-2(4H)-one The procedure of Example 34 was repeated, except that the compound (10 mg=0.03 mmol) prepared in Example 24 was dissolved in DMF (1 ml), 60% sodium hydride (4 mg=0.10 mmol) as an oil and butyl iodide (24 μl=0.21 mmol) were added to the solution, and the mixture was stirred at room temperature for 3 hr. Thus, the title compound (4 mg, 31%) was prepared.

$^1$H NMR (CDCl$_3$) δ 0.91 (3H, t, J=7.3 Hz, OCH$_2$CH$_2$CH$_2$CH$_3$), 1.08 (3H, s, 4a-CH$_3$), 1.16 (3H, d, J=7.2 Hz, 5-CH$_3$), 1.38 (2H, m, OCH$_2$CH$_2$CH$_2$CH$_3$), 1.54 (2H, m, OCH$_2$CH$_2$CH$_2$CH$_3$), 1.87 (3H, d, J=2.0 Hz, 3-CH$_3$), 1.89 (1H, dq, J=7.2, 2.7 Hz, 5-H), 2.11 (1H, br d, J=15.9 Hz,

4-H), 2.78 (1H, d, J=15.9 Hz, 4-H), 3.10 (3H, s, N—CH$_3$), 3.36 (1H, dt, J=9.0, 6.3 Hz, OCH$_2$CH$_2$CH$_2$CH$_3$), 3.38 (1H, m, 6-H), 3.44 (3H, s, OCH$_3$), 3.62 (1H, dt, J=9.0, 6.3 Hz, OCH$_2$CH$_2$CH$_2$CH$_3$), 3.72 (1H, br d, J=4.4 Hz, 7-H), 5.74 (1H, s, 9-H), 5.82 (1H, d, J=4.4 Hz, 8-H); MS (TSP) m/z 346 (M+H)$^+$.

Example 38
(4aR,5R,6R,7R)-7-Methoxy-6-(3-methylbutoxy)-4a,5,6,7-tetrahydro-1,3,4a,5-tetramethylbenz[f]indol-2(4H)-one The procedure of Example 34 was repeated, except that the compound (30 mg=0.10 mmol) prepared in Example 24 was dissolved in DMF (0.2 ml), 60% sodium hydride as an oil (13 mg=0.31 mmol) and isoamyl iodide (82 μl=0.62 mmol) were added to the solution, and the mixture was stirred at 50° C. for 3 hr. Thus, the title compound (7 mg, 19%) was prepared.

$^1$H NMR (CDCl$_3$) δ 0.88 (3H, d, J=6.7 Hz, OCH$_2$CH$_2$CH (CH$_3$)$_2$), 0.88 (3H, d, J=6.7 Hz, OCH$_2$CH$_2$CH(CH$_3$)$_2$), 1.06 (3H, s, 4a-CH$_3$), 1.14 (3H, d, J=7.1 Hz,5-CH$_3$), 1.43 (2H, m, OCH$_2$CH$_2$CH(CH$_3$)$_2$), 1.70 (1H, m, OCH$_2$CH$_2$CH(CH$_3$)$_2$), 1.86 (3H, d, J=1.9 Hz, 3-CH$_3$), 1.87 (1H, dq, J=7.1, 2.8 Hz, 5-H), 2.09 (1H, br d, J=15.9 Hz, 4-H), 2.77 (1H, d, J=15.9 Hz, 4-H), 3.08 (3H, s, N—CH$_3$), 3.36 (1H, m, 6-H), 3.36 (1H, dt, J=9.1, 6.3 Hz, OCH$_2$CH$_2$CH(CH$_3$)$_2$), 3.43 (3H, s, OCH$_3$), 3.63 (1H, dt, J=9.1, 6.3 Hz, OCH$_2$CH$_2$CH(CH$_3$)$_2$), 3.71 (1H, dd, J=4.7, 1.4 Hz, 7-H), 5.72 (1H, s, 9-H), 5.81 (1H, d, J=4.7 Hz, 8-H); MS (EI) m/z 359 (M)$^+$; [α]$^{20}_D$ –157° (c 1.0, MeOH).

Example 39
(4aR,5R,6R,7R)-7-Methoxy-6-[(2S)-2-methylbutoxy]-4a,5,6,7-tetrahydro-1,3,4a,5-tetramethylbenz[f]indol-2(4H)-one The procedure of Example 34 was repeated, except that the compound (92 mg=0.32 mmol) prepared in Example 24 was dissolved in DMF (0.5 ml), 60% sodium hydride as an oil (39 mg=0.98 mmol) and (S)-(+)-1-iodo-2-methylbutane (0.25 ml=1.91 mmol) were added to the solution, and the mixture was stirred at 50° C. for 3 hr. Thus, the title compound (1 mg, 1%) was prepared.

$^1$H NMR (CDCl$_3$) δ 0.87 (3H, t, J=7.5 Hz, OCH$_2$CH (CH$_3$)CH$_2$CH$_3$), 0.88 (3H, d, J=7.4 Hz, OCH$_2$CH(CH$_3$) CH$_2$CH$_3$), 1.07 (3H, s, 4a-CH$_3$), 1.15 (3H, d, J=7.1 Hz, 5-CH$_3$), 1.31 (3H, m, OCH$_2$CH(CH$_3$)CH$_2$CH$_3$), 1.86 (3H, d, J=1.9 Hz, 3-CH$_3$), 1.88 (1H, dq, J=7.1, 2.8 Hz, 5-H), 2.09 (1H, br d, J=15.9 Hz, 4-H), 2.77 (1H, d, J=15.9 Hz, 4-H), 3.09 (3H, s, N—CH$_3$), 3.20 (1H, dd, J=8.7, 5.6 Hz, OCH$_2$CH(CH$_3$)CH$_2$CH$_3$), 3.35 (1H, m, 6-H), 3.42 (1H, dd, J=8.7, 5.6 Hz, OCH$_2$CH(CH$_3$),CH$_2$CH$_3$), 3.43 (3H, s, OCH$_3$), 3.70 (1H, dd, J=4.7, 1.4 Hz, 7-H), 5.73 (1H, s, 9-H), 5.80 (1H, d, J=4.7 Hz, 8-H); MS (EI) m/z 359 (M)$^+$; [α]$^{20}_D$ –35° (c 1.0, MeOH).

Example 40
(4aR,5R,6R,7R)-6-Cyclopropylmethoxy-7-methoxy-4a,5,6,7-tetrahydro-1,3,4a,5-tetramethylbenz[f]indol-2(4H)-one The procedure of Example 34 was repeated, except that the compound (52 mg=0.18 mmol) prepared in Example 24 was dissolved in DMF (0.5 ml), 60% sodium hydride as an oil (22 mg=0.54 mmol) and (bromomethyl)cyclopropane (0.10 ml=1.08 mmol) were added to the solution, and the mixture was stirred at 50° C. for 3 hr. Thus, the title compound (25 mg, 40%) was prepared.

$^1$H NMR (CDCl$_3$) δ 0.20–0.48 (4H, m, OCH$_2$C$_3$H$_5$), 1.02 (1H, m, OCH$_2$C$_3$H$_5$), 1.09 (3H, s, 4a-CH$_3$), 1.16 (3H, d, J=7.1 Hz, 5-CH$_3$), 1.86 (3H, d, J=1.9 Hz, 3-CH$_3$), 1.88 (1H, dq, J=7.1, 2.8 Hz, 5-H), 2.10 (1H, br d, J=15.9 Hz, 4-H), 2.78 (1H, d, J=15.9 Hz, 4-H), 3.09 (3H, s, N—CH$_3$), 3.27 (1H, dd, J=10.1, 6.4 Hz, OCH$_2$C$_3$H$_5$), 3.42 (3H, s, OCH$_3$), 3.43 (1H, m, 6-H), 3.46 (1H, dd, J=10.1, 6.4 Hz, OCH$_2$C$_3$H$_5$), 3.71 (1H, dd, J=4.7, 1.4 Hz, 7-H), 5.73 (1H, s, 9-H), 5.82 (1H, d, J=4.7 Hz, 8-H); MS (EI) m/z 343 (M)$^+$; [α]$^{20}_D$ –264° (c 1.0, MeOH).

Example 41
(4aR,5R,6R,7R)-7-Methoxy-6-(2-propenyloxy)-4a,5,6,7-tetrahydro-1,3,4a,5-tetramethylbenz[f]indol-2(4H)-one The compound (28 mg=0.10 mmol) prepared in Example 24 was dissolved in dimethylformamide (500 μl), 60% sodium hydride (NaH) (20 mg=0.49 mmol) as an oil was gradually added to the solution under ice cooling. After foaming subsided, allyl iodide (45 μl=0.49 mmol) was added thereto, and the mixture was stirred at room temperature for 1.5 hr. Methylene chloride (20 ml) was added to the reaction mixture, the mixture was washed with water (20 ml) and saturated saline (20 ml), and the solvent was removed under reduced pressure. The organic phase was dried over sodium sulfate, and the solvent was removed under reduced pressure. The residue was purified by preparative TLC to give the title compound (22 mg, 69%).

$^1$H NMR (CDCl$_3$) δ 1.08 (3H, s, 4a-CH$_3$), 1.15 (3H, d, J=7.1 Hz, 5-CH$_3$), 1.85 (3H, d, J=2.0 Hz, 3-CH$_3$), 1.90 (1H, dq, J=7.1, 2.8 Hz, 5-H), 2.10 (1H, br d, J=15.9 Hz, 4-H), 2.78 (1H, d, J=15.9 Hz, 4-H), 3.08 (3H, s, N—CH$_3$), 3.41 (3H, s, O—CH$_3$), 3.46 (1H, m, 6-H), 3.72 (1H, dd, J=4.8, 1.4 Hz, 7-H), 3.94 (1H, ddt, J=13.1, 5.6, 1.5 Hz, OCH$_2$CH=CH$_2$), 4.15 (1H, ddt, J=13.1, 5.6, 1.5 Hz, OCH$_2$CH=CH$_2$), 5.20 (2H, m, OCH$_2$CH=CH$_2$), 5.72 (1H, s, 9-H), 5.80 (1H, d, J=4.8 Hz, 8-H), 5.89 (1H, m, OCH$_2$CH=CH$_2$); MS (EI)m/z 329 (M)$^+$; [α]$^{18}_D$ –272° (c 1.0, MeOH).

Example 42
(4aR,5R,6R,7R)-7-Methoxy-6-[(E)-3-phenyl-2-propenyloxy]-4a,5,6,7-tetrahydro-1,3,4a,5-tetramethylbenz[f]indol-2(4H)-one The procedure of Example 34 was repeated, except that the compound (10 mg=0.03 mmol) prepared in Example 24 was dissolved in DMF(1 ml), 60% sodium hydride (4 mg=0.10 mmol) as an oil and cinnamyl bromide (31 μl=0.21 mmol), and the mixture was stirred at room temperature for 4 hr. Thus, the title compound (4 mg, 29%) was prepared.

$^1$H NMR (CDCl$_3$) δ 1.13 (3H, s, 4a-CH$_3$), 1.19 (3H, d, J=7.1 Hz, 5-CH$_3$), 1.88 (3H, d, J=1.9 Hz, 3-CH$_3$), 1.94 (1H, dq, J=7.1, 2.7 Hz, 5-H), 2.12 (1H, br d, J=16.0 Hz, 4-H), 2.80 (1H, d, J=16.0 Hz, 4-H), 3.10 (3H, s, N—CH$_3$), 3.44 (3H, s, OCH$_3$), 3.55 (1H, m, 6-H), 3.78 (1H, dd, J=4.8, 1.2 Hz, 7-H), 4.14 (1H, dd, J=13.1, 5.8 Hz, OCH$_2$CHCHC$_6$H$_5$), 4.32 (1H, dd, J=13.1, 5.8 Hz, OCH$_2$CHCHC$_6$H$_5$), 5.75 (1H, s, 9-H), 5.84 (1H, d, J=4.8 Hz, 8-H), 6.27 (1H, dt, J=15.9, 5.8 Hz, OCH$_2$CHCHC$_6$H$_5$), 6.60 (1H, d, J=15.9 Hz, OCH$_2$CHCHC$_6$H$_5$), 7.22–7.39 (5H, m, OCH$_2$CHCHC$_6$H$_5$); MS (TSP) m/z 406 (M+H)$^+$;

Example 43
(4aR,5R,6R,7R)-6-Benzyloxy-7-methoxy-4a,5,6,7-tetrahydro-1,3,4a,5-tetramethylbenz[f]indol-2(4H)-one The compound (35 mg=0.12 mmol) prepared in Example 24 was dissolved in dimethylformamide (500 μl), 60% sodium hydride (NaH) (25 mg=0.60 mmol) as an oil was gradually added to the solution under ice cooling. After foaming subsided, benzyl bromide (72 μl=0.60 mmol) was added thereto, and the mixture was stirred at room temperature for 1 hr. Methylene chloride (20 ml) was thereto, and the mixture was washed with water (20 ml) and saturated saline (20 ml), and the solvent was removed under reduced pressure. The organic phase was dried over sodium sulfate, and the solvent was removed under reduced pressure. The residue was purified by preparative TLC to give the title compound (32 mg, 70%).

$^1$H NMR (CDCl$_3$) δ 1.13 (3H, s, 4a-CH$_3$), 1.14 (3H, d, J=7.1 Hz, 5-CH$_3$), 1.86 (3H, d, J=2.0 Hz, 3-CH$_3$), 1.92 (1H, dq, J=7.1, 2.8 Hz, 5-H), 2.11 (1H, br d, J=15.9 Hz, 4-H), 2.78 (1H, d, J=15.9 Hz, 4-H), 3.09 (3H, s, N—CH$_3$), 3.40 (3H, s, O—CH$_3$), 3.55 (1H, m, 6-H), 3.78 (1H, dd, J=4.8, 1.4 Hz, 7-H), 4.51 (1H, d, J=12.0 Hz, OC$\underline{H}_2$C$_6$H$_5$), 4.69 (1H, d, J=12.0 Hz, OC$\underline{H}_2$C$_6$H$_5$), 5.72 (1H, s, 9-H), 5.80 (1H, d, J=4.8 Hz, 8-H), 7.25–7.37 (5H, m, OCH$_2$C$_6$H$_5$); MS (EI)m/z 379 (M)$^+$; [α]$^{18}_D$ −198° (c 1.0, MeOH).

Example 44

(4aR,5R,6R,7R)-7-Methoxy-6-(4-methoxybenzyloxy)-4a,5,6,7-tetrahydro-1,3,4a,5-tetramethylbenz[f]indol-2(4H)-one The procedure of Example 34 was repeated, except that the compound (10 mg=0.03 mmol) prepared in Example 24 was dissolved in DMF(1 ml), 60% sodium hydride (4 mg=0.10 mmol) as an oil and 4-methoxybenzyl chloride (28 μl=0.21 mmol) were added to the solution, and the mixture was stirred at room temperature for 5 hr. Thus, title compound (2 mg, 14%) was prepared.

$^1$H NMR (CDCl$_3$) δ 1.11 (3H, s, 4a-CH$_3$), 1.13 (3H, d, J=7.1 Hz, 5-CH$_3$), 1.87 (3H, d, J=1.7 Hz, 3-CH$_3$), 1.92 (1H, dq, J=7.1, 2.7 Hz, 5-H), 2.11 (1H, br d, J=16.0 Hz, 4-H), 2.79 (1H, d, J=16.0 Hz, 4-H), 3.10 (3H, s, N—CH$_3$), 3.41 (3H, s, OCH$_3$), 3.54 (1H, m, 6-H), 3.78 (1H, br d, J=5.0 Hz, 7-H), 3.81 (3H,s, OCH$_2$C$_6$H$_4$—OCH$_3$), 4.45 (1H, d, J=11.5 Hz, OCH$_2$C$_6$H$_4$—OCH$_3$), 4.63 (1H, d, J=11.5 Hz, OCH$_2$C$_6$H$_4$—OCH$_3$), 5.74 (1H, s, 9-H), 5.82 (1H, d, J=5.0 Hz, 8-H), 6.87 (2H, d, J=8.6 Hz, OCH$_2$C$_6$H$_4$—OCH$_3$), 7.26 (2H, d, J=8.6 Hz, OCH$_2$C$_6$H$_4$—OCH$_3$); MS (TSP) m/z 410 (M+H)$^+$.

Example 45

(4aR,5R,6R,7R)-6-(2,2-Dihydroxyethoxy)-7-methoxy-4a,5,6,7-tetrahydro-1,3,4a,5-tetramethylbenz[f]indol-2(4H)-one The compound (50 mg=0.15 mmol) prepared in Example 41 was dissolved in a solution of 1,4-dioxane (0.5 ml) in water (0.4 ml), a 4% aqueous osmium tetraoxide solution (96 μl=0.02 mmol) and sodium periodate (65 mg=0.30 mmol), and the mixture was stirred at room temperature for 30 min. Methylene chloride was added thereto, the mixture was washed with water, and the organic phase was dried over sodium sulfate. The solvent was removed under reduced pressure, and the residue was purified by preparative TLC to give the title compound (40 mg, 75%).

$^1$H NMR (CDCl$_3$) δ 1.01 (3H, s, 4a-CH$_3$), 1.14 (3H, d, J=7.1 Hz, 5-CH$_3$), 1.83 (3H, d, J=1.9 Hz, 3-CH$_3$), 1.90 (1H, dq, J=7.1, 2.8 Hz, 5-H), 2.08 (1H, br d, J=15.9 Hz, 4-H), 2.74 (1H, d, J=15.9 Hz, 4-H), 3.06 (3H, s, N—CH$_3$) 3.40 (3H, s, OCH$_3$), 3.42–3.75 (4H, m, 7-H, OCH$_2$CH(OH)$_2$), 3.43 (1H, m, 6-H), 5.71 (1H, s, 9-H), 5.78 (1H, d, J=4.7 Hz, 8-H); MS (EI) m/z 349 (M)$^+$; [α]$^{20}_D$ −390° (c 1.0, MeOH).

Example 46

(4aR,5R,6R,7R)-6-(2-Hydroxyethoxy)-7-methoxy-4a,5,6,7-tetrahydro-1,3,4a,5-tetramethylbenz[f]indol-2(4H)-one The compound (40 mg=0.12 mmol) prepared in Example 45 was dissolved in methanol (0.8 ml), sodium borohydride (9 mg=0.24 mmol) was added to the solution, and the mixture was stirred at room temperature for 5 min. Methylene chloride was added to the reaction mixture, the mixture was washed with water, and the organic phase was dried over sodium sulfate. The solvent was removed under reduced pressure, and the residue was purified by preparative TLC to give the title compound (5 mg, 12%).

$^1$H NMR (CDCl$_3$) δ 1.07 (3H, s, 4a-CH$_3$), 1.18 (3H, d, J=7.1 Hz, 5-CH$_3$), 1.86 (3H, d, J=1.9 Hz, 3-CH$_3$), 1.94 (1H, dq, J=7.1, 2.8 Hz, 5-H), 2.11 (1H, br d, J=15.9 Hz, 4-H), 2.78 (1H, d, J=15.9 Hz, 4-H), 3.09 (3H, s, N—CH$_3$), 3.43 (3H, s, OCH$_3$), 3.50–3.80 (5H, m, 7-H, OCH$_2$CH$_2$OH), 3.47 (1H, m, 6-H), 5.73 (1H, s, 9-H), 5.81 (1H, d, J=4.7 Hz, 8-H); MS (EI) m/z 333 (M)$^+$; [α]$^{20}_D$ −72° (c 0.4, MeOH).

Example 47

(4aR,5R,6R,7R)-6-(Imidazol-1-ylcarbonyloxy)-7-methoxy-4a,5,6,7-tetrahydro-1,3,4a,5-tetramethylbenz[f]indol-2(4H)-one The procedure of Example 5 was repeated, except that the compound (450 mg=1.56 mmol) prepared in Example 24 was dissolved in methylene chloride (9 ml), 1,1-carbonyldiimidazole (532 mg=3.28 mmol) was added to the solution, and the mixture was stirred at room temperature for 5 hr. Thus, the title compound (486 mg, 81%) was prepared.

$^1$H NMR (CDCl$_3$) δ 1.19 (3H, s, 4a-CH$_3$), 1.22 (3H, d, J=7.3 Hz, 5-CH$_3$), 1.91 (3H, d, J=1.9 Hz, 3-CH$_3$), 2.22 (1H, br d, J=16.0 Hz, 4-H), 2.26 (1H, dq, J=7.3, 2.8 Hz, 5-H), 2.86 (1H, d, J=16.0 Hz, 4-H), 3.13 (3H, s, N—CH$_3$), 3.57 (3H, s, OCH$_3$), 3.83 (1H, dd, J=4.7, 1.2 Hz, 7-H), 5.28 (1H, m, 6-H), 5.77 (1H, s, 9-H), 5.79 (1H, d, J=4.7 Hz, 8-H), 7.10 (1H, br s, OCOC$_3$N$_2$), 7.39 (1H, br s, OCOC$_3$N$_2$), 8.11 (1H, br s, OCOC$_3$N$_2$); MS (EI) m/z 383 (M)$^+$.

Example 48

(4aR,5R,6R,7R)-6-Carbamoyloxy-7-methoxy-4a,5,6,7-tetrahydro-1,3,4a,5-tetramethylbenz[f]indol-2(4H)-one The compound (50 mg=0.13 mmol) prepared in Example 47 was dissolved in methylene chloride (2 ml), methyl triflate (14 μl=0.12 mmol) was added to the solution, and the mixture was stirred at 10° C. for 30 min. An excess of ammonia was added to the reaction mixture, and the mixture was stirred at room temperature for 30 min. The solvent was removed under reduced pressure, and the residue was purified by column chromatography on silica gel to give the title compound (30 mg, 70%).

$^1$H NMR (CDCl$_3$) δ 1.03 (3H, s, 4a-CH$_3$), 1.14 (3H, d, J=7.2 Hz, 5-CH$_3$), 1.87 (3H, d, J=1.9 Hz, 3-CH$_3$), 2.07 (1H, dq, J=7.2, 2.7 Hz, 5-H), 2.14 (1H, br d, J=15.8 Hz, 4-H), 2.80 (1H, d, J=15.8 Hz, 4-H), 3.09 (3H, s, N—CH$_3$), 3.52 (3H, s, OCH$_3$), 3.70 (1H, dd, J=4.8, 1.5 Hz, 7-H), 4.73 (2H, m, OCONH$_2$), 4.99 (1H, m, 6-H), 5.73 (1H, s, 9-H), 5.78 (1H, d, J=4.8 Hz, 8-H); MS (FAB) m/z 333 (M+H)$^+$.

Example 49

(4aR,5R,6R,7R)-7-Methoxy-6-methylcarbamoyloxy-4a,5,6,7-tetrahydro-1,3,4a,5-tetramethylbenz[f]indol-2(4H)-one The procedure of Example 6 was repeated, except that the compound (58 mg=0.15 mmol) prepared in Example 47 was dissolved in THF (0.4 ml), a 2 M methylamine/THF solution (0.76 ml=1.52 mmol) was added to the solution, and the mixture was stirred at room temperature for 3 hr, followed by purification by preparative TLC. Thus, the title compound (52 mg, 99%) was prepared.

$^1$H NMR (CDCl$_3$) δ 0.97 (3H, s, 4a-CH$_3$), 1.10 (3H, d, J=7.1 Hz, 5-CH$_3$), 1.84 (3H, br s, 3-CH$_3$), 2.03 (1H, dq, J=7.1, 2.6 Hz, 5-H), 2.11 (1H, br d, J=16.3 Hz, 4-H), 2.77 (1H, d, J=16.3 Hz, 4-H), 2.82 (3H, d, J=4.7 Hz, OCONHCH$_3$), 3.06 (3H, s, N—CH$_3$), 3.51 (3H, s, OCH$_3$), 3.67 (1H, br d, J=4.8 Hz, 7-H), 4.97 (1H, m, 6-H), 5.11 (1H, m, OCONHCH$_3$), 5.70 (1H, s, 9-H), 5.75 (1H, d, J=4.8 Hz, 8-H); MS (FAB) m/z 347 (M+H)$^+$.

Example 50

(4aR,5R,6R,7R)-6-Ethylcarbamoyloxy-7-methoxy-4a,5,6,7-tetrahydro-1,3,4a,5-tetramethylbenz[f]indol-2(4H)-one The procedure of Example 6 was repeated, except that the compound (57 mg=0.15 mmol) prepared in Example 47 was dissolved in THF (0.4 ml), a 2 M ethylamine/THF solution (0.75 ml=1.50 mmol) was added to the solution, and the mixture was stirred at room temperature for 1.5 hr, followed by purification by preparative TLC. Thus, the title compound (53 mg, 97%) was prepared.

$^1$H NMR (CDCl$_3$) δ 1.02 (3H, s, 4a-CH$_3$), 1.12 (3H, d, J=7.1 Hz, 5-CH$_3$), 1.16 (3H, t, J=6.9 Hz, OCONHCH$_2$CH$_3$), 1.86 (3H, br s, 3-CH$_3$), 2.05 (1H, dq, J=7.1, 1.9 Hz, 5-H), 2.13 (1H, br d, J=16.0 Hz, 4-H), 2.79 (1H, d, J=16.0 Hz, 4-H), 3.08 (3H, s, N—CH$_3$), 3.25 (2H, br q, J=6.9 Hz, OCONHCH$_2$CH$_3$), 3.52 (3H, s, OCH$_3$), 3.69 (1H, br d, J=4.7 Hz, 7-H), 4.49 (1H, m, OCONHCH$_2$CH$_3$), 4.97 (1H, m, 6-H), 5.72 (1H, s, 9-H), 5.76 (1H, d, J=4.7 Hz, 8-H); MS (FAB) m/z 361 (M+H)$^+$.

Example 51

(4aR,5R,6R,7R)-7-Methoxy-6-propylcarbamoyloxy-4a,5,6,7-tetrahydro-1,3,4a,5-tetramethylbenz[f]indol-2(4H)-one The compound (30 mg=0.10 mmol) prepared in Example 24 was dissolved in DMF (0.6 ml), propyl isocyanate (0.19 ml=2.07 mmol) was added to the solution in the presence of 4-dimethylaminopyridine (258 mg=2.11 mmol), and the mixture was stirred at 80° C. for 4.5 hr. Ethyl acetate was added to the reaction mixture, the mixture was washed with water, and the organic phase was dried over sodium sulfate. The solvent was removed under reduced pressure, and the residue was purified by preparative TLC to give the title compound (34 mg, 88%).

$^1$H NMR (CDCl$_3$) δ 0.92 (3H, t, J=7.2 Hz, OCONHCH$_2$CH$_2$CH$_3$), 0.99 (3H, s, 4a-CH$_3$), 1.11 (3H, d, J=6.8 Hz, 5-CH$_3$), 1.54 (2H, seq, J=7.2 Hz, OCONHCH$_2$CH$_2$CH$_3$), 1.85 (3H, br s, 3-CH$_3$), 2.04 (1H, dq, J=6.8, 1.9 Hz, 5-H), 2.11 (1H, br d, J=16.3 Hz, 4-H), 2.77 (1H, d, J=16.3 Hz, 4-H), 3.06 (3H, s, N—CH$_3$), 3.15 (2H, br dt, J=7.2 Hz, OCONHCH$_2$CH$_2$CH$_3$), 3.51 (3H, s, OCH$_3$), 3.67 (1H, br d, J=4.9 Hz, 7-H), 4.97 (1H, m, 6-H), 5.08 (1H, m, OCONHCH$_2$CH$_2$CH$_3$), 5.71 (1H, s, 9-H), 5.75 (1H, d, J=4.9 Hz, 8-H); MS (EI) m/z 375 (M+H)$^+$.

Example 52

(4aR,5R,6R,7R)-7-Methoxy-6-(1-methylethylcarbamoyloxy)-4a,5,6,7-tetrahydro-1,3,4a,5-tetramethylbenz[f]indol-2(4H)-one The procedure of Example 6 was repeated, except that the compound (30 mg=0.08 mmol) prepared in Example 47 was dissolved in toluene (1 ml), isopropylamine (33 μl=0.39 mmol) was added to the solution, and the mixture was stirred at 6° C. for 15 hr and then at 9° C. for 4 hr. Thus, the title compound (9 mg, 31%) was prepared.

$^1$H NMR (CDCl$_3$) δ 1.07 (3H, s, 4a-CH$_3$), 1.13 (3H, d, J=7.2 Hz, 5-CH$_3$), 1.15 (3H, d, J=6.1 Hz, OCONHCH(CH$_3$)$_2$), 1.17 (3H, d, J=6.1 Hz, OCONHCH(CH$_3$)$_2$), 1.88 (3H, d, J=1.8 Hz, 3-CH$_3$), 2.07 (1H, m, 5-H), 2.14 (1H, br d, J=16.2 Hz, 4-H), 2.80 (1H, d, J=16.2 Hz, 4-H), 3.10 (3H, s, N—CH$_3$), 3.53 (3H, s, OCH$_3$), 3.69 (1H, dd, J=4.8, 1.4 Hz, 7-H), 3.82 (1H, m, OCONHCH(CH$_3$)$_2$), 4.51 (1H, m, OCONHCH(CH$_3$)$_2$), 4.97 (1H, m, 6-H), 5.74 (1H, s, 9-H), 5.77 (1H, d, J=4.8 Hz, 8-H); MS (TSP) m/z 375 (M+H)$^+$.

Example 53

(4aR,5R,6R,7R)-7-Methoxy-6-(2-methylpropylcarbamoyloxy)-4a,5,6,7-tetrahydro-1,3,4a,5-tetramethylbenz[f]indol-2(4H)-one The procedure of Example 6 was repeated, except that the compound (30 mg=0.08 mmol) prepared in Example 47 was dissolved in toluene (1 ml), isobutylamine (38 μl=0.38 mmol) was added to the solution, and the mixture was stirred at room temperature for two days. Thus, the title compound (20 mg, 66%) was prepared.

$^1$H NMR (CDCl$_3$) δ 0.92 (6H, d, J=6.8 Hz, OCONHCH$_2$CH(CH$_3$)$_2$), 1.06 (3H, s, 4a-CH$_3$), 1.13 (3H, d, J=7.1 Hz, 5-CH$_3$), 1.78 (1H, m, OCONHCH$_2$CH(CH$_3$)$_2$), 1.87 (3H, br s, 3-CH$_3$), 2.06 (1H, m, 5-H), 2.14 (1H, br d, J=15.9 Hz, 4-H), 2.80 (1H, d, J=15.9 Hz, 4-H), 3.02 (2H, m, OCONHCH$_2$CH(CH$_3$)$_2$), 3.10 (3H, s, N—CH$_3$), 3.53 (3H, s, OCH$_3$), 3.68 (1H, br d, J=4.7 Hz, 7-H), 4.83 (1H, m, OCONHCH$_2$CH(CH$_3$)$_2$), 4.99 (1H, m, 6-H), 5.73 (1H, s, 9-H), 5.77 (1H, d, J=4.7 Hz, 8-H); MS (TSP) m/z 389 (M+H)$^+$.

Example 54

(4aR,5R,6R,7R)-6-Hexylcarbamoyloxy-7-methoxy-4a,5,6,7-tetrahydro-1,3,4a,5-tetramethylbenz[f]indol-2(4H)-one The procedure of Example 6 was repeated, except that the compound (30 mg=0.08 mmol) prepared in Example 47 was dissolved in toluene (1 ml), hexylamine (0.10 ml=0.78 mmol) was added to the solution, and the mixture was stirred at room temperature for 2 hr. Thus, the title compound (30 mg, 93%) was prepared.

$^1$H NMR (CDCl$_3$) δ 0.88 (3H, m, OCONHCH$_2$CH$_2$(CH$_2$)$_3$CH$_3$), 1.05 (3H, s, 4a-CH$_3$), 1.13 (3H, d, J=7.1 Hz, 5-CH$_3$), 1.29 (6H, m, OCONHCH$_2$CH$_2$(CH$_2$)$_3$CH$_3$), 1.51 (2H, m, OCONHCH$_2$CH$_2$(CH$_2$)$_3$CH$_3$), 1.87 (3H, d, J=1.7 Hz, 3-CH$_3$), 2.07 (1H, m, 5-H), 2.14 (1H, br d, J=15.9 Hz, 4-H), 2.80 (1H, d, J=15.9 Hz, 4-H), 3.10 (3H, s, N—CH$_3$), 3.19 (2H, m, OCONHCH$_2$CH$_2$(CH$_2$)$_3$CH$_3$), 3.53 (3H, s, OCH$_3$), 3.69 (1H, br d, J=4.7 Hz, 7-H), 4.79 (1H, m, OCONHCH$_2$CH$_2$(CH$_2$)$_3$CH$_3$), 4.99 (1H, m, 6-H), 5.73 (1H, s, 9-H), 5.77 (1H, d, J=4.7 Hz, 8-H); MS (TSP) m/z 417 (M+H)$^+$.

Example 55

(4aR,5R,6R,7R)-6-Cyclopropylcarbamoyloxy-7-methoxy-4a,5,6,7-tetrahydro-1,3,4a,5-tetramethylbenz[f]indol-2(4H)-one The procedure of Example 6 was repeated, except that the compound (20 mg=0.05 mmol) prepared in Example 47 was dissolved in toluene (0.5 ml), cyclopropylamine (20 μl=0.29 mmol) was added to the solution, and the mixture was stirred at room temperature for three days. Thus, the title compound (13 mg, 68%).

$^1$H NMR (CDCl$_3$) δ 0.52–0.74 (4H, m, OCONHC$_3$H$_5$), 1.00–1.22 (6H, m, 4a-CH$_3$, 5-CH$_3$), 1.87 (3H, d, J=1.7 Hz, 3-CH$_3$), 2.10 (1H, m, 5-H), 2.14 (1H, br d, J=15.9 Hz, 4-H), 2.61 (1H, m, OCONHC$_3$H$_5$), 2.80 (1H, d, J=15.9 Hz, 4-H), 3.10 (3H, s, N—CH$_3$), 3.54 (3H, s, OCH$_3$), 3.71 (1H, br d, J=4.4 Hz, 7-H), 5.00 (2H, m, 6-H, OCONHC$_3$H$_5$), 5.73 (1H, s, 9-H), 5.76 (1H, d, J=4.4 Hz, 8-H); MS (TSP) m/z 373 (M+H)$^+$.

Example 56

(4aR,5R,6R,7R)-6-Benzylcarbamoyloxy-7-methoxy-4a,5,6,7-tetrahydro-1,3,4a,5-tetramethylbenz[f]indol-2(4H)-one The procedure of Example 6 was repeated, except that the compound (50 mg=0.13 mmol) prepared in Example 47 was dissolved in toluene (1 ml), benzylamine (71 μl=0.65 mmol) was added to the solution, and the mixture was stirred at 50° C. for 6 hr. Thus, the title compound (35 mg, 64%) was prepared.

¹H NMR (CDCl₃) δ 1.03 (3H, s, 4a-CH₃), 1.14 (3H, d, J=7.1 Hz, 5-CH₃), 1.86 (3H, d, J=1.7 Hz, 3-CH₃), 2.08 (1H, dq, J=7.1, 2.8 Hz, 5-H), 2.13 (1H, br d, J=15.7 Hz, 4-H), 2.79 (1H, d, J=15.7 Hz, 4-H), 3.08 (3H, s, N—CH₃), 3.54 (3H, s, OCH₃), 3.72 (1H, br d, J=4.6 Hz, 7-H), 4.40 (2H, m, OCONHCH₂C₆H₅), 5.04 (1H, m, 6-H), 5.16 (1H, m, OCONHCH₂C₆H₅), 5.72 (1H, s, 9-H), 5.77 (1H, d, J=4.6 Hz, 8-H), 7.27–7.35 (5H, m, OCONHCH₂C₆H₅); MS (TSP) m/z 423 (M+H)⁺.

Example 57
(4aR,5R,6R,7R)-7-Methoxy-6-phenylcarbamoyloxy-4a,5,6,7-tetrahydro-1,3,4a,5-tetramethylbenz[f]indol-2(4H)-one The procedure of Example 51 was repeated, except that the compound (27 mg=0.09 mmol) prepared in Example 24 was dissolved in DMF (0.5 ml), phenyl isocyanate (0.10 ml=0.92 mmol) was added to the solution, and the mixture was stirred at room temperature for 25 hr. Thus, the title compound (37 mg, 97%) was prepared.

¹H NMR (CDCl₃) δ 0.96 (3H, s, 4a-CH₃), 1.17 (3H, d, J=7.2 Hz, 5-CH₃), 1.87 (3H, d, J=1.9 Hz, 3-CH₃), 2.12 (1H, dq, J=7.2, 2.7 Hz, 5-H), 2.15 (1H, br d, J=15.2 Hz, 4-H), 2.79 (1H, d, J=15.2 Hz, 4-H), 3.08 (3H, s, N—CH₃), 3.56 (3H, s, OCH₃), 3.75 (1H, dd, J=4.8, 1.4 Hz, 7-H), 5.12 (1H, m, 6-H), 5.73 (1H, s, 9-H), 5.80 (1H, d, J=4.8 Hz, 8-H), 7.05–7.57 (5H, m, OCONHC₆H₅), 7.72 (1H, m, OCONHC₆H₅); MS (FAB) m/z 409 (M+H)⁺.

Example 58
(4aR,5R,6R,7R)-6-(2-Hydroxyethylcarbamoyloxy)-7-methoxy-4a,5,6,7-tetrahydro-1,3,4a,5-tetramethylbenz[f]indol-2(4H)-one The procedure of Example 6 was repeated, except that the compound (30 mg=0.08 mmol) prepared in Example 47 was dissolved in toluene (0.5 ml), ethanolamine (23 μl=0.38 mmol) was added to the solution, and the mixture was stirred at room temperature for 2.5 hr. Thus, the title compound (25 mg, 86%) was prepared.

¹H NMR (CDCl₃) δ 0.89 (3H, s, 4a-CH₃), 1.11 (3H, d, J=7.1 Hz, 5-CH₃), 1.84 (3H, br s, 3-CH₃), 2.05 (1H, m, 5-H), 2.11 (1H, br d, J=16.3 Hz, 4-H), 2.76 (1H, d, J=16.3 Hz, 4-H), 3.05 (3H, s, N—CH₃), 3.41 (2H, m, OCONHCH₂CH₂OH), 3.52 (3H, s, OCH₃), 3.69 (1H, br d, J=4.7 Hz, 7-H), 3.78 (2H, m, OCONHCH₂CH₂OH), 4.98 (1H, m, 6-H), 5.73 (1H, s, 9-H), 5.79 (1H, d, J=4.7 Hz, 8-H), 5.92 (1H, m, OCONHCH₂CH₂OH); MS (FAB) m/z 377 (M+H)⁺.

Example 59
(4aR,5R,6R,7R)-6-(N,N-Diethylaminocarbonyloxy)-7-methoxy-4a,5,6,7-tetrahydro-1,3,4a,5-tetramethylbenz[f]indol-2(4H)-one The procedure of Example 48 was repeated, except that the compound (50 mg=0.13 mmol) prepared in Example 47 was dissolved in methylene chloride (2 ml), methyl triflate (15 μl=0.13 mmol) was added to the solution, the mixture was stirred at 10° C. for 30 min, diethylamine (67 μl=0.65 mmol) was added thereto, and the mixture was stirred at room temperature for 30 min. Thus, the title compound (35 mg, 70%) was prepared.

¹H NMR (CDCl₃) δ 1.07–1.17 (6H, m, OCON(CH₂CH₃)₂), 1.10 (3H, s, 4a-CH₃), 1.16 (3H, d, J=7.2 Hz, 5-CH₃), 1.88 (3H, d, J=1.7 Hz, 3-CH₃), 2.12 (1H, dq, J=7.2, 3.0 Hz, 5-H), 2.17 (1H, br d, J=15.9 Hz, 4-H), 2.82 (1H, d, J=15.9 Hz, 4-H), 3.11 (3H, s, N—CH₃), 3.18–3.53 (4H, m, OCON(CH₂CH₃)₂), 3.55 (3H, s, OCH₃), 3.70 (1H, br d, J=4.7 Hz, 7-H), 5.00 (1H, m, 6-H), 5.75 (1H, s, 9-H), 5.77 (1H, d, J=4.7 Hz, 8-H); MS (FAB) m/z 387 (M+H)⁺.

Example 60
(4aR,5R,6R,7R)-7-Methoxy-6-(pyrrolidin-1-ylcarbonyloxy)-4a,5,6,7-tetrahydro-1,3,4a,5-tetramethylbenz[f]indol-2(4H)-one The procedure of Example 6 was repeated, except that the compound (5 mg=0.01 mmol) prepared in Example 47 was dissolved in toluene (0.2 ml), pyrrolidine (10 μl=0.12 mmol) was added to the solution, and the mixture was stirred at room temperature for 3 hr. Thus, the title compound (5 mg, 100%) was prepared.

¹H NMR (CDCl₃) δ 1.11 (3H, s, 4a-CH₃), 1.15 (3H, d, J=7.3 Hz, 5-CH₃), 1.85–1.89 (4H, m, OCOC₄H₈N), 1.88 (3H, d, J=1.7 Hz, 3-CH₃), 2.11 (1H, dq, J=7.3, 4.5 Hz, 5-H), 2.16 (1H, br d, J=15.9 Hz, 4-H), 2.82 (1H, d, J=15.9 Hz, 4-H), 3.11 (3H, s, N—CH₃), 3.28–3.43 (4H, m, OCOC₄H₈N), 3.56 (3H, s, OCH₃), 3.74 (1H, dd, J=4.7, 1.2 Hz, 7-H), 4.97 (1H, m, 6-H), 5.74 (1H, s, 9-H), 5.77 (1H, d, J=4.7 Hz, 8-H); MS (TSP) m/z 387 (M+H)⁺.

Example 61
(4aR,5R,6R,7R)-7-Methoxy-6-(piperidin-1-ylcarbonyloxy)-4a,5,6,7-tetrahydro-1,3,4a,5-tetramethylbenz[f]indol-2(4H)-one The procedure of Example 6 was repeated, except that the compound (40 mg=0.10 mmol) prepared in Example 47 was dissolved in toluene (1 ml), piperidine (51 μl=0.52 mmol) was added to the solution, and the mixture was stirred at 60° C. for 6 hr. Thus, the title compound (35 mg, 85%) was prepared.

¹H NMR (CDCl₃) δ 1.10 (3H, s, 4a-CH₃), 1.14 (3H, d, J=7.2 Hz, 5-CH₃), 1.49–1.59 (6H, m, OCOC₅H₁₀N), 1.88 (3H, d, J=1.9 Hz, 3-CH₃), 2.10 (1H, dq, J=7.2, 3.0 Hz, 5-H), 2.16 (1H, br d, J=16.1 Hz, 4-H), 2.82 (1H, d, J=16.1 Hz, 4-H), 3.11 (3H, s, N—CH₃), 3.32–3.47 (4H, m, OCOC₅H₁₀N), 3.55 (3H, s, OCH₃), 3.72 (1H, dd, J=4.8, 1.2 Hz, 7-H), 5.02 (1H, m, 6-H), 5.75 (1H, s, 9-H), 5.77 (1H, d, J=4.8 Hz, 8-H); MS (TSP) m/z 401 (M+H)⁺.

Example 62
(4aR, 5R, 6R, 7R)-7-Methoxy-6-[(2S)-2-(methoxymethyl)pyrrolidin-1-ylcarbonyloxy]-4a,5,6,7-tetrahydro-1,3,4a,5-tetramethylbenz[f]indol-2(4H)-one The procedure of Example 6 was repeated, except that the compound (30 mg=0.08 mmol) prepared in Example 47 was dissolved in toluene (0.8 ml), (S)-(+)-2-(methoxymethyl)pyrrolidine (72 μl=0.58 mmol) was added to the solution, and the mixture was stirred at 60° C. for 20 hr. Thus, the title compound (25 mg, 75%) was prepared.

¹H NMR (CDCl₃) δ 1.11–1.22 (6H, m, 4a-CH₃, 5-CH₃), 1.88 (3H, d, J=1.9 Hz, 3-CH₃), 1.88–1.95 (4H, m, OCOC₄H₇N—CH₂OCH₃), 2.12 (1H, m, 5-H), 2.16 (1H, br d, J=16.3 Hz, 4-H), 2.81 (1H, d, J=16.3 Hz, 4-H), 3.11 (3H, s, N—CH₃), 3.14–3.52 (8H, m, OCOC₄H₇N—CH₂OCH₃), 3.56 (3H, s, OCH₃), 3.74 (1H, br d, J=4.4 Hz, 7-H), 4.97 (1H, m, 6-H), 5.74 (1H, s, 9-H), 5.75 (1H, d, J=4.4 Hz, 8-H); MS (TSP) m/z 431 (M+H)⁺.

Example 63
(4aR,5R,6R,7R)-6-(4-Ethylpiperazin-1-ylcarbonyloxy)-7-methoxy-4a,5,6,7-tetrahydro-1,3,4a,5-tetramethylbenz[f]indol-2(4H)-one The procedure of Example 6 was repeated, except that the compound (32 mg=0.08 mmol) prepared in Example 47 was dissolved in toluene (1 ml), 1-ethylpiperazine (52 μl=0.41 mmol) was added to the solution, and the mixture was stirred at 60° C. for 15 hr. Thus, the title compound (41 mg, quant).

¹H NMR (CDCl₃) δ 1.09 (3H, t, J=7.2 Hz, OCOC₄H₈N₂—CH₂CH₃), 1.09 (3H, s, 4a-CH₃), 1.14 (3H, d, J=7.2 Hz, 5-CH$_3$), 1.88 (3H, d, J=1.9 Hz, 3-CH$_3$), 2.11 (1H, dq, J=7.2, 3.0 Hz, 5-H), 2.16 (1H, br d, J=16.2 Hz, 4-H), 2.39–2.46 (4H, m, OCOC$_4$H$_8$N$_2$—CH$_2$CH$_3$), 2.42 (2H, q, J=7.2 Hz, OCOC$_4$H$_8$N$_2$—CH$_2$CH$_3$), 2.82 (1H, d, J=16.2 Hz, 4-H), 3.11 (3H, s, N—CH$_3$), 3.44–3.54 (4H, m, OCOC$_4$H$_8$N$_2$—CH$_2$CH$_3$), 3.54 (3H, s, OCH$_3$), 3.72 (1H, dd, J=4.7, 1.2 Hz, 7-H), 5.02 (1H, m, 6-H), 5.75 (1H, s, 9-H), 5.77 (1H, d, J=4.7 Hz, 8-H); MS (TSP) m/z 430 (M+H)$^+$.

Example 64
(4aR,5R,6R,7R)-7-Methoxy-6-(morpholin-4-ylcarbonyloxy)-4a,5,6,7-tetrahydro-1,3,4a,5-tetramethylbenz[f]indol-2(4H)-one The procedure of Example 6 was repeated, except that the compound (34 mg=0.09 mmol) prepared in Example 47 was dissolved in toluene (1 ml), morpholine (76 μl=0.87 mmol) was added thereto, and the mixture was stirred at 60° C. for 2 hr. Thus, the title compound (26 mg, 74%) was prepared.

$^1$H NMR (CDCl$_3$) δ 1.07 (3H, s, 4a-CH$_3$), 1.14 (3H, d, J=7.1 Hz, 5-CH$_3$), 1.88 (3H, d, J=1.9 Hz, 3-CH$_3$), 2.12 (1H, dq, J=7.1, 3.0 Hz, 5-H), 2.17 (1H, br d, J=15.8 Hz, 4-H), 2.82 (1H, d, J=15.8 Hz, 4-H), 3.11 (3H, s, N—CH$_3$), 3.40–3.66 (8H, m, OCOC$_4$H$_8$NO), 3.54 (3H, s, OCH$_3$), 3.71 (1H, br d, J=4.8 Hz, 7-H), 5.04 (1H, m, 6-H), 5.74 (1H, s, 9-H), 5.77 (1H, d, J=4.8 Hz, 8-H); MS (TSP) m/z 403 (M+H)$^+$.

Example 65
(4aR,5R,6R,7R)-6-Ethoxycarbonyloxy-7-methoxy-4a,5,6,7-tetrahydro-1,3,4a,5-tetramethylbenz[f]indol-2(4H)-one The compound (27 mg=0.09 mmol) prepared in Example 24 was dissolved in methylene chloride (0.5 ml), ethyl chloroformate (90 μl=0.94 mmol) was added to the solution in the presence of pyridine (0.3 ml=3.76 mmol), and the mixture was stirred at room temperature for 27 hr. Methylene chloride was added to the reaction mixture, the mixture was washed with water, and the organic phase was dried over sodium sulfate. The solvent was removed under reduced pressure, and the residue was purified by preparative TLC to give the title compound (21 mg, 61%).

$^1$H NMR (CDCl$_3$) δ 1.10 (3H, s, 4a-CH$_3$), 1.16 (3H, d, J=7.1 Hz, 5-CH$_3$), 1.31 (3H, t, J=7.1 Hz, OCOOCH$_2$CH$_3$), 1.87 (3H, d, J=1.9 Hz, 3-CH$_3$), 2.09 (1H, dq, J=7.1, 2.8 Hz, 5-H), 2.14 (1H, br d, J=15.8 Hz, 4-H), 2.81 (1H, d, J=15.8 Hz, 4-H), 3.10 (3H, s, N—CH$_3$), 3.51 (3H, s, OCH$_3$), 3.72 (1H, dd, J=4.7, 1.4 Hz, 7-H), 4.20 (2H, q, J=7.1 Hz, OCOOCH$_2$CH$_3$), 4.89 (1H, m, 6-H), 5.73 (1H, s, 9-H), 5.76 (1H, d, J=4.7 Hz, 8-H); MS (EI) m/z 361 (M)$^+$.

Example 66
(4aR,5R,6R,7R)-7-Methoxy-6-phenoxycarbonyloxy-4a,5,6,7-tetrahydro-1,3,4a,5-tetramethylbenz[f]indol-2(4H)-one The procedure of Example 65 was repeated, except that the compound (27 mg=0.09 mmol) prepared in Example 24 was dissolved in methylene chloride (0.5 ml), phenyl chloroformate (59 μl=0.47 mmol) was added to the solution in the presence of pyridine (91 μl=1.13 mmol), and the mixture was stirred at room temperature for 1.5 hr. Thus, the title compound (36 mg, 94%) was prepared.

$^1$H NMR (CDCl$_3$) δ 1.07 (3H, s, 4a-CH$_3$), 1.22 (3H, d, J=7.1 Hz, 5-CH$_3$), 1.88 (3H, d, J=1.9 Hz, 3-CH$_3$), 2.15 (1H, dq, J=7.1, 2.8 Hz, 5-H), 2.16 (1H, br d, J=15.8 Hz, 4-H), 2.83 (1H, d, J=15.8 Hz, 4-H), 3.11 (3H, s, N—CH$_3$), 3.52 (3H, s, OCH$_3$), 3.82 (1H, dd, J=4.7, 1.4 Hz, 7-H), 4.98 (1H, m, 6-H), 5.75 (1H, s, 9-H), 5.79 (1H, d, J=4.7 Hz, 8-H); 7.16–7.41 (5H, m, OCOOC$_6$H$_5$); MS (EI) m/z 409 (M)$^+$.

Example 67
(4aR,5R,6R,7R)-6-(Imidazol-1-ylthiocarbonyloxy)-7-methoxy-4a,5,6,7-tetrahydro-1,3,4a,5-tetramethylbenz[f]indol-2(4H)-one The compound (30 mg=0.10 mmol) prepared in Example 24 was dissolved in methylene chloride (1 ml), 1,1'-thiocarbonyldiimidazole (27 mg=0.15 mmol) was added to the solution, and the mixture was stirred at room temperature for 20 hr and then at 40° C. for 10 hr. Methylene chloride was added to the reaction mixture, the mixture was washed with water, and the organic phase was dried over sodium sulfate. The solvent was removed under reduced pressure, and the residue was purified by column chromatography on silica gel to give the title compound (40 mg, 97%).

$^1$H NMR (CDCl$_3$) δ 1.19 (3H, s, 4a-CH$_3$), 1.20 (3H, d, J=7.0 Hz, 5-CH$_3$), 1.90 (3H, d, J=1.9 Hz, 3-CH$_3$), 2.23 (1H, br d, J=16.5 Hz, 4-H), 2.35 (1H, dq, J=7.0, 2.6 Hz, 5-H), 2.87 (1H, d, J=16.5 Hz, 4-H), 3.13 (3H, s, N—CH$_3$), 3.58 (3H, s, OCH$_3$), 3.85 (1H, dd, J=4.5, 1.2 Hz, 7-H), 5.77 (1H, s, 9-H), 5.81 (1H, d, J=4.5 Hz, 8-H), 5.91 (1H, m, 6-H), 7.04 (1H, br s, OCSC$_3$N$_2$), 7.59 (1H, br s, OCSC$_3$N$_2$),8.31 (1H, br s, OCSC$_3$N$_2$); MS (TSP) m/z 400 (M+H)$^+$.

Example 68
(4aR,5R,6R,7R)-7-Methoxy-6-propylthiocarbamoyloxy-4a,5,6,7-tetrahydro-1,3,4a,5-tetramethylbenz[f]indol-2(4H)-one The compound (20 mg=0.05 mmol) prepared in Example 67 was dissolved in toluene (0.5 ml), propylamine (20 μl=0.24 mmol) was added to the solution, and the mixture was stirred at room temperature for 30 min. Ethyl acetate was added to the reaction mixture, the mixture was washed with water, and the organic phase was dried over sodium sulfate. The solvent was removed under reduced pressure, and the residue was purified by column chromatography on silica gel to give the title compound (16 mg, 80%).

(Major)
$^1$H NMR (CDCl$_3$) δ 0.97 (3H, t, J=7.3 Hz, OCSNHCH$_2$CH$_2$CH$_3$), 1.01 (3H, s, 4a-CH$_3$), 1.13 (3H, d, J=7.1 Hz, 5-CH$_3$), 1.67 (2H, seq, J=7.3 Hz, OCSNHCH$_2$CH$_2$CH$_3$), 1.86 (3H, d, J=1.9 Hz, 3-CH$_3$), 2.11–2.23 (2H, m, 4-H, 5-H), 2.80 (1H, d, J=15.9 Hz, 4-H), 3.08 (3H, s, N—CH$_3$), 3.55 (2H, br dt, J=7.3 Hz, OCSNHCH$_2$CH$_2$CH$_3$), 3.59 (3H, s, OCH$_3$), 3.75 (1H, dd, J=4.8, 1.8 Hz, 7-H), 5.72 (1H, s, 9-H), 5.78–5.80 (2H, m, 6-H, 8-H), 6.69 (1H, m, OCSNHCH$_2$CH$_2$CH$_3$); MS (TSP) m/z 391 (M+H)$^+$.

(Minor)
$^1$H NMR (CDCl$_3$) δ 0.89 (3H, t, J=7.1 Hz, OCSNHCH$_2$CH$_2$CH$_3$), 1.12 (3H, s, 4a-CH$_3$), 1.16 (3H, d, J=7.2 Hz, 5-CH$_3$), 1.52 (2H, seq, J=7.1 Hz, OCSNHCH$_2$CH$_2$CH$_3$), 1.88 (3H, d, J=1.9 Hz, 3-CH$_3$), 2.11–2.23 (2H, m, 4-H, 5-H), 2.83 (1H, d, J=15.7 Hz, 4-H), 3.12 (3H, s, N—CH$_3$), 3.17 (2H, br dt, J=7.1 Hz, OCSNHCH$_2$CH$_2$CH$_3$), 3. 61 (3H, s, OCH$_3$), 3.79 (1H, dd, J=4.7, 1.7 Hz, 7-H), 5.76 (1H, s, 9-H), 5.78–5.80 (2H, m, 6-H, 8-H), 6.69 (1H, m, OCSNHCH$_2$CH$_2$CH$_3$).

Example 69
(4aR, 5R, 6R, 7R)-7-Methoxy-6-(pyrrolidin-1-ylthiocarbonyloxy)-4a,5, 6,7-tetrahydro-1,3,4a, 5-tetramethylbenz [f]indol-2(4H )-one The procedure of Example 68 was repeated, except that the compound (20 mg=0.05 mmol) prepared in Example 67 was dissolved in toluene (0.5 ml), pyrrolidine (20 μl=0.24 mmol) was added to the solution, and the mixture was stirred at room temperature for 30 min. Thus, the title compound (16 mg, 84%) was prepared.

¹H NMR (CDCl₃) δ 1.12 (3H, s, 4a-CH₃), 1.15 (3H, d, J=7.1 Hz, 5-CH₃), 1.88 (3H, d, J=1.9 Hz, 3-CH₃), 1.91–1.96 (4H, m, OCSC₄H₈N), 2.19 (1H, br d, J=15.9 Hz, 4-H), 2.20 (1H, dq, J=7.1, 2.8 Hz, 5-H), 2.83 (1H, d, J=15.9 Hz, 4-H), 3.11 (3H, s, N—CH₃), 3.51–3.81 (5H, m, 7-H, OCSC₄H₈N), 3.61 (3H, s, OCH₃), 5.75 (1H, s, 9-H), 5.79 (1H, d, J=4.7 Hz, 8-H), 5.82 (1H, m, 6-H); MS (TSP) m/z 403 (M+H)⁺.

Example 70
(4aR, 5R, 6R, 7R)-7-Ethoxy-6-hydroxy-4a, 5,6,7-tetrahydro-1,3,4a,5-tetramethylbenz[f]indol-2(4H)-one Ethanol (10 ml) was added to the compound (100 mg=0.32 mmol) prepared in Example 2, and the mixture was stirred at 50° C. for 3 hr. The solvent was removed under reduced pressure, and the residue was purified by preparative TLC to give the title compound (89 mg, 92%).

¹H NMR (CDCl₃) δ 1.09 (3H, s, 4a-CH₃), 1.18 (3H, d, J=7.1 Hz, 5-CH₃), 1.19 (3H, t, J=7.0 Hz, OCH₂CH₃), 1.84 (3H, d, J=1.9 Hz, 3-CH₃), 1.93 (1H, dq, J=7.1, 2.8 Hz, 5-H), 2.14 (1H, br d, J=15.9 Hz, 4-H), 2.76 (1H, d, J=15.9 Hz, 4-H), 3.08 (3H, s, N—CH₃), 3.61 (1H, ap q, J=7.0 Hz, OCH₂CH₃), 3.62 (1H, ap q, J=7.0 Hz, OCH₂CH₃), 3.79 (1H, dd, J=4.8, 1.5 Hz, 7-H), 3.88 (1H, m, 6-H), 5.73 (1H, s, 9-H), 5.78 (1H, d, J=4.8 Hz, 8-H); MS (EI) m/z 303 (M)⁺; [α]¹⁸_D −454° (c 1.0, MeOH).

Example 71
(4aR,5R,6R,7R)-6-Acetoxy-7-ethoxy-4a,5,6,7-tetrahydro-1,3,4a,5-tetramethylbenz[f]indol-2(4H)-one The compound (32 mg=0.11 mmol) prepared in Example 70 was dissolved in pyridine (1 ml), acetyl chloride (38 μl=0.54 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (18 mg, 50%).

¹H NMR (CDCl₃) δ 1.08 (3H, s, 4a-CH₃), 1.08 (3H, d, J=7.1 Hz, 5-CH₃), 1.20 (3H, t, J=7.0 Hz, OCH₂CH₃), 1.86 (3H, d, J=1.9 Hz, 3-CH₃), 2.05 (3H, s, OCOCH₃), 2.10 (1H, dq, J=7.1, 2.8 Hz, 5-H), 2.15 (1H, br d, J=15.9 Hz, 4-H), 2.78 (1H, d, J=15.9 Hz, 4-H), 3.08 (3H, s, N—CH₃), 3.61 (1H, dq, J=7.0, 2.4 Hz, OCH₂CH₃), 3.69 (1H, dd, J=4.8, 1.5 Hz, 7-H), 3.81 (1H, dq, J=7.0, 2.4 Hz, OCH₂CH₃), 5.03 (1H, m, 6-H), 5.72 (1H, s, 9-H), 5.73 (1H, d, J=4.8 Hz, 8-H); MS (EI) m/z 345 (M)⁺; [α]¹⁸_D −318° (c 1.0, MeOH).

Example 72
(4aR,5R,6R,7R)-7-Ethoxy-6-propionyloxy-4a,5,6,7-tetrahydro-1,3,4a,5-tetramethylbenz[f]indol-2(4H)-one The compound (25 mg=0.08 mmol) prepared in Example 70 was dissolved in pyridine (1 ml), propionyl chloride (25 μl=0.41 mmol) was added to the solution, and the mixture was stirred at room temperature for 18 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (13 mg, 44%).

¹H NMR (CDCl₃) δ 1.08 (3H, d, J=7.1 Hz, 5-CH₃), 1.09 (3H, s, 4a-CH₃), 1.13 (3H, t, J=7.5 Hz, OCOCH₂CH₃), 1.20 (3H, t, J=7.0 Hz, OCH₂CH₃), 1.86 (3H, d, J=1.9 Hz, 3-CH₃), 2.11 (1H, dq, J=7.1, 2.8 Hz, 5-H), 2.15 (1H, br d, J=15.9 Hz, 4-H), 2.33 (2H, q, J=7.5 Hz, OCOCH₂CH₃), 2.78 (1H, d, J=15.9 Hz, 4-H), 3.09 (3H, s, N—CH₃), 3.62 (1H, dq, J=7.0, 2.4 Hz, OCH₂CH₃), 3.68 (1H, dd, J=4.8, 1.5 Hz, 7-H), 3.83 (1H, dq, J=7.0, 2.4 Hz, OCH₂CH₃), 5.06 (1H, m, 6-H), 5.72 (1H, s, 9-H), 5.73 (1H, d, J=4.8 Hz, 8-H); MS (EI) m/z 359 (M)⁺; [α]¹⁸_D −267° (c 1.0, MeOH).

Example 73
(4aR,5R,6R,7R)-7-Ethoxy-6-(2-furancarbonyloxy)-4a,5,6,7-tetrahydro-1,3,4a,5-tetramethylbenz[f]indol-2(4H)-one The compound (20 mg=0.07 mmol) prepared in Example 70 was dissolved in pyridine (1 ml), 2-furoyl chloride (20 μl=0.20 mmol) was added to the solution, and the mixture was stirred at room temperature for 6 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (25 mg, 95%).

¹H NMR (CDCl₃) δ 1.14 (3H, d, J=7.1 Hz, 5-CH₃), 1.20 (3H, s, 4a-CH₃), 1.22 (3H, t, J=7.0 Hz, OCH₂CH₃), 1.87 (3H, d, J=1.9 Hz, 3-CH₃), 2.18 (1H, br d, J=15.9 Hz, 4-H), 2.20 (1H, dq, J=7.1, 2.8 Hz, 5-H), 2.81 (1H, d, J=15.9 Hz, 4-H), 3.09 (3H, s, N—CH₃), 3.66 (1H, dq, J=7.0, 2.4 Hz, OCH₂CH₃), 3.82 (1H, dd, J=4.8, 1.5 Hz, 7-H), 3.89 (1H, dq, J=7.0, 2.4 Hz, OCH₂CH₃), 5.26 (1H, m, 6-H), 5.74 (1H, s, 9-H), 5.75 (1H, d, J=4.8 Hz, 8-H), 6.48 (1H, dd, J=3.5, 1.7 Hz, OCOC₄H₃O), 7.10 (1H, dd, J=3.5, 0.8 Hz, OCOC₄H₃O), 7.57 (1H, dd, J=1.7, 0.8 Hz, OCOC₄H₃O); MS (EI) m/z 397 (M)⁺; [α]¹⁸_D −53° (c 1.0, MeOH).

Example 74
(4aR,5R,6R,7R)-7-Ethoxy-6-(3-methylbutoxy)-4a,5,6,7-tetrahydro-1,3,4a,5-tetramethylbenz[f]indol-2(4H)-one The compound (30 mg=0.08 mmol) prepared in Example 38 was dissolved in ethanol (1 ml), methanesulfonic acid (2 μl=0.03 mmol) was added to the solution, and the mixture was stirred at room temperature for 30 min. Methylene chloride was added to the reaction mixture, the mixture was washed with a saturated aqueous sodium hydrogencarbonate solution, and the organic phase was dried over sodium sulfate. The solvent was removed under reduced pressure, and the residue was purified by preparative TLC to give the title compound (21 mg, 69%).

¹H NMR (CDCl₃) δ 0.89 (3H, d, J=6.7 Hz, OCH₂CH₂CH(CH₃)₂), 0.89 (3H, d, J=6.7 Hz, OCH₂CH₂CH(CH₃)₂), 1.07 (3H, s, 4a-CH₃), 1.15 (3H, d, J=7.1 Hz, 5-CH₃), 1.23 (3H, t, J=7.1 Hz, OCH₂CH₃), 1.45 (2H, m, OCH₂CH₂CH(CH₃)₂), 1.72 (1H, seq, J=6.7 Hz, OCH₂CH₂CH(CH₃)₂), 1.86 (3H, d, J=1.9 Hz, 3-CH₃), 1.91 (1H, dq, J=7.1, 2.8 Hz, 5-H), 2.12 (1H, br d, J=15.9 Hz, 4-H), 2.77 (1H, d, J=15.9 Hz, 4-H), 3.09 (3H, s, N—CH₃), 3.36 (1H, dt, J=9.4, 6.4 Hz, OCH₂CH₂CH(CH₃)₂) 3.36 (1H, m, 6-H), 3.60 (1H, dq, J=9.1, 7.1 Hz, OCH₂CH₃), 3.64 (1H, dt, J=9.4, 6.4 Hz, OCH₂CH₂CH(CH₃)₂) 3.66 (1H, dq, J=9.1, 7.1 Hz, OCH₂CH₃), 3.81 (1H, br d, J=4.9 Hz, 7-H), 5.73 (1H, s, 9-H), 5.79 (1H, d, J=4.9 Hz, 8-H); MS (EI) m/z 373 (M)⁺.

Example 75
(4aR,5R,6R,7R)-7-Ethoxy-6-(imidazol-1-ylcarbonyloxy)-4a,5,6,7-tetrahydro-1,3,4a,5-tetramethylbenz[f]indol-2(4H)-one The procedure of Example 5 was repeated, except that the compound (104 mg=0.34 mmol) prepared in Example 70 was dissolved in methylene chloride (3 ml), 1,1'-carbonyldiimidazole (121 mg=0.74 mmol) was added to the solution, and the mixture was stirred at room temperature for 3 hr, followed by purification by preparative TLC to give the title compound (153 mg, quant).

$^1$H NMR (CDCl$_3$) δ 1.18 (3H, s, 4a-CH$_3$), 1.21 (3H, d, J=7.2 Hz, 5-CH$_3$), 1.26 (3H, t, J=7.0 Hz, OCH$_2$CH$_3$), 1.90 (3H, d, J=1.9 Hz, 3-CH$_3$), 2.23 (1H, br d, J=16.4 Hz, 4-H), 2.28 (1H, dq, J=7.2, 2.8 Hz, 5-H), 2.85 (1H, d, J=16.4 Hz, 4-H), 3.12 (3H, s, N—CH$_3$), 3.51 (1H, br d, J=5.4 Hz, 7-H), 3.69 (1H, dq, J=9.3, 7.0 Hz, OCH$_2$CH$_3$), 3.88 (1H, dq, J=9.3, 7.0 Hz, OCH$_2$CH$_3$), 5.25 (1H, m, 6-H), 5.76 (1H, s, 9-H), 5.77 (1H, d, J=5.4 Hz, 8-H), 7.09 (1H, br s, OCOC$_3$N$_2$), 7.38 (1H, br s, OCOC$_3$N$_2$),8.10 (1H, br s, OCOC$_3$N$_2$); MS (FAB) m/z 398 (M+H)$^+$.

Example 76
(4aR,5R,6R,7R)-7-Ethoxy-6-propylcarbamoyloxy-4a,5,6,7-tetrahydro-1,3,4a,5-tetramethylbenz[f]indol-2(4H)-one The procedure of Example 6 was repeated, except that the compound (40 mg=0.10 mmol) prepared in Example 75 was prepared in toluene (1 ml), propylamine (84 μl=1.02 mmol) was added to the solution, and the mixture was stirred at 50° C. for 2 hr, followed by purification by preparative TLC to give the title compound (32 mg, 82%).

$^1$H NMR (CDCl$_3$) δ 0.92 (3H, t, J=7.1 Hz, OCONHCH$_2$CH$_2$CH$_3$), 1.01 (3H, s, 4a-CH$_3$), 1.11 (3H, d, J=7.2 Hz, 5-CH$_3$), 1.21 (3H, t, J=7.0 Hz, OCH$_2$CH$_3$), 1.54 (2H, seq, J=7.1 Hz, OCONHCH$_2$CH$_2$CH$_3$), 1.85 (3H, br s, 3-CH$_3$), 2.08 (1H, dq, J=7.2, 2.6 Hz, 5-H), 2.14 (1H, br d, J=15.8 Hz, 4-H), 2.77 (1H, d, J=15.8 Hz, 4-H), 3.07 (3H, s, N—CH$_3$), 3.16 (2H, br dt, J=7.1 Hz, OCONHCH$_2$CH$_2$CH$_3$), 3.64 (1H, dq, J=9.4, 7.0 Hz, OCH$_2$CH$_3$), 3.77 (1H, br d, J=4.9 Hz, 7-H), 3.87 (1H, dq, J=9.4, 7.0 Hz, OCH$_2$CH$_3$), 4.95 (1H, m, 6-H), 4.99 (1H, m, OCONHCH$_2$CH$_2$CH$_3$), 5.71 (1H, s, 9-H), 5.74 (1H, d, J=4.9 Hz, 8-H); MS (EI) m/z 389 (M+H)$^+$.

Example 77
(4aR,5R,6R,7R)-6-Hydroxy-7-(1-Methylethoxy)-4a,5,6,7-tetrahydro-1,3,4a,5-tetramethylbenz[f]indol-2(4H)-one Isopropanol (10 ml) was added to the compound (100 mg=0.32 mmol) prepared in Example 2, and the mixture was stirred at 50° C. for 3 hr. The solvent was removed under reduced pressure, and the residue was purified by preparative TLC to give the title compound (64 mg, 63%).

$^1$H NMR (CDCl$_3$) δ 1.09 (3H, s, 4a-CH$_3$), 1.16 (6H, d, J=6.1 Hz, OCH(CH$_3$)$_2$) 1.17 (3H, d, J=7.1 Hz, 5-CH$_3$), 1.84 (3H, d, J=1.9 Hz, 3-CH$_3$), 1.95 (1H, dq, J=7.1, 2.7 Hz, 5-H), 2.14 (1H, br d, J=15.9 Hz, 4-H), 2.75 (1H, d, J=15.9 Hz, 4-H), 3.07 (3H, s, N—CH$_3$), 3.77 (1H, sep, J=6.1 Hz, OCH(CH$_3$)$_2$), 3.81 (1H, br s, 6-H), 3.85 (1H, br d, J=4.7 Hz, 7-H), 5.72 (1H, d, J=4.7 Hz, 8-H), 5.73 (1H, s, 9-H); MS (EI)m/z 317 (M)$^+$; [α]$^{28}_D$ –457° (c 1.0, MeOH).

Example 78
(4aR,5R,6R,7R)-7-(1-Methylethoxy)-6-propionyloxy-4a,5,6,7-tetrahydro-1,3,4a,5-tetramethylbenz[f]indol-2(4H)-one The compound (19 mg=0.06 mmol) prepared in Example 77 was dissolved in pyridine (1 ml), propionyl chloride (18 μl=0.30 mmol) was added to the solution, and the mixture was stirred at room temperature for 24 hr. Methylene chloride (20 ml) was added to the reaction mixture, and the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (7 mg, 31%).

$^1$H NMR (CDCl$_3$) δ 1.08 (3H, d, J=7.1 Hz, 5-CH$_3$), 1.09 (3H, s, 4a-CH$_3$), 1.14 (3H, t, J=7.6 Hz, OCOCH$_2$CH$_3$), 1.16 (3H, d, J=6.1 Hz, OCH(CH$_3$)$_2$), 1.19 (3H, d, J=6.1 Hz, OCH(CH$_3$)$_2$), 1.86 (3H, d, J=1.9 Hz, 3-CH$_3$), 2.13 (1H, dq, J=7.1, 2.7 Hz, 5-H), 2.16 (1H, br d, J=15.9 Hz, 4-H), 2.34 (2H, ap q,J=7.6 Hz, OCOCH$_2$CH$_3$), 2.78 (1H, d, J=15.9 Hz, 4-H), 3.08 (3H, s, N—CH$_3$), 3.75 (1H, dd, J=4.8, 1.4 Hz, 7-H), 3.97 (1H, sep, J=6.1 Hz, OCH(CH$_3$)$_2$), 4.96 (1H, m, 6-H), 5.67 (1H, d, J=4.8 Hz, 8-H), 5.72 (1H, s, 9-H); MS (FAB) m/z 374 (M+H)$^+$; [α]$^{28}_D$ –304° (c 0.5, MeOH).

Example 79
(4aR,5R,6R,7R)-6-Cyclopropylcarbonyloxy-7-(1-methylethoxy)-4a,5,6,7-tetrahydro-1,3,4a,5-tetramethylbenz[f]indol-2(4H)-one The procedure of Example 3 was repeated, except that the compound (40 mg=0.13 mmol) prepared in Example 77 was dissolved in pyridine (1 ml), cyclopropanecarbonyl chloride (23 μl=0.25 mmol) was added to the solution, and the mixture was stirred at 55° C. for 12 hr. Thus, the title compound (32 mg, 66%) was prepared.

$^1$H NMR (CDCl$_3$) δ 0.80–1.04 (4H, m, OCOC$_3$H$_5$), 1.07 (3H, d, J=7.1 Hz, 5-CH$_3$), 1.09 (3H, s, 4a-CH$_3$), 1.14 (3H, d, J=6.0 Hz, OCH(CH$_3$)$_2$), 1.16 (3H, d, J=6.0 Hz, OCH(CH$_3$)$_2$)1.56 (1H, m, OCOC$_3$H$_5$), 1.85 (3H, d, J=1.9 Hz, 3-CH$_3$), 2.11 (1H, dq, J=7.1, 2.8 Hz, 5-H), 2.14 (1H, br d, J=15.9 Hz, 4-H), 2.77 (1H, d, J=15.9 Hz, 4-H), 3.07 (3H, s, N—CH$_3$), 3.73 (1H, dd, J=4.7, 1.4 Hz, 7-H), 3.94 (1H, sep, J=6.0 Hz, OCH(CH$_3$)$_2$), 4.93 (1H, m, 6-H), 5.6G (1H, d, J=4.7 Hz, 8-H), 5.71 (1H, s, 9-H); MS (EI) m/z 385 (M)$^+$; [α]$^{20}_D$ –231° (c 1.0, MeOH).

Example 80
(4aR,5R,6R,7R)-6-(2-Furancarbonyloxy)-7-(1-methyl)ethoxy-4a,5,6,7-tetrahydro-1,3,4a,5-tetramethylbenz[f]indol-2(4H)-one The compound (19 mg=0.06 mmol) prepared in Example 77 was dissolved in pyridine (1 ml), 2-furoyl chloride (18 μl=0.18 mmol) was added to the solution, and the mixture was stirred at room temperature for 20 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (22 mg, 89%).

$^1$H NMR (CDCl$_3$) δ 1.14 (3H, d, J=7.1 Hz, 5-CH$_3$), 1.17 (3H, d, J=6.1 Hz, OCH(CH$_3$)$_2$), 1.20 (3H, s, 4a-CH$_3$), 1.22 (3H, d, J=6.1 Hz, OCH(CH$_3$)$_2$), 1.87 (3H, d, J=1.9 Hz, 3-CH$_3$), 2.20 (1H, br d, J=15.9 Hz, 4-H), 2.22 (1H, dq, J=7.1, 2.7 Hz, 5-H), 2.82 (1H, d, J=15.9 Hz, 4-H), 3.09 (3H, s, N—CH$_3$), 3.89 (1H, br d, J=4.8 Hz, 7-H), 4.03 (1H, sep, J=6.1 Hz, OCH(CH$_3$)$_2$), 5.17 (1H, m, 6-H), 5.69 (1H, d, J=4.8 Hz, 8-H), 5.74 (1H, s, 9-H), 6.49 (1H, dd, J=3.5, 1.8 Hz, OCOC$_4$H$_3$O), 7.10 (1H, d, J=3.5 Hz, OCOC$_4$H$_3$O), 7.56 (1H, m, OCOC$_4$H$_3$O); MS (EI)m/z 411 (M)$^+$; [α]$^{28}_D$ –55° (c 1.0, MeOH).

Example 81
(4aR,5R,6R,7R)-7-(1-Methylethoxy)-6-(4-pyridinecarbonyloxy)-4a,5,6,7-tetrahydro-1,3,4a,5-tetramethylbenz[f]indol-2(4H)-one The procedure of Example 3 was repeated, except that the compound (50 mg=0.16 mmol) prepared in Example 77 was dissolved in pyridine (1 ml), isonicotinoyl chloride hydrochloride (56 mg=0.32 mmol) was added to the solution, and the mixture was stirred at 55° C. for 15 hr. Thus, the title compound (22 mg, 33%) was prepared.

$^1$H NMR (CDCl$_3$) δ 1.16 (3H, d, J=6.0 Hz, OCH(CH$_3$)$_2$), 1.18 (3H, d, J=7.1 Hz, 5-CH$_3$), 1.23 (3H, s, 4a-CH$_3$), 1.24 (3H, d, J=6.0 Hz, OCH(CH$_3$)$_2$), 1.88 (3H, d, J=1.9 Hz, 3-CH$_3$), 2.23 (1H, br d, J=15.9 Hz, 4-H), 2.28 (1H, dq, J=7.1, 2.8 Hz, 5-H), 2.83 (1H, d, J=15.9 Hz, 4-H), 3.10 (3H, s, N—CH$_3$), 3.88 (1H, dd, J=4.7, 1.4 Hz, 7-H), 4.06 (1H, sep, J=6.0 Hz, OCH(CH$_3$)$_2$), 5.24 (1H, m, 6-H), 5.70 (1H, d, J=4.7 Hz, 8-H), 5.74 (1H, s, 9-H), 7.70 (2H, J=6.1 Hz, OCOC$_5$H$_4$N), 8.77 (2H, J=6.1 Hz, OCOC$_5$H$_4$N); MS (EI) m/z 422 (M)$^+$; [α]$^{20}$$_D$ −74° (c 1.0, MeOH).

Example 82
(4aR,5R,6R,7R)-6-Ethoxy-7-(1-methylethoxy)-4a,5,6,7-tetrahydro-1,3,4a,5-tetramethylbenz[f]indol-2(4H)-one The procedure of Example 34 was repeated, except that the compound (52 mg=0.16 mmol) prepared in Example 77 was dissolved in DMF (0.3 ml), 60% sodium hydride (42 mg=1.05 mmol) as an oil and ethyl iodide (0.16 ml=1.95 mmol) were added to the solution, and the mixture was stirred at 60° C. for 3.5 hr. Thus, the title compound (28 mg, 49%) was prepared.

$^1$H NMR (CDCl$_3$) δ 1.07 (3H, s, 4a-CH$_3$), 1.15 (3H, d, J=7.1 Hz, 5-CH$_3$), 1.18 (3H, t, J=7.0 Hz, OCH$_2$CH$_3$), 1.19 (3H, d, J=6.0 Hz, OCH(CH$_3$)$_2$), 1.19 (3H, d, J=6.0 Hz, OCH(CH$_3$)$_2$), 1.86 (3H, d, J=2.0 Hz, 3-CH$_3$), 1.93 (1H, dq, J=7.1, 2.7 Hz, 5-H), 2.12 (1H, br d, J=15.9 Hz, 4-H), 2.77 (1H, d, J=15.9 Hz, 4-H), 3.08 (3H, s, N—CH$_3$), 3.30 (1H, m, 6-H), 3.40 (1H, dq, J=9.2, 7.0 Hz, OCH$_2$CH$_3$), 3.67 (1H, dq, J=9.2, 7.0 Hz, OCH$_2$CH$_3$), 3.86 (1H, br d, J=4.1 Hz, 7-H), 3.75 (1H, sep, J=6.0 Hz, OCH(CH$_3$)$_2$), 5.72 (1H, s, 9-H), 5.73 (1H, d, J=4.1 Hz, 8-H); MS (EI) m/z 345 (M)$^+$.

Example 83
(4aR,5R,6R,7R)-7-(1-Methylethoxy)-6-propoxy-4a,5,6,7-tetrahydro-1,3,4a,5-tetramethylbenz[f]indol-2(4H)-one The procedure of Example 34 was repeated, except that the compound (51 mg=0.16 mmol) prepared in Example 77 was dissolved in DMF (0.3 ml), 60% sodium hydride (44 mg=1.09 mmol) as an oil and propyl iodide (0.19 ml=1.93 mmol) were added to the solution, and the mixture was stirred at 60° C. for 4 hr. Thus, the title compound (19 mg, 34%) was prepared.

$^1$H NMR (CDCl$_3$) δ 0.92 (3H, t, J=7.4 Hz, OCH$_2$CH$_2$CH$_3$), 1.08 (3H, s, 4a-CH$_3$), 1.16 (3H, d, J=7.1 Hz, 5-CH$_3$), 1.19 (3H, d, J=6.1 Hz, OCH(CH$_3$)$_2$), 1.20 (3H, d, J=6.1 Hz, OCH(CH$_3$)$_2$), 1.57 (2H, m, OCH$_2$CH$_2$CH$_3$), 1.86 (3H, d, J=1.9 Hz, 3-CH$_3$), 1.94 (1H, dq, J=7.1, 2.7 Hz, 5-H), 2.12 (1H, br d, J=15.9 Hz, 4-H), 2.77 (1H, d, J=15.9 Hz, 4-H), 3.09 (3H, s, N—CH$_3$), 3.29 (1H, dt, J=8.8, 6.4 Hz, OCH$_2$CH$_2$CH$_3$), 3.29 (1H, m, 6-H), 3.58 (1H, dt, J=8.8, 6.4 Hz, OCH$_2$CH$_2$CH$_3$), 3.87 (1H, dd, J=5.2, 1.3 Hz, 7-H), 3.76 (1H, sep, J=6.1 Hz, OCH(CH$_3$)$_2$), 5.72 (1H, d, J=5.2 Hz, 8-H), 5.73 (1H, s, 9-H); MS (EI) m/z 359 (M)$^+$.

Example 84
(4aR,5R,6R,7R)-6-Butoxy-7-(1-methylethoxy)-4a,5,6,7-tetrahydro-1,3,4a,5-tetramethylbenz[f]indol-2(4H)-one The procedure of Example 34 was repeated, except that the compound (58 mg=0.18 mmol) prepared in Example 77 was dissolved in DMF (0.3 ml), 60% sodium hydride (23 mg=0.54 mmol) as an oil and butyl iodide (0.10 ml=1.08 mmol) were added to the solution, and the mixture was stirred at 60° C. for 3 hr. Thus, the title compound (13 mg, 19%) was prepared.

$^1$H NMR (CDCl$_3$) δ 0.10 (3H, t, J=7.2 Hz, OCH$_2$CH$_2$CH$_2$CH$_3$), 1.05 (3H, s, 4a-CH$_3$), 1.14 (3H, d, J=7.1 Hz, 5-CH$_3$), 1.18 (3H, d, J=6.0 Hz, OCH(CH$_3$)$_2$), 1.19 (3H, d, J=6.0 Hz, OCH(CH$_3$)$_2$), 1.37 (2H, m, OCH$_2$CH$_2$CH$_2$CH$_3$), 1.52 (2H, m, OCH$_2$CH$_2$CH$_2$CH$_3$), 1.85 (3H, d, J=1.9 Hz, 3-CH$_3$), 1.92 (1H, dq, J=7.1, 2.8 Hz, 5-H), 2.11 (1H, br d, J=15.9 Hz, 4-H), 2.75 (1H, d, J=15.9 Hz, 4-H), 3.07 (3H, s, N—CH$_3$), 3.27 (1H, m, 6-H), 3.32 (1H, dt, J=8.9, 6.2 Hz, OCH$_2$CH$_2$CH$_2$CH$_3$), 3.60 (1H, dt, J=8.9, 6.2 Hz, OCH$_2$CH$_2$CH$_2$CH$_3$), 3.75 (1H, sep, J=6.0 Hz, OCH(CH$_3$)$_2$), 3.85 (1H, dd, J=5.2, 1.4 Hz, 7-H), 5.71 (1H, d, J=5.2 Hz, 8-H), 5.71 (1H, s, 9-H); MS (EI) m/z 373 (M)$^+$; [α]$^{20}$$_D$ −308° (c 1.0, MeOH).

Example 85
(4aR,5R,6R,7R)-6-(3-Methylbutoxy)-7-(1-methylethoxy)-4a,5,6,7-tetrahydro-1,3,4a,5-tetramethylbenz[f]indol-2(4H)-one The procedure of Example 34 was repeated, except that the compound (130 mg=0.41 mmol) prepared in Example 77 was dissolved in DMF (0.7 ml), 60% sodium hydride (50 mg =1.23 mmol) as an oil and isoamyl iodide (0.32 ml=2.46 mmol) were added to the solution, and the mixture was stirred at 60° C. for 3 hr. Thus, the title compound (18 mg, 11%) was prepared.

$^1$H NMR (CDCl$_3$) δ 0.87 (3H, d, J=6.6 Hz, OCH$_2$CH$_2$CH(CH$_3$)$_2$), 0.88 (3H, d, J=6.6 Hz, OCH$_2$CH$_2$CH(CH$_3$)$_2$), 1.05 (3H, s, 4a-CH$_3$), 1.14 (3H, d, J=7.1 Hz, 5-CH$_3$), 1.18 (3H, d, J=6.0 Hz, OCH(CH$_3$)$_2$), 1.19 (3H, d, J=6.0 Hz, OCH(CH$_3$)$_2$), 1.43 (2H, m, OCH$_2$CH$_2$CH(CH$_3$)$_2$), 1.70 (1H, m, OCH$_2$CH$_2$CH(CH$_3$)$_2$), 1.85 (3H, d, J=1.9 Hz, 3-CH$_3$), 1.92 (1H, dq, J=7.1, 2.8 Hz, 5-H), 2.11 (1H, br d, J=15.9 Hz, 4-H), 2.75 (1H, d, J=15.9 Hz, 4-H), 3.07 (3H, s, N—CH$_3$), 3.27 (1H, m, 6-H), 3.34 (1H, dt, J=9.1, 6.3 Hz, OCH$_2$CH$_2$CH(CH$_3$)$_2$), 3.62 (1H, dt, J=9.1, 6.3 Hz, OCH$_2$CH$_2$CH(CH$_3$)$_2$), 3.75 (1H, sep, J=6.0 Hz, OCH(CH$_3$)$_2$), 3.85 (1H, dd, J=5.2, 1.4 Hz, 7-H), 5.71 (1H, d, J=5.2 Hz, 8-H), 5.71 (1H, s, 9-H); MS (EI) m/z 387 (M)$^+$; [α]$^{20}$$_D$ −289° (c 1.0, MeOH).

Example 86
(4aR,5R,6R,7R)-6-Cyclopropylmethoxy-7-(1-methylethoxy)-4a,5,6,7-tetrahydro-1,3,4a,5-tetramethylbenz[f] indol-2(4H)-one The procedure of Example 34 was repeated, except that the compound (60 mg=0.19 mmol) prepared in Example 77 was dissolved in DMF (0.3 ml), 60% sodium hydride (24 mg=0.57 mmol) as an oil and (bromomethyl)cyclopropane (0.11 ml=1.14 mmol) were added to the solution, and the mixture was stirred at 60° C. for 3 hr. Thus, the title compound (15 mg, 22%) was prepared.

$^1$H NMR (CDCl$_3$) δ 0.10–0.54 (4H, m, OCH$_2$C$_3$H$_5$), 1.00 (1H, m, OCH$_2$C$_3$H$_5$), 1.07 (3H, s, 4a-CH$_3$), 1.15 (3H, d, J=7.1 Hz, 5-CH$_3$), 1.17 (3H, d, J=6.0 Hz, OCH(CH$_3$)$_2$), 1.18 (3H, d, J=6.0 Hz, OCH(CH$_3$)$_2$), 1.85 (3H, d, J=1.9 Hz, 3-CH$_3$), 1.92 (1H, dq, J=7.1, 2.8 Hz, 5-H), 2.11 (1H, br d, J=15.9 Hz, 4-H), 2.76 (1H, d, J=15.9 Hz, 4-H), 3.07 (3H, s, N—CH$_3$), 3.23 (1H, dd, J=10.2, 6.6 Hz, OCH$_2$C$_3$H$_5$), 3.33 (1H, m, 6-H), 3.47 (1H, dd, J=10.2, 6.6 Hz, OCH$_2$C$_3$H$_5$), 3.73 (1H, sep, J=6.0 Hz, OCH(CH$_3$)$_2$), 3.84 (1H, dd, J=5.2, 1.4 Hz, 7-H), 5.71 (1H, s, 9-H), 5.72 (1H, d, J=5.2 Hz, 8-H); MS (EI) m/z 371 (M)$^+$; [α]$^{20}$$_D$ −515° (c 1.0, MeOH).

Example 87
(4aR,5R,6R,7R)-6-(Imidazol-1-ylcarbonyloxy)-7-(1-methylethoxy)-4a,5,6,7-tetrahydro-1,3,4a,5-tetramethylbenz[f]indol-2(4H)-one The procedure of Example 5 was repeated, except that the compound (100 mg=0.32 mmol) prepared in Example 77 was dissolved in methylene chloride (2 ml), 1,1'- carbonyldiimidazole (204 mg=1.26 mmol) was added to the solution, and the mixture was stirred at room temperature for 3 hr. Thus, the title compound (120 mg, 93%) was prepared.

$^1$H NMR (CDCl$_3$) δ 1.18 (3H, s, 4a-CH$_3$), 1.21 (3H, d, J=6.1 Hz, OCH(CH$_3$)$_2$), 1.22 (3H, d, J=7.3 Hz, 5-CH$_3$), 1.25 (3H, d, J=6.1 Hz, OCH(CH$_3$)$_2$), 1.90 (3H, d, J=1.9 Hz, 3-CH$_3$), 2.23 (1H, br d, J=15.7 Hz, 4-H), 2.30 (1H, dq, J=7.3, 2.6 Hz, 5-H), 2.85 (1H, d, J=15.7 Hz, 4-H), 3.12 (3H, s, N—CH$_3$), 3.98 (1H, dd, J=4.8, 1.1 Hz, 7-H), 4.01 (1H, sep, J=6.1 Hz, OCH(CH$_3$)$_2$), 5.16 (1H, m, 6-H), 5.71 (1H, d, J=4.8 Hz, 8-H), 5.75 (1H, s, 9-H), 7.09 (1H, br s, OCOC$_3$N$_2$), 7.39 (1H, br s, OCOC$_3$N$_2$), 8.10 (1H, br s, OCOC$_3$N$_2$); MS (TSP) m/z 412 (M+H)$^+$.

Example 88

(4aR,5R,6R,7R)-6-Methylcarbamoyloxy-7-(1-methylethoxy)-4a,5,6,7-tetrahydro-1,3,4a,5-tetramethylbenz[f]indol-2(4H)-one The procedure of Example 6 was repeated, except that the compound (50 mg=0.12 mmol) prepared in Example 87 was dissolved in THF (0.4 ml), a 2 M methylamine/THF solution (0.61 ml=1.22 mmol) was added to the solution, and the mixture was stirred at room temperature for 2 hr, followed by purification by preparative TLC. Thus, the title compound (41 mg, 89%) was prepared.

$^1$H NMR (CDCl$_3$) δ 0.98 (3H, s, 4a-CH$_3$), 1.11 (3H, d, J=7.1 Hz, 5-CH$_3$), 1.17 (3H, d, J=6.3 Hz, OCH(CH$_3$)$_2$), 1.20 (3H, d, J=6.3 Hz, OCH(CH$_3$)$_2$), 1.85 (3H, br s, 3-CH$_3$), 2.14 (1H, br d, J=16.2 Hz, 4-H), 2.15 (1H, dq, J=7.1, 2.4 Hz, 5-H), 2.76 (1H, d, J=16.2 Hz, 4-H), 2.82 (3H, d, J=4.7 Hz, OCONHCH$_3$), 3.06 (3H, s, N—CH$_3$), 3.83 (1H, br d, J=5.0 Hz, 7-H), 4.02 (1H, sep, J=6.3 Hz, OCH(CH$_3$)$_2$), 4.85 (1H, m, 6-H), 5.04 (1H, m, OCONHCH$_3$), 5.68 (1H, d, J=5.0 Hz, 8-H), 5.70 (1H, s, 9-H); MS (FAB) m/z 375 (M+H)$^+$.

Example 89

(4aR,5R,6R,7R)-7-(1-Methylethoxy)-6-propylcarbamoyloxy-4a,5,6,7-tetrahydro-1,3,4a,5-tetramethylbenz[f]indol-2(4H)-one The procedure of Example 6 was repeated, except that the compound (44 mg=0.11 mmol) prepared in Example 87 was dissolved in toluene (1 ml), propylamine (43 μl=0.52 mmol) was added to the solution, and the mixture was stirred at 60° C. for 3 hr. Thus, the title compound (30 mg, 70%) was prepared.

$^1$H NMR (CDCl$_3$) 0.93 (3H, t, J=7.3 Hz, OCONHCH$_2$CH$_2$CH$_3$), 1.03 (3H, s, 4a-CH$_3$), 1.12 (3H, d, J=7.1 Hz, 5-CH$_3$), 1.18 (3H, d, J=6.5 Hz, OCH(CH$_3$)$_2$), 1.21 (3H, d, J=6.5 Hz, OCH(CH$_3$)$_2$), 1.55 (2H, seq, J=7.3 Hz, OCONHCH$_2$CH$_2$CH$_3$), 1.86 (3H, br s, 3-CH$_3$), 2.12 (1H, br q, J=7.1 Hz, 5-H), 2.16 (1H, br d, J=16.6 Hz, 4-H), 2.78 (1H, d, J=16.6 Hz, 4-H), 3.08 (3H, s, N—CH$_3$), 3.16 (2H, br dt, J=7.3 Hz, OCONHCH$_2$CH$_2$CH$_3$), 3.84 (1H, br d, J=4.7 Hz, 7-H), 4.03 (1H, sep, J=6.5 Hz, OCH(CH$_3$)$_2$), 4.09 (1H, m, OCONHCH$_2$CH$_2$CH$_3$), 4.86 (1H, m, 6-H), 5.69 (1H, d, J=4.7 Hz, 8-H), 5.72 (1H, s, 9-H); MS (TSP) m/z 403 (M+H)$^+$.

Example 90

(4aR,5R,6R,7R)-6-Hydroxy-7-(2-methylpropoxy)-4a, 5,6,7-tetrahydro-1,3,4a,5-tetramethylbenz[f]indol-2(4H)-one The procedure of Example 24 was repeated, except that the compound (100 mg=0.32 mmol) prepared in Example 2 was dissolved in isopropanol (3 ml) and the mixture was stirred at 50° C. for 3 hr, followed by column chromatography on silica gel. Thus, the title compound (85 mg, 82%) was prepared.

$^1$H NMR (CDCl$_3$) δ 0.90 (3H, d, J=6.7 Hz, OCH$_2$CH(CH$_3$)$_2$), 0.91 (3H, d, J=6.7 Hz, OCH$_2$CH(CH$_3$)$_2$), 1.12 (3H, s, 4a-CH$_3$), 1.19 (1H, m, OCH$_2$CH(CH$_3$)$_2$), 1.21 (3H, d, J=7.3 Hz, 5-CH$_3$), 1.87 (3H, d, J=2.1 Hz, 3-CH$_3$), 1.96 (1H, dq, J=7.3, 2.5 Hz, 5-H), 2.17 (1H, br d, J=15.8 Hz, 4-H), 2.79 (1H, d, J=15.8 Hz, 4-H), 3.11 (3H, s, N—CH$_3$), 3.12–3.36 (2H, m, OCH$_2$CH(CH$_3$)$_2$), 3.79 (1H, dd, J=4.7, 1.7 Hz, 7-H), 3.90 (1H, m, 6-H), 5.79 (1H, s, 9-H), 5.81 (1H, d, J=4.7 Hz, 8-H); MS (FAB) m/z 331 (M)$^+$.

Example 91

(4aR,5R,6R,7R)-6-(Imidazol-1-ylcarbonyloxy)-7-(2-methylpropoxy)-4a,5,6,7-tetrahydro-1,3,4a,5-tetramethylbenz[f] indol-2(4H)-one The procedure of Example 5 was repeated, except that the compound (180 mg=0.54 mmol) prepared in Example 90 was dissolved in methylene chloride (4 ml), 1,1'-carbonyldiimidazole (175 mg=1.08 mmol) was added to the solution, and the mixture was stirred at room temperature for 3 hr. Thus, the title compound (190 mg, 82%) was prepared.

$^1$H NMR (CDCl$_3$) δ 0.91–0.96 (6H, m, OCH$_2$CH(CH$_3$)$_2$), 1.18 (3H, s, 4a-CH$_3$), 1.19 (1H, m, OCH$_2$CH(CH$_3$)$_2$), 1.21 (3H, d, J=7.0 Hz, 5-CH$_3$),1.90 (3H, br s, 3-CH$_3$), 2.23 (1H, br d, J=15.9 Hz, 4-H), 2.26 (1H, m, 5-H), 2.85 (1H, d, J=15.9 Hz, 4-H), 3.12 (3H, s, N—CH$_3$), 3.42–3.53 (2H, m, OCH$_2$CH(CH$_3$)$_2$), 3.88 (1H, m, 7-H), 5.24 (1H, m, 6-H), 5.77 (2H, m, 8-H, 9-H), 7.08 (1H, br s, OCOC$_3$N$_2$), 7.38 (1H, br s, OCOC$_3$N$_2$), 8.10 (1H, br s, OCOC$_3$N$_2$); MS (TSP) m/z 426 (M+H)$^+$.

Example 92

(4aR,5R,6R,7R)-7-(2-Methylpropoxy)-6-propylcarbamoyloxy-4a,5,6,7-tetrahydro-1,3,4a,5-tetramethylbenz[f]indol-2(4H)-one The procedure of Example 6 was repeated, except that the compound (36 mg=0.08 mmol) prepared in Example 91 was dissolved in toluene (1 ml), propylamine (69 μl=0.84 mmol) was added to the solution, and the mixture was stirred at room temperature for 15 hr. Thus, the title compound (27 mg, 77%) was prepared.

$^1$H NMR (CDCl$_3$) δ 0.91 (3H, d, J=6.6 Hz, OCH$_2$CH(CH$_3$)$_2$), 0.92 (3H, d, J=6.6 Hz, OCH$_2$CH(CH$_3$)$_2$), 0.95 (3H, t, J=7.0 Hz, OCONHCH$_2$CH$_2$CH$_3$), 1.04 (3H, s, 4a-CH$_3$), 1.12 (1H, m, OCH$_2$CH(CH$_3$)$_2$), 1.12 (3H, d, J=7.0 Hz, 5-CH$_3$), 1.55 (2H, seq, J=7.0 Hz, OCONHCH$_2$CH$_2$CH$_3$), 1.87 (3H, br s, 3-CH$_3$), 2.09 (1H, dq, J=7.0, 2.3 Hz, 5-H), 2.16 (1H, br d, J=16.2 Hz, 4-H), 2.79 (1H, d, J=16.2 Hz, 4-H), 3.09 (3H, s, N—CH$_3$), 3.17 (2H, br dt, J=7.0 Hz, OCONHCH$_2$CH$_2$CH$_3$), 3.40 (1H, dd, J=9.2, 6.8 Hz, OCH$_2$CH(CH$_3$)$_2$), 3.53 (1H, dd, J=9.2, 6.8 Hz, OCH$_2$CH(CH$_3$)$_2$), 3.76 (1H, br d, J=4.7 Hz, 7-H), 4.89 (1H, m, OCONHCH$_2$CH$_2$CH$_3$), 4.95 (1H, m, 6-H), 5.74 (1H, s, 9-H), 5.77 (1H, d, J=4.7 Hz, 8-H); MS (TSP) m/z 417 (M+H)$^+$.

Example 93

(4aR,5R,6R,7R)-7-Cyclopropylmethoxy-6-hydroxy-4a,5,6,7-tetrahydro-1,3,4a,5-tetramethylbenz[f]indol-2(4H)-one The procedure of Example 24 was repeated, except that the compound (200 mg=0.63 mmol) prepared in Example 2 was dissolved in cyclopropane methanol (4 ml) and the solution was stirred at 50 for 8 hr, followed by chromatography on silica gel. Thus, the title compound (190 mg, 92%) was prepared.

$^1$H NMR (CDCl$_3$) δ 0.20–0.57 (4H, m, OCH$_2$C$_3$H$_5$), 1.07 (1H, m, OCH$_2$C$_3$H$_5$), 1.12 (3H, s, 4a-CH$_3$), 1.20 (3H, d, J=7.3 Hz, 5-CH$_3$), 1.87 (3H, d, J=1.9 Hz, 3-CH$_3$), 1.97 (1H, dq, J=7.3, 2.5 Hz, 5-H), 2.17 (1H, br d, J=15.9 Hz, 4-H), 2.78 (1H, d, J=15.9 Hz, 4-H), 3.11 (3H, s, N—CH$_3$), 3.41 (1H, d, J=6.9 Hz, OCH$_2$C$_3$H$_5$), 3.42 (1H, d, J=6.9 Hz,

OCH$_2$C$_3$H$_5$), 3.86 (1H, dd, J=4.7, 1.6 Hz, 7-H), 3.92 (1H, m, 6-H), 5.76 (1H, s, 9-H), 5.82 (1H, d, J=4.7 Hz, 8-H); MS (TSP) m/z 330 (M+H)$^+$.

Example 94
(4aR,5R,6R,7R)-7-Cyclopropylmethoxy-6-(imidazol-1-ylcarbonyloxy)-4a,5,6,7-tetrahydro-1,3,4a,5-tetramethylbenz[f]indol-2(4H)-one The procedure of Example 5 was repeated, except that the compound (100 mg=0.30 mmol) prepared in Example 93 was dissolved in methylene chloride (2 ml), 1,1'-carbonyldiimidazole (97 mg=0.60 mmol) was added to the solution, and the mixture was stirred at room temperature for 3 hr. Thus, the title compound (120 mg, 93%).

$^1$H NMR (CDCl$_3$) δ 0.25–0.59 (4H, m, OCH$_2$C$_3$H$_5$), 1.11 (1H, m, OCH$_2$C$_3$H$_5$), 1.18 (3H, s, 4a-CH$_3$), 1.22 (3H, d, J=7.2 Hz, 5-CH$_3$), 1.90 (3H, d, J=1.9 Hz, 3-CH$_3$), 2.23 (1H, br d, J=16.2 Hz, 4-H), 2.31 (1H, dq, J=7.2, 2.8 Hz, 5-H), 2.85 (1H, d, J=16.2 Hz, 4-H), 3.12 (3H, s, N—CH$_3$), 3.50 (1H, dd, J=10.2, 6.9 Hz, OCH$_2$C$_3$H$_5$), 3.63 (1H, dd, J=10.2, 6.9 Hz, OCH$_2$C$_3$H$_5$), 3.96 (1H, br d, J=4.6 Hz, 7-H), 5.24 (1H, m, 6-H), 5.76 (1H, s, 9-H), 5.79 (1H, d, J=4.6 Hz, 8-H), 7.08 (1H, br s, OCOC$_3$N$_2$), 7.38 (1H, br s, OCOC$_3$N$_2$),8.10 (1H, br s, OCOC$_3$N$_2$); MS (TSP) m/z 424 (M+H)$^+$.

Example 95
(4aR,5R,6R,7R)-7-Cyclopropylmethoxy-6-propylcarbamoyloxy-4a,5,6,7-tetrahydro-1,3,4a,5-tetramethylbenz[f]indol-2(4H)-one The procedure of Example 6 was repeated, except that the compound (40 mg=0.09 mmol) prepared in Example 94 was dissolved in toluene (1 ml), propylamine (76 μl=0.92 mmol) was added to the solution, and the mixture was stirred at 60° C. for 15 hr. Thus, the title compound (15 mg, 38%) was prepared.

$^1$H NMR (CDCl$_3$) δ 0.22–0.55 (4H, m, OCH$_2$C$_3$H$_5$), 0.93 (3H, t, J=7.3 Hz, OCONHCH$_2$CH$_2$CH$_3$), 1.04 (3H, s, 4a-CH$_3$), 1.08 (1H, m, OCH$_2$C$_3$H$_5$), 1.12 (3H, d, J=7.1 Hz, 5-CH$_3$), 1.54 (2H, seq, J=7.3 Hz, OCONHCH$_2$CH$_2$CH$_3$), 1.89 (3H, br s, 3-CH$_3$), 2.12 (1H, br q, J=7.1 Hz, 5-H), 2.16 (1H, br d, J=15.9 Hz, 4-H), 2.78 (1H, d, J=15.9 Hz, 4-H), 3.09 (3H, s,N—CH$_3$), 3.13 (2H, br dt, J=7.3 Hz, OCONHCH$_2$CH$_2$CH$_3$), 3.47 (1H, dd, J=10.2, 6.9 Hz, OCH$_2$C$_3$H$_5$), 3.61 (1H, dd, J=10.2, 6.9 Hz, OCH$_2$C$_3$H$_5$), 3.81 (1H, br d, J=6.1 Hz, 7-H), 4.84 (1H, m, 6-H), 4.87 (1H, m, OCONHCH$_2$CH$_2$CH$_3$) 5.73 (1H, s, 9-H), 5.78 (1H, d, J=6.1 Hz, 8-H); MS (TSP) m/z 415 (M+H)$^+$.

Example 96
(4aR, 5R, 6R, 7R)-6-Hydroxy-7-methylthio-4a, 5,6,7-tetrahydro-1,3,4a,5-tetramethylbenz[f]indol-2(4H)-one The compound (152 mg=0.48 mmol) prepared in Example 2 was dissolved in methylene chloride (3 ml), methanesulfonic acid (6 μl=0.10 mmol) was added to the solution in the presence of methylmercaptan (250 mg=5.20 mmol), and the mixture was stirred at 0 for 30 min. Methylene chloride was added to the reaction mixture, the mixture was washed with saturated saline, and the organic phase was dried over sodium sulfate. The solvent was removed under reduced pressure, and the residue was purified by chromatography on silica gel to give the title compound (83 mg, 57%).

$^1$H NMR (CDCl$_3$) δ 1.15 (3H, s, 4a-CH$_3$), 1.22 (3H, d, J=7.3 Hz, 5-CH$_3$), 1.88 (3H, d, J=2.0 Hz, 3-CH$_3$), 2.12 (1H, br d, J=15.2 Hz, 4-H), 2.13 (1H, dq, J=7.3, 2.3 Hz, 5-H), 2.19 (3H, s, S—CH$_3$), 2.81 (1H, d, J=15.2 Hz, 4-H), 3.11 (3H, s, N—CH$_3$), 3.45 (1H, br d, J=5.5 Hz, 7-H), 4.00 (1H, m, 6-H), 5.74 (1H, d, J=5.5 Hz, 8-H), 5.75 (1H, s, 9-H); MS (EI) m/z 305 (M)$^+$.

Example 97
(4aR,5R,6R,7R)-7-Methylthio-6-propionyloxy-4a,5,6,7-tetrahydro-1,3,4a,5-tetramethylbenz[f]indol-2(4H)-one The procedure of Example 3 was repeated, except that the compound (21 mg=0.07 mmol) prepared in Example 96 was dissolved in methylene chloride (0.4 ml), propionyl chloride (26 μl=0.30 mmol) was added to the solution in the presence of pyridine (54 μl=0.67 mmol), and the mixture was stirred at room temperature for 3 hr. Thus, the title compound (17 mg, 71%) was prepared.

$^1$H NMR (CDCl$_3$) δ 1.12 (3H, d, J=7.0 Hz, 5-CH$_3$), 1.14 (3H, s, 4a-CH$_3$) 1.15 (3H, t, J=7.6 Hz, OCOCH$_2$CH$_3$), 1.88 (3H, d, J=1.9 Hz, 3-CH$_3$), 2.15 (1H, br d, J=15.8 Hz, 4-H), 2.31 (3H, s, S—CH$_3$), 2.35 (1H, dq, J=7.0, 2.0 Hz, 5-H), 2.35 (2H, q, J=7.6 Hz, OCOCH$_2$CH$_3$), 2.83 (1H, d, J=15.8 Hz, 4-H), 3.11 (3H, s, N—CH$_3$), 3.41 (1H, br d, J=4.9 Hz, 7-H), 5.11 (1H, m, 6-H), 5.69 (1H, d, J=4.9 Hz, 8-H), 5.73 (1H, s, 9-H); MS (EI) m/z 361 (M)$^+$.

Example 98
(4aR,5R,6R,7R)-6-Benzoyloxy-7-methylthio-4a,5,6,7-tetrahydro-1,3,4a,5-tetramethylbenz[f]indol-2(4H)-one The procedure of Example 3 was repeated, except that the compound (20 mg=0.07 mmol) prepared in Example 96 was dissolved in methylene chloride (0.5 ml), benzoyl chloride (34 μl=0.29 mmol) was added to the solution in the presence of 4-dimethylaminopyridine (46 mg=0.37 mmol), and the mixture was stirred at room temperature for 2 hr. Thus, the title compound (26 mg, 96%) was prepared.

$^1$H NMR (CDCl$_3$) δ 1.21 (3H, d, J=7.1 Hz, 5-CH$_3$), 1.30 (3H, s, 4a-CH$_3$), 1.91 (3H, d, J=1.9 Hz, 3-CH$_3$), 2.21 (1H, br d, J=15.9 Hz, 4-H), 2.39 (3H, s, S—CH$_3$), 2.49 (1H, dq, J=7.1, 2.5 Hz, 5-H), 2.89 (1H, d, J=15.9 Hz, 4-H), 3.13 (3H, s, N—CH$_3$), 3.57 (1H, br d, J=4.9 Hz, 7-H), 5.38 (1H, m, 6-H), 5.74 (1H, d, J=4.9 Hz, 8-H), 5.76 (1H, s, 9-H), 7.42–7.49 (2H, m, OCOC$_6$H$_5$), 7.58 (1H, m, OCOC$_6$H$_5$), 7.98–8.01 (2H, m, OCOC$_6$H$_5$); MS (EI) m/z 409 (M)$^+$.

Example 99
(4aR,5R,6R,7R)-6-(Imidazol-1-ylcarbonyloxy)-7-methylthio-4a,5,6,7-tetrahydro-1,3,4a,5-tetramethylbenz[f]indol-2(4H)-one The procedure of Example 5 was repeated, except that the compound (18 mg=0.06 mmol) prepared in Example 96 was dissolved in methylene chloride (0.6 ml), 1,1'-carbonyldiimidazole (21 mg=0.13 mmol) was added to the solution, and the mixture was stirred at room temperature for 3 hr, followed by purification by preparative TLC to give the title compound (25 mg, 100%).

$^1$H NMR (CDCl$_3$) δ 1.21 (3H, s, 4a-CH$_3$), 1.24 (3H, d, J=7.1 Hz, 5-CH$_3$), 1.90 (3H, d, J=1.9 Hz, 3-CH$_3$), 2.21 (1H, br d, J=15.3 Hz, 4-H), 2.35 (3H, s, S—CH$_3$), 2.51 (1H, dq, J=7.1, :2.4 Hz, 5-H), 2.88 (1H, d, J=15.3 Hz, 4-H), 3.12 (3H, s, N—CH$_3$), 3.61 (1H, br d, J=5.1 Hz, 7-H), 5.31 (1H, m, 6-H), 5.71 (1H, d, J=5.1 Hz, 8-H), 5.75 (1H, s, 9-H), 7.08 (1H, br s, OCOC$_3$H$_3$N$_2$), 7.38 (1H, br s, OCOC$_3$H$_3$N$_2$), 8.10 (1H, br s, OCOC$_3$H$_3$N$_2$); MS (FAB) m/z 400 (M+H)$^+$.

Example 100
(4aR,5R,6R,7R)-7-Ethylthio-6-hydroxy-4a,5,6,7-tetrahydro-1,3,4a,5-tetramethrlbenz[f]indol-2(4H)-one The procedure of Example 96 was repeated, except that the compound (488 mg=1.54 mmol) prepared in Example 2 was dissolved in methylene chloride (10 ml), methanesulfonic acid (40 μl=0.62 mmol) was added to the solution in the presence of ethyl mercaptan (1.10 ml=14.9 mmol), and the mixture was stirred at room temperature for 20 min. Thus, the title compound (477 mg, 97%) was prepared.

¹H NMR (CDCl₃) δ 1.14 (3H, s, 4a-CH₃), 1.21 (3H, d, J=7.2 Hz, 5-CH₃), 1.29 (3H, t, J=7.4 Hz, S—CH₂CH₃), 1.87 (3H, d, J=1.9 Hz, 3-CH₃), 2.13 (1H, br d, J=15.7 Hz, 4-H), 2.14 (1H, dq, J=7.2, 2.1 Hz, 5-H), 2.62 (1H, dq, J=12.5, 7.4 Hz, S—CH₂CH₃), 2.68 (1H, dq, J=12.5, 7.4 Hz, S—CH₂CH₃), 2.80 (1H, d, J=15.7 Hz, 4-H), 3.10 (3H, s, N—CH₃), 3.52 (1H, dd, J=4.9, 1.5 Hz, 7-H), 3.98 (1H, m, 6-H), 5.74 (1H, d, J=4.9 Hz, 8-H), 5.75 (1H, s, 9-H); MS (EI) m/z 319 (M)⁺.

Example 101
(4aR,5R,6R,7R)-7-Ethylthio-6-propionyloxy-4a,5,6,7-tetrahydro-1,3,4a,5-tetramethylbenz[f]indol-2(4H)-one The procedure of Example 3 was repeated, except that the compound (31 mg=0.10 mmol) prepared in Example 100 was dissolved in methylene chloride (0.6 ml), propionyl chloride (38 μl=0.44 mmol) was added to the solution in the presence of pyridine (94 μl=1.16 mmol), and the mixture was stirred at room temperature for 3 hr. Thus, the title compound (30 mg, 82%) was prepared.

¹H NMR (CDCl₃) δ 1.11 (3H, d, J=7.0 Hz, 5-CH₃), 1.13 (3H, s, 4a-CH₃), 1.15 (3H, t, J=7.5 Hz, OCOCH₂CH₃), 1.31 (3H, t, J=7.4 Hz, S—CH₂CH₃), 1.88 (3H, d, J=1.9 Hz, 3-CH₃), 2.14 (1H, br d, J=16.4 Hz, 4-H), 2.35 (2H, ap q, J=7.5 Hz, OCOCH₂CH₃), 2.36 (1H, br q, J=7.0 Hz, 5-H), 2.75 (1H, dq, J=12.7, 7.4 Hz, S—CH₂CH₃), 2.82 (1H, d, J=16.4 Hz, 4-H), 2.86 (1H, dq, J=12.7, 7.4 Hz, S—CH₂CH₃), 3.11 (3H, s, N—CH₃), 3.49 (1H, br d, J=5.0 Hz, 7-H), 5.08 (1H, m, 6-H), 5.68 (1H, d, J=5.0 Hz, 8-H), 5.72 (1H, s, 9-H); MS (EI) m/z 375 (M)⁺.

Example 102
(4aR,5R,6R,7R)-6-Benzoyloxy-7-ethylthio-4a,5,6,7-tetrahydro-1,3,4a,5-tetramethylbenz[f]indol-2(4H)-one The procedure of Example 3 was repeated, except that the compound (30 mg=0.10 mmol) prepared in Example 100 was dissolved in methylene chloride (0.6 ml), benzoyl chloride (50 μl=0.43 mmol) was added to the solution in the presence of 4-dimethylaminopyridine (64 mg=0.53 mmol), and the mixture was stirred at room temperature for 3 hr. Thus, the title compound (45 mg, 100%) was prepared.

¹H NMR (CDCl₃) δ 1.20 (3H, d, J=7.2 Hz, 5-CH,), 1.30 (3H, s, 4a-CH₃), 1.35 (3H, t, J=7.4 Hz, S—CH₂CH₃), 1.90 (3H, d, J=1.9 Hz, 3-CH₃), 2.21 (1H, br d, J=15.9 Hz, 4-H), 2.50 (1H, dq, J=7.2, 2.4 Hz, 5-H), 2.83 (1H, dq, J=12.6, 7.4 Hz, S—CH₂CH₃), 2.88 (1H, d, J=15.9 Hz, 4-H), 2.95 (1H, dq, J=12.6, 7.4 Hz, S—CH₂CH₃), 3.12 (3H, s, N—CH₃), 3.65 (1H, br d, J=5.0 Hz, 7-H), 5.36 (1H, m, 6-H), 5.73 (1H, d, J=5.0 Hz, 8-H), 5.76 (1H, s, 9-H), 7.42–7.47 (2H, m, OCOC₆H₅), 7.58 (1H, m, OCOC₆H₅), 7.98–8.02 (2H, m, OCOC₆H₅); MS (EI) m/z 422 (M–H)⁺.

Example 103
(4aR,5R,6R,7R)-6-Butoxy-7-ethylthio-4a,5,6,7-tetrahydro-1,3,4a,5-tetramethylbenz[f]indol-2(4H)-one The procedure of Example 96 was repeated, except that the compound (37 mg=0.11 mmol) prepared in Example 37 was dissolved in methylene chloride (0.8 ml), methanesulfonic acid (3 μl=0.04 mmol) was added to the solution in the presence of ethylmercaptan (80 μl=1.08 mmol), and the mixture was stirred at room temperature for 30 min, followed by purification by preparative TLC. Thus, the title compound (37 mg, 62%) was prepared.

¹H NMR (CDCl₃) δ 0.90 (3H, t, J=7.3 Hz, OCH₂CH₂CH₂CH₃), 1.09 (3H, s, 4a-CH₃), 1.16 (3H, d, J=7.1 Hz, 5-CH₃), 1.30 (3H, t, J=7.4 Hz, S—CH₂CH₃), 1.37 (2H, m, OCH₂CH₂CH₂CH₃) 1.53 (2H, m, OCH₂CH₂CH₂CH₃) 1.86 (3H, d J=1.9 Hz, 3-CH₃), 2.08 (1H, br d, J=15.1 Hz, 4-H), 2.09 (1H, dq, J=7.1, 2.6 Hz, 5-H), 2.61 (1H, dq, J=11.4, 7.4 Hz, S—CH₂CH₃), 2.66 (1H, dq, J=11.4, 7.4 Hz, S—CH₂CH₃), 2.78 (1H, d, J=15.1 Hz, 4-H), 3.09 (3H, s, N—CH₃), 3.28 (1H, dt, J=8.9, 6.2 Hz, OCH₂CH₂CH₂CH₃)3.44 (1H, m, 6-H), 3.55 (1H, br d, J=4.8 Hz, 7-H), 3.58 (1H, dt, J=8.9, 6.2 Hz, OCH₂CH₂CH₂CH₃), 5.71 (1H, d, J=4.8 Hz, 8-H), 5.72 (1H, s, 9-H); MS (EI) m/z 375 (M)⁺.

Example 104
(4aR,5R,6R,7R)-7-Ethylthio-6-(3-methylbutoxy)-4a,5,6,7-tetrahydro-1,3,4a,5-tetramethylbenz[f]indol-2(4H)-one The procedure of Example 96 was repeated, except that the compound (20 mg=0.06 mmol) prepared in Example 38 was dissolved in methylene chloride (0.5 ml), methanesulfonic acid (1 μl=0.02 mmol) was added to the solution in the presence of ethylmercaptan (45 μl=0.61 mmol), and the mixture was stirred at room temperature for 20 min, followed by purification by preparative TLC to give the title compound (19 mg, 89%).

¹H NMR (CDCl₃) δ 0.89 (3H, d, J=6.7 Hz, OCH₂CH₂CH(CH₃)₂), 0.90 (3H, d, J=6.7 Hz, OCH₂CH₂CH(CH₃)₂), 1.09 (3H, s, 4a-CH₃), 1.16 (3H, d, J=7.1 Hz, 5-CH₃), 1.31 (3H, t, J=7.4 Hz, S—CH₂CH₃), 1.44 (2H, m, OCH₂CH₂CH(CH₃)₂) 1.70 (1H, seq, J=6.7 Hz, OCH₂CH₂CH(CH₃)₂) 1.87 (3H, d, J=1.9 Hz, 3-CH₃) 2.09 (1H, br d, J=15.1 Hz, 4-H), 2.09 (1H, dq, J=7.1, 2.5 Hz, 5-H), 2.66 (1H, dq, J=12.7, 7.4 Hz, S—CH₂CH₃), 2.67 (1H, dq, J=12.7, 7.4 Hz, S—CH₂CH₃), 2.79 (1H, d, J=15.1 Hz, 4-H), 3.09 (3H, s, N—CH₃), 3.30 (1H, dt, J=9.1, 6.5 Hz, OCH₂CH₂CH(CH₃)₂), 3.44 (1H, m, 6-H), 3.56 (1H, br d, J=4.7 Hz, 7-H), 3.60 (1H, dt, J=9.1, 6.5 Hz, OCH₂CH₂CH(CH₃)₂), 5.71 (1H, d, J=4.7 Hz, 8-H), 5.72 (1H, s, 9-H); MS (EI) m/z 389 (M)⁺.

Example 105
(4aR, 5R,6R,7R)-6-Cyclopropylmethoxy-7-ethylthio-4a,5,6,7-tetrahydro-1,3,4a,5-tetramethylbenz[f]indol-2(4H)-one The procedure of Example 96 was repeated, except that the compound (37 mg=0.11 mmol) prepared in Example 40 was dissolved in methylene chloride (0.8 ml), methanesulfonic acid (3 μl=0.04 mmol) was added to the solution in the presence of ethylmercaptan (79 μl=1.07 mmol), and the mixture was stirred at room temperature for 20 min, followed by purification by preparative TLC. Thus, the title compound (19 mg, 47%) was prepared.

¹H NMR (CDCl₃) δ 0.18–0.24 (2H, m, OCH₂C₃H₅), 0.45–0.53 (2H, m, OCH₂C₃H₅), 1.03 (1H, m, OCH₂C₃H₅), 1.11 (3H, s, 4a-CH₃), 1.17 (3H, d, J=7.1 Hz, 5-CH₃), 1.30 (3H, t, J=7.4 Hz, S—CH₂CH₃), 1.87 (3H, d, J=1.9 Hz, 3-CH₃), 2.09 (1H, br d, J=15.1 Hz, 4-H), 2.10 (1H, dq, J=7.1, 2.5 Hz, 5-H), 2.62 (1H, dq, J=12.5, 7.4 Hz, S—CH₂CH₃), 2.63 (1H, dq, J=12.5, 7.4 Hz, S—CH₂CH₃), 2.79 (1H, d, J=15.1 Hz, 4-H), 3.09 (3H, s, N—CH₃), 3.21 (1H, dd, J=10.0, 6.4 Hz, OCH₂C₃H₅), 3.45 (1H, dd, J=10.0, 6.4 Hz, OCH₂C₃H₅), 3.50 (1H, m, 6-H), 3.54 (1H, br d, J=4.4 Hz, 7-H), 5.72 (1H, d, J=4.4 Hz, 8-H), 5.72 (1H, s, 9-H); MS (EI) m/z 373 (M)⁺.

Example 106
(4aR,5R,6R,7R)-7-Ethylthio-6-(imidazol-1-ylcarbonyloxy)-4a,5,6,7-tetrahydro-1,3,4a,5-tetramethylbenz[f]indol-2(4H)-one The procedure of Example 5 was repeated, except that the compound (152 mg=0.48 mmol) prepared in Example 100 was dissolved in methylene chloride (3 ml), 1,1'-carbonyldiimidazole (156 mg=0.96 mmol) was added to the solution, and the mixture was stirred at room temperature for 2 hr. Thus, the title compound (213 mg, 100%) was prepared.

¹H NMR (CDCl₃) δ 1.21 (3H, s, 4a-CH₃), 1.23 (3H, d, J=7.1 Hz, 5-CH₃), 1.35 (3H, t, J=7.4 Hz, S—CH₂CH₃), 1.95 (3H, d, J=1,9 Hz, 3-CH₃), 2.21 (1H, br d, J=16.0 Hz, 4-H), 2.53 (1H, dq, J=7.1, 2.3 Hz, 5-H), 2.78 (1H, dq, J=12.6, 7.4 Hz, S—CH₂CH₃), 2.88 (1H, d, J=16.0 Hz, 4-H), 2.89 (1H, dq, J=12.6, 7.4 Hz, S—CH₂CH₃), 3.13 (3H, s, N—CH₃), 3.70 (1H, br d, J=4.9 Hz, 7-H), 5.29 (1H, m, 6-H), 5.70 (1H, d, J=4.9 Hz, 8-H), 5.74 (1H, s, 9-H), 7.09 (1H, br s, OCOC₃H₃N₂), 7.39 (1H, br s,OCOC₃H₃N₂), 8.11 (1H, br s, OCOC₃H₃N₂); MS (FAB) m/z 414 (M+H)⁺.

Example 107
(4aR,5R,6R,7R)-7-Ethylthio-6-propylcarbamoyloxy-4a,5,6,7-tetrahydro-1,3,4a,5-tetramethylbenz[f]indol-2(4H)-one The procedure of Example 6 was repeated, except that the compound (46 mg=0.11 mmol) prepared in Example 106 was dissolved in toluene (1 ml), propylamine (90 μl=1.10 mmol) was added to the solution, and the mixture was stirred at room temperature for 2 hr and at 50° C. for 4 hr, followed by purification by preparative TLC to give the title compound (33 mg, 75%).

¹H NMR (CDCl₃) δ 0.93 (3H, t, J=7.1 Hz, OCONHCH₂CH₂CH₃), 1.06 (3H, s, 4a-CH₃), 1.14 (3H, d, J=7.0 Hz, 5-CH₃), 1.31 (3H, t, J=7.3 Hz, S—CH₂CH₃), 1.54 (2H, seq, J=7.1 Hz, OCONHCH₂CH₂CH₃), 1.87 (3H, d, J=1.6 Hz, 3-CH₃), 2.13 (1H, br d, J=16.3 Hz, 4-H), 2.34 (1H, dq, J=7.0, 2.2 Hz, 5-H), 2.77 (1H, dq, J=12.8, 7.3 Hz, S—CH₂CH₃), 2.81 (1H, d, J=16.3 Hz, 4-H), 2.87 (1H, dq, J=12.8, 7.3 Hz, S—CH₂CH₃), 3.09 (3H, s, N—CH₃), 3.15 (2H, br dt, J=7.1 Hz, OCONHCH₂CH₂CH₃), 3.57 (1H, br d, J=5.3 Hz, 7-H), 4.82 (1H, m, NH), 4.96 (1H, m, 6-H), 5.70 (1H, d, J=5.3 Hz, 8-H), 5.71 (1H, s, 9-H); MS (FAB) m/z 405 (M+H)⁺.

Example 108
(4aR,5R,6R,7R)-7-Ethylthio-6-(pyrrolidin-1-ylcarbonyloxy)-4a,5,6,7-tetrahydro-1,3,4a,5-tetramethylbenz[f]indol-2(4H)-one The procedure of Example 6 was repeated, except that the compound (45 m(=0.11 mmol) prepared in Example 106 was dissolved in toluene (1 ml), pyrrolidine (45 μl=0.54 mmol) was added to the solution, and the mixture was stirred at room temperature for 1 hr, followed by purification by preparative TLC to give the title compound (41 mg, 92%).

¹H NMR (CDCl₃) δ 1.12 (3H, s, 4a-CH₃), 1.15 (3H, d, J=7.1 Hz, 5-CH₃), 1.30 (3H, t, J=7.4 Hz, S—CH₂CH₃), 1.82–1.89 (4H, m, OCOC₄H₈N), 1.87 (3H, d, J=1.5 Hz, 3-CH₃), 2.14 (1H, br d, J=15.9 Hz, 4-H), 2.36 (1H, dq, J=7.1, 2.5 Hz, 5-H), 2.80 (1H, dq, J=12.6, 7.4 Hz, S—CH₂CH₃), 2.82 (1H, d, J=15.9 Hz, 4-H), 2.91 (1H, dq, J=12.6, 7.4 Hz, S—CH₂CH₃), 3.10 (3H, s, N—CH₃), 3.28 (2H, br t, J=6.7 Hz, OCOC₄H₈N), 3.39 (2H, br t, J=5.6 Hz, OCOC₄H₈N), 3.63 (1H, br d, J=5.2 Hz, 7-H), 4.94 (1H, m, 6-H), 5.69 (1H, d, J=5.2 Hz, 8-H), 5.71 (1H, s, 9-H); MS (FAB) m/z 417 (M+H)⁺.

Example 109
(4aR,5R,6R,7R)-6-Hydroxy-7-phenylthio-4a, 5,6,7-tetrahydro-1,3,4a,5-tetramethylbenz [f]indol-2(4H)-one The procedure of Example 2 was repeated, except that the compound (37 mg=0.12 mmol) prepared in Example 96 was dissolved in methylene chloride (0.8 ml), methanesulfonic acid (3 μl=0.05 mmol) was added to the solution in the presence of thiophenol (24 μl=0.23 mmol), and the mixture was stirred at room temperature for 15 min, followed by purification by preparative TLC to give the title compound (34 mg, 81%).

¹H NMR (CDCl₃) δ 1.15 (3H, s, 4a-CH₃), 1.18 (3H, d, J=7.3 Hz, 5-CH₃), 1.87 (3H, d, J=2.0 Hz, 3-CH₃), 2.08 (1H, br d, J=15.9 Hz, 4-H), 2.15 (1H, dq, J=7.3, 2.2 Hz, 5-H), 2.79 (1H, d, J=15.9 Hz, 4-H), 3.10 (3H, s, N—CH₃), 3.99 (1H, m, 6-H), 4.02 (1H, br d, J=4.9 Hz, 7-H), 5.77 (1H, s, 9-H), 5.81 (1H, d, J=4.9 Hz, 8-H), 7.21–7.33 (3H, m, S—C₆H₅), 7.39–7.43 (2H, m, S—C₆H₅); MS (FAB) m/z 368 (M+H)⁺.

Example 110
(4aR,5R,6R,7R)-7-Fhenylthio-6-propionyloxy-4a,5,6,7-tetrahydro-1,3,4a,5-tetramethylbenz[f]indol-2(4H)-one The procedure of 3 was repeated, except that the compound (22 mg=0.06 mmol) prepared in Example 109 was dissolved in methylene chloride (0.5 ml), propionyl chloride (24 μl=0.28 mmol) was added to the solution in the presence of pyridine (50 μl=0.62 mmol), and the mixture was stirred at room temperature for 70 hr. Thus, the title compound (18 mg, 69%) was prepared.

¹H NMR (CDCl₃) δ 1.07 (3H, d, J=7.2 Hz, 5-CH₃), 1.12 (3H, s, 4a-CH₃), 1.13 (3H, t, J=7.5 Hz, OCOCH₂CH₃), 1.88 (3H, d, J=1.9 Hz, 3-CH₃), 2.07 (1H, br d, J=15.9 Hz, 4-H), 2.29 (1H, dq, J=7.2, 2.2 Hz, 5-H), 2.32 (2H, q, J=7.5 Hz, OCOCH₂CH₃), 2.80 (1H, d, J=15.9 Hz, 4-H), 3.12 (3H, s, N—CH₃), 3.93 (1H, dd, J=5.0, 1.5 Hz, 7-H), 5.19 (1H, m, 6-H), 5.76 (1H, s, 9-H), 5.78 (1H, d, J=5.0 Hz, 8-H), 7.24–7.36 (3H, m, S—C₆H₅), 7.49–7.53 (2H, m, S—C₆H₅); MS (FAB) m/z 424 (M+H)⁺.

Example 111
(4aR, 5R)-6-Oxo-4a, 5,6,7-tetrahydro-1, 3, 4a, 5-tetramethylbenz [f]indol-2 (4H )-one The compound (20 mg=0.07 mmol) prepared in Example 24 was dissolved in benzene (4 ml), methanesulfonic acid (4.5 μl=0.07 mmol) was added to the solution, and the mixture was heated at 60° under reflux for 20 min. The reaction mixture was cooled, benzene was added thereto, the mixture was washed with saturated saline, and the organic phase was dried over sodium sulfate. The solvent was removed under reduced pressure, and the residue was purified by preparative TLC to give the title compound (6 mg, 36%).

¹H NMR (CDCl₃) δ 0.90 (3H, s, 4a-CH₃), 1.15 (3H, d, J=6.7 Hz, 5-CH₃), 1.91 (3H, d, J=2.2 Hz, 3-CH₃), 2.45 (1H, br d, J=15.9 Hz, 4-H), 2.77(1H, d, J=15.9 Hz, 4-H), 2.82 (1H, q, J=6.7 Hz, 5-H), 3.01 (1H, dd, J=23.3, 4.1 Hz, 7-H), 3.14 (3H, s, N—CH₃), 3.17 (1H, dd, J=23.3, 4.1 Hz, 7-H), 5.77 (1H, br t, J=4.1 Hz, 8-H), 5.79 (1H, s, 9-H); MS (EI) m/z 257 (M)⁺.

Example 112
(4aR,5R,6S)-6-Hydroxy-4a,5,6,7-tetrahydro-1,3,4a,5-tetramethylbenz[f]indol-2(4H)-one The compound (215 mg=0.84 mmol) prepared in Example 111 was dissolved in methanol (4 ml), sodium borohydride (63 mg=1.67 mmol) was added to the solution, the mixture was stirred at room temperature for 30 min. Water was added to the reaction mixture, and the solvent was removed under reduced pressure. The residue was purified by preparative TLC to give the title compound (190 mg, 88%).

¹H NMR (CDCl₃) δ 1.14 (3H, s, 4a-CH₃), 1.18 (3H, d, J=7.0 Hz, 5-CH₃), 1.74 (1H, dq, J=7.0, 2.7 Hz, 5-H), 1.85 (3H, d, J=2.0 Hz, 3-CH₃), 2.09 (1H, br d, J=16.0 Hz, 4-H), 2.40 (1H, br dd, J=20.5, 4.2 Hz, 7-H), 2.58 (1H, br ddd, J=20.5, 4.2 Hz, 7-H), 2.71 (1H, d, J=16.0 Hz, 4-H), 3.09 (3H, s, N—CH₃), 4.01 (1H, m, 6-H), 5.68 (1H, br t, J=4.2 Hz, 8-H), 5.74 (1H, s, 9-H); MS (EI) m/z 259 (M)⁺.

Example 113
(4aR,5R,6S)-6-Propionyloxy-4a,5,6,7-tetrahydro-1,3,4a,5-tetramethylbenz[f]indol-2(4H)-one The procedure of Example 3 was repeated, except that the compound (20 mg=0.08 mmol) prepared in Example 112 was dissolved in pyridine (0.4 ml), propionyl chloride (14 μl=0.22 mmol) was added to the solution, and the mixture was stirred at room temperature for 12 hr. Thus, the title compound (14 mg, 58%) was prepared.

$^1$H NMR (CDCl$_3$) δ 1.07 (3H, d, J=7.0 Hz, 5-CH$_3$), 1.11 (3H, t, J=7.5 Hz, OCOCH$_2$CH$_3$), 1.13 (3H, s, 4a-CH$_3$), 1.87 (3H, d, J=2.0 Hz, 3-CH$_3$), 1.88 (1H, dq, J=7.0, 2.7 Hz, 5-H), 2.11 (1H, br d, J=16.0 Hz, 4-H), 2.31 (2H, q, J=7.5 Hz, OCOCH$_2$CH$_3$), 2.52 (1H, br dd, J=20.5, 4.2 Hz, 7-H), 2.72 (1H, br ddd, J=20.5, 4.2 Hz, 7-H), 2.78 (1H, d, J=16.0 Hz, 4-H), 3.09 (3H, s, N—CH$_3$), 5.13 (1H, m, 6-H), 5.63 (1H, br t, J=4.2 Hz, 8-H), 5.73 (1H, s, 9-H); MS (EI) m/z 315 (M)$^+$.

Example 114
(4aR,5R,6S)-6-Benzoyloxy-4a,5,6,7-tetrahydro-1,3,4a,5-tetramethylbenz[f]indol-2(4H)-one The procedure of Example 3 was repeated, except that the compound (18 mg=0.07 mmol) prepared in Example 112 was dissolved in pyridine (0.4 ml), benzoyl chloride (16 μl=0.14 mmol) was added to the solution, and the mixture was stirred at room temperature for 12 hr. Thus, the title compound (14 mg, 56%) was prepared.

$^1$H NMR (CDCl$_3$) δ 1.15 (3H, d, J=7.0 Hz, 5-CH$_3$), 1.27 (3H, s, 4a-CH$_3$), 1.88 (3H, d, J=2.0 Hz, 3-CH$_3$), 2.02 (1H, dq, J=7.0, 2.7 Hz, 5-H), 2.18 (1H, br d, J=16.0 Hz, 4-H), 2.52 (1H, br dd, J=20.5, 4.2 Hz, 7-H), 2.72 (1H, br ddd, J=20.5, 4.2 Hz, 7-H), 2.84 (1H, d, J=16.0 Hz, 4-H), 3.11 (3H, s, N—CH$_3$), 5.40 (1H, m, 6-H), 5.68 (1H, br t, J=4.2 Hz, 8-H), 5.76 (1H, s, 9-H), 7.40–8.10 (5H, m, OCOC$_6$H$_5$); MS (EI) m/z 363 (M)$^+$.

Example 115
(4aR,5R,6S)-6-(Imidazol-1-ylcarbonyloxy)-4a,5,6,7-tetrahydro-1,3,4a,5-tetramethylbenz[f]indol-2(4H)-one The procedure of Example 5 was repeated, except that the compound (101 mg=0.39 mmol) prepared in Example 112 was dissolved in methylene chloride (2 ml), 1,1'-carbonyldiimidazole (143 mg=0.88 mmol) was added to the solution, and the mixture was stirred at room temperature for 3 hr. Thus, the title compound (130 mg, 95%) was prepared.

$^1$H NMR (CDCl$_3$) δ 1.21 (3H, d, J=7.0 Hz, 5-CH$_3$), 1.21 (3H, s, 4a-CH$_3$), 1.91 (3H, d, J=2.0 Hz, 3-CH$_3$), 2.08 (1H, dq, J=7.0, 2.6 Hz, 5-H), 2.20 (1H, br d, J=16.1 Hz, 4-H), 2.62 (1H, br dd, J=20.6, 4.7 Hz, 7-H), 2.79 (1H, br ddd, J=20.6, 4.7, 3.7 Hz, 7-H), 2.86 (1H, d, J=16.1 Hz, 4-H), 3.14 (3H, s, N—CH$_3$), 5.38 (1H, m, 6-H), 5.66 (1H, br t, J=3.7 Hz, 8-H), 5.76 (1H, s, 9-H), 7.09 (1H, br s, OCOC$_3$H$_3$N$_2$), 7.41 (1H, br s, OCOC$_3$H$_3$N$_2$), 8.12 (1H, br s, OCOC$_3$H$_3$N$_2$); MS (EI) m/z 353 (M)$^+$.

Example 116
(4aR,5R,6S)-6-Propylcarbamoyloxy-4a,5,6,7-tetrahydro-1,3,4a,5-tetramethylbenz[f]indol-2(4H)-one The procedure of Example 6 was repeated, except that the compound (40 mg=0.11 mmol) prepared in Example 115 was dissolved in toluene (0.8 ml), propylamine (94 μl=1.14 mmol) was added to the solution, and the mixture was stirred at room temperature for 2 hr and then at 50° C. for 2 hr, followed by purification by preparative TLC to give the title compound (35 mg, 89%).

$^1$H NMR (CDCl$_3$) δ 0.91 (3H, t, J=7.1 Hz, OCONHCH$_2$CH$_2$CH$_3$), 1.03 (3H, s, 4a-CH$_3$), 1.09 (3H, d, J=6.9 Hz, 5-CH$_3$), 1.53 (2H, seq, J=7.1 Hz, OCONHCH$_2$CH$_2$CH$_3$), 1.83 (1H, br q, J=6.9 Hz, 5-H), 1.85 (3H, br s, 3-CH$_3$), 2.10 (1H, br d, J=16.0 Hz, 4-H), 2.45 (1H, dd, J=20.4, 4.5 Hz, 7-H), 2.56 (1H, br ddd, J=20.4, 4.5 Hz, 7-H), 2.77 (1H, d, J=16.0 Hz, 4-H), 3.08 (3H, s, N—CH$_3$), 3.14 (2H, br dt, J=7 Hz, OCONHCH$_2$CH$_2$CH$_3$), 4.99 (1H, m, NH), 5.04 (1H, m, 6-H), 5.65 (1H, m, 8-H), 5.71 (1H, s, 9-H); MS (FAB) m/z 343 (M–H)$^+$.

Example 117
(4aR,5R,6S)-6-(Pyrrolidin-1-ylcarbonyloxy)-4a,5,6,7-tetrahydro-1,3,4a,5-tetramethylbenz[f]indol-2(4H)-one The procedure of Example 6 was repeated, except that the compound (40 mg=0.11 mmol) prepared in Example 115 was dissolved in toluene (0.8 ml), pyrrolidine (47 μl=0.56 mmol) was added to the solution, and the mixture was stirred at room temperature for 1 hr, followed by purification by preparative TLC to give the title compound (36 mg, 89%).

$^1$H NMR (CDCl$_3$) δ 1.11 (3H, d, J=7.2 Hz, 5-CH$_3$), 1.12 (3H, s, 4a-CH$_3$), 1.79–1.89 (4H, m, OCOC$_4$H$_8$N), 1.86 (3H, d, J=1.9 Hz, 3-CH$_3$), 1.89 (1H, dq, J=7.2, 2.7 Hz, 5-H), 2.12 (1H, br d, J=15.9 Hz, 4-H), 2.47 (1H, dd, J=20.5, 4.9 Hz, 7-H), 2.59 (1H, br ddd, J=20.5, 4.9 Hz, 7-H), 2.79 (1H, d, J=5.9 Hz, 4-H), 3.10 (3H, s, N—CH$_3$), 3.28 (2H, br t, J=6.7 Hz, OCOC$_4$H$_8$N), 3.38 (2H, br t, J=5.9 Hz, OCOC$_4$H$_8$N), 5.01 (1H, m, 6-H), 5.65 (1H, m, 8-H), 5.73 (1H, s, 9-H); MS (FAB) m/z 355 (M–H)$^+$.

Example 118
(4aR,5R,6R,7S)-6,7-Dihydroxy-1-ethyl-4a,5,6,7-tetrahydro-3,4a,5-trimethylbenz[f]indol-2(4H)-one A compound (300 mg=1.15 mmol) represented by the formula (III) was dissolved in methylene chloride (6 ml), and the solution was cooled to −15° C. Methanesulfonyl chloride (133 μl=1.73 mmol) was added to the solution in the presence of diisopropylethylamine (399 μl=2.29 mmol), and the mixture was stirred for 15 min. Methylene chloride (60 ml) was added to the reaction mixture, the mixture was washed with saturated saline (60 ml), and the solvent was removed under reduced pressure. A 2 M ethylamine/THF solution (3.5 ml) was added to the residue, and the mixture was stirred at room temperature for 24 hr. The solvent was removed under reduced pressure, the reaction product was dissolved in acetonitrile (15 ml), acetic acid (720 μl=12.0 mmol) was added to the solution, and the mixture was stirred at room temperature for 24 hr. Methylene chloride (60 ml) was added to the reaction mixture, the mixture was washed with a saturated aqueous sodium hydrogencarbonate solution (60 ml×2) and saturated saline (60 ml), and the organic phase was dried over sodium sulfate. The residue was purified by preparative TLC to give the title compound (170 mg, 51%).

$^1$H NMR (CDCl$_3$) δ 1.14 (3H, t, J=7.4 Hz, N—CH$_2$CH$_3$), 1.15 (3H, s, 4a-CH$_3$), 1.20 (3H, d, J=7.1 Hz, 5-CH$_3$), 1.75 (1H, dq, J=7.1, 1.7 Hz, 5-H), 1.83 (3H, d, J=1.7 Hz, 3-CH$_3$), 2.06 (1H, br d, J=15.9 Hz, 4-H), 2.76 (1H, d, J=15.9 Hz, 4-H), 3.59 (2H, m, N—CH$_2$CH$_3$), 3.89 (1H, m, 6-H), 4.36 (1H, m, 7-H), 5.72 (1H, s, 9-H), 5.57 (1H, s, 8-H); MS (EI)m/z 289 (M)$^+$; [α]$^{20}_D$ −140° (c 1.0, MeOH).

Example 119
(4aR,5R,6R,7R)-1-Ethyl-6-hydroxy-7-methoxy-4a,5,6,7-tetrahydro-3,4a,5-trimethylbenz[f]indol-2(4H)-one A compound (300 mg=1.15 mmol) represented by the formula (III) was dissolved in methylene chloride (6 ml), and the solution was cooled to −15° C. Methanesulfonyl chloride (133 μl=1.73 mmol) was added to the reaction mixture in the presence of diisopropylethylamine(399

μl=2.29 mmol), and the mixture was stirred for 15 min. Methylene chloride (60 ml) was added to the reaction mixture, the mixture was washed with saturated saline (60 ml), and the solvent was removed under reduced pressure. A 2 M ethylamine/THF solution (3.5 ml) was added to the residue, and the mixture was stirred at room temperature for 24 hr. The solvent was removed under reduced pressure, and the reaction product was dissolved in acetonitrile (15 ml), acetic acid (720 μl=12.0 mmol) was added to the solution, and the mixture was stirred at room temperature for 24 hr. Methylene chloride (60 ml) was added to the reaction mixture, the mixture was washed with a saturated aqueous sodium hydrogencarbonate solution (60 ml×2) and saturated saline (60 ml), and the organic phase was dried over sodium sulfate. The solvent was removed under reduced pressure, methanol (30 ml) was added to the reaction product, and the mixture was stirred at 50° C. for 3 hr. The solvent was removed under reduced pressure, and the residue was purified by preparative TLC to give the title compound (100 mg, 29%).

$^1$H NMR (CDCl$_3$) δ 1.10 (3H, 5, 4a-CH$_3$), 1.16 (3H, t, J=7.2 Hz, N—CH$_2$CH$_3$), 1.17 (3H, d, J=7.3 Hz, 5-CH$_3$), 1.84 (3H, d, J=1.9 Hz, 3-CH$_3$), 1.90 (1H, dq, J=7.3, 2.7 Hz, 5-H), 2.12 (1H, br d, J=15.9 Hz, 4-H), 2.77 (1H, d, J=15.9 Hz, 4-H), 3.42 (3H, s, O—CH$_3$), 3.57 (1H, dq, J=7.1, 7.2 Hz, N—CH$_2$CH$_3$), 3.62 (1H, dq, J=7.1, 7.2 Hz, N—CH$_2$CH$_3$), 3.70 (1H, dd, J=4.8, 1.7 Hz, 7-H), 3.90 (1H, br s, 6-H), 5.75 (1H, s, 9-H), 5.80 (1H, d, J=4.8 Hz, 8-H); MS (EI) m/z 303 (M)$^+$; [α]$^{18}_D$ −414° (c 1.0, MeOH); mp 151–154° C.

Example 120

(4aR,5R,6R,7R)-1-Ethyl-7-methoxy-6-propionyloxy-4a,5,6,7-tetrahydro-3,4a,5-trimethylbenz[f]indol-2(4H)-one The compound (34 mg=0.11 mmol) prepared in Example 119 was dissolved in pyridine (1 ml), propionyl chloride (34 μl=0.55 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (12 mg, 30%).

$^1$H NMR (CDCl$_3$) δ 1.08 (3H, d, J=7.3 Hz, 5-CH$_3$), 1.09 (3H, s, 4a-CH$_3$), 1.14 (3H, t, J=7.5 Hz, OCOCH$_2$CH$_3$), 1.15 (3H, t, J=7.2 Hz, N—CH$_2$CH$_3$), 1.86 (3H, d, J=1.9 Hz, 3-CH$_3$), 2.08 (1H, dq, J=7.3, 2.7 Hz, 5-H), 2.14 (1H, br d, J=15.9 Hz, 4-H), 2.34 (2H, q, J=7.5 Hz, OCOCH$_2$CH$_3$), 2.80 (1H, d, J=15.9 Hz, 4-H), 3.50 (3H, s, O—CH$_3$), 3.60 (1H, dd, J=4.8, 1.7 Hz, 7-H), 3.61 (2H, m, N—CH$_2$CH$_3$), 5.09 (1H, m, 6-H), 5.73 (1H, s, 9-H), 5.74 (1H, d, J=4.8 Hz, 8-H); MS (EI) m/z 359 (M)$^+$; [α]$^{18}_D$ −228° (c 1.0, MeOH).

Example 121

(4aR,5R,6R,7R)-1-Ethyl-6-(2-furancarbonyloxy)-7-methoxy-4a,5,6,7-tetrahydro-3,4a,5-trimethylbenz[f]indol-2(4H)-one The compound (28 mg=0.09 mmol) prepared in Example 119 was dissolved in pyridine (1 ml), 2-furoyl chloride (27 μl=0.27 mmol) was added to the solution, and the mixture was stirred at room temperature for 24 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (31 mg, 85%).

$^1$H NMR (CDCl$_3$) δ 1.15 (3H, d, J=7.3 Hz, 5-CH$_3$), 1.16 (3H, t, J=7.2 Hz, N—CH$_2$CH$_3$), 1.87 (3H, d, J=1.9 Hz, 3-CH$_3$), 1.21 (3H, s, 4a-CH$_3$), 2.17 (1H, dq, J=7.3, 2.7 Hz, 5-H), 2.18 (1H, br d, J=15.9 Hz, 4-H), 2.83 (1H, d, J=15.9 Hz, 4-H), 3.55 (3H, s, O—CH$_3$), 3.59 (1H, dq, J=7.0, 7.2 Hz, N—CH$_2$CH$_3$), 3.66 (1H, dq, J=7.0, 7.2 Hz, N—CH$_2$CH$_3$), 3.73 (1H, br d, J=4.8 Hz, 7-H), 5.29 (1H, br s, 6-H), 5.75 (1H, s, 9-H), 5.76 (1H, d, J=4.8 Hz, 8-H), 6.49 (1H, dd, J=3.5, 1.7 Hz, OCOC$_4$H$_3$O), 7.11 (1H, dd, J=3.5, 0.8 Hz, OCOC$_4$H$_3$O), 7.57 (1H, dd, J=1.7, 0.8 Hz, OCOC$^+$; OCOC$_4$H$_3$O); MS (EI) m/z 397 (M)$^+$; [α]$^{18}_D$ −17° (c 1.0, MeOH).

Example 122

(4aR, 5R, 6R, 7R)-1-Benzyl-6-hydroxy-7-methoxy-4a,5,6,7-tetrahydro-3,4a,5-trimethylbenz[f]indol-2(4H)-one A compound (70 mg=0.27 mmol) represented by the formula (III) was dissolved in methylene chloride (1.4 ml), and the solution was cooled to −15° C. Methanesulfonyl chloride (31 μl=0.40 mmol) was added to the reaction mixture in the presence of diisopropylethylamine (93 μl=0.53 mmol), and the mixture was stirred for 15 min. Methylene chloride (10 ml) was added to the reaction mixture, the mixture was washed with saturated saline (10 ml), and the solvent was removed under reduced pressure. A 2 M benzylamine/THF solution (267 μl) was added to the residue, and the mixture was stirred at room temperature for 4 hr. The solvent was removed under reduced pressure, and the reaction product was dissolved in acetonitrile (3.5 ml), acetic acid (160 μl=2.7 mmol) was added to the solution, and the mixture was stirred at room temperature for 20 hr. Methylene chloride (10 ml) was added to the reaction mixture, the mixture was washed with a saturated aqueous sodium hydrogencarbonate solution (10 ml×2) and saturated saline (10 ml), and the organic phase was dried over sodium sulfate. The solvent was removed under reduced pressure, methanol (7 ml) was added to the reaction product, and the mixture was stirred at 60° C. for 5 hr. The solvent was removed under reduced pressure, and the residue was purified by preparative TLC to give the title compound (9 mg, 9%).

$^1$H NMR (CDCl$_3$) δ 1.08 (3H, s, 4a-CH$_3$), 1.17 (3H, d, J=7.4 Hz, 5-CH$_3$), 1.88 (1H, dq, J=7.4, 2.5 Hz, 5-H), 1.91 (3H, d, J=1.8 Hz, 3-CH$_3$), 2.14 (1H, br d, J=15.9 Hz, 4-H), 2.79 (1H, d, J=15.9 Hz, 4-H), 3.38 (3H, s, O—CH$_3$), 3.64 (1H, dd, J=4.8, 1.9 Hz, 7-H), 3.88 (1H, br s, 6-H), 4.69 (1H, d, J=15.9 Hz, N—CH$_2$C$_6$H$_5$), 4.87 (1H, d, J=15.9 Hz, N—CH$_2$C$_6$H$_5$), 5.64 (1H, s, 9-H), 5.70 (1H, d, J=4.8 Hz, 8-H), 7.16–7.30 (5H, m, N—CH$_2$C$_6$H$_5$); MS (EI)m/z 365 (M)$^+$; [α]$^{20}_D$ −354° (c 1.0, MeOH); mp 45° C.

Example 123

(4aR,5R,6R,7R)-1-Benzyl-6-(2-furancarbonyloxy)-7-methoxy-4a,5,6,7-tetrahydro-3,4a,5-trimethylbenz[f]indol-2(4H)-one The compound (23 mg=0.06 mmol) prepared in Example 122 was dissolved in pyridine (1 ml), 2-furoyl chloride (19 μl=0.19 mmol) was added to the solution, and the mixture was stirred at room temperature for 16 hr. Methylene chloride (20 ml) was added to the reaction mixture, the mixture was washed with a saturated aqueous sodium hydrogencarbonate solution (20 ml×2) and saturated saline (20 ml), and the solvent was removed under reduced pressure. The organic phase was dried over sodium sulfate, and the solvent was removed under reduced pressure. The residue was purified by preparative TLC to give the title compound (30 mg, 100%).

$^1$H NMR (CDCl$_3$) δ 1.14 (3H, d, J=7.1 Hz, 5-CH$_3$), 1.19 (3H, s, 4a-CH$_3$), 1.93 (3H, d, J=1.8 Hz, 3-CH$_3$), 2.14 (1H, dq, J=7.1, 2.8 Hz, 5-H), 2.19 (1H, br d, J=15.9 Hz, 4-H), 2.85 (1H, d, J=15.9 Hz, 4-H), 3.52 (3H, s, O—CH$_3$), 3.68 (1H, dd, J=4.7, 1.1 Hz, 7-H), 4.69 (1H, d, J=15.9 Hz, N—C̲H$_2$C$_6$H$_5$), 4.91 (1H, d, J=15.9 Hz, N—C̲H$_2$C$_6$H$_5$), 5.27 (1H, m, 6-H), 5.65 (1H, s, 9-H), 5.66 (1H, d, J=4.8 Hz, 8-H), 6.49 (1H, dd, J=3.5, 1.7 Hz, OCOC$_4$H$_3$O), 7.09 (1H, dd, J=3.5, 0.8 Hz, OCOC$_4$H$_3$O), 7.17–7.32 (5H, m, N—CH$_2$ C̲$_6$H$_5$), 7.56 (1H, dd, J=1.7, 0.8 Hz, OCOC$_4$H$_3$O); MS (EI)m/z 459 (M)$^+$; [α]$^{20}_D$ −30° (c 1.0, MeOH).

Example 124
(4aR,5R,6R,7R)-6-Hydroxy-7-methoxy-1-(4-methoxybenzyl)-4a,5,6,7-tetrahydro-3,4a,5-trimethylbenz[f]indol-2(4H)-one A compound (100 mg=0.38 mmol) represented by the formula (III) was dissolved in methylene chloride (2 ml), and the solution was cooled to −15° C. Methanesulfonyl chloride (44 μl=0.57 mmol) was added to the reaction mixture in the presence of diisopropylethylamine (133 μl=0.76 mmol), and the mixture was stirred for 15 min. Methylene chloride (10 ml) was added thereto, the mixture was washed with saturated saline (10 ml), and the solvent was removed under reduced pressure. A 2 M 4-methoxybenzylamine/THF solution (955 μl) was added to the residue, and the mixture was stirred at room temperature for 5 hr. The solvent was removed under reduced pressure, the reaction product was dissolved in acetonitrile (5 ml), acetic acid (230 μl=3.79 mmol) was added to the reaction solution, and the mixture was stirred at room temperature for 16 hr. Methylene chloride (10 ml) was added to the reaction mixture, the mixture was washed with a saturated aqueous sodium hydrogencarbonate solution (10 ml×2) and saturated saline (10 ml), and the organic phase was dried over sodium sulfate. The solvent was removed under reduced pressure, and methanol (10 ml) was added to the reaction product, and the mixture was stirred at 50° C. for 5 hr. The solvent was removed under reduced pressure, and the residue was purified by preparative TLC to give the title compound (30 mg, 20%).

$^1$H NMR (CDCl$_3$) δ 1.07 (3H, s, 4a-CH$_3$), 1.17 (3H, d, J=7.3 Hz, 5-CH$_3$), 1.87 (1H, dq, J=7.3, 2.5 Hz, 5-H), 1.89 (3H, d, J=1.7 Hz, 3-CH$_3$), 2.12 (1H, br d, J=15.9 Hz, 4-H), 2.78 (1H d, J=15.9 Hz, 4-H), 3.39 (3H, s, O—CH$_3$), 3.65 (1H, dd, J=4.7, 1.7 Hz, 7-H), 3.76 (3H, s, N—CH$_2$C$_6$H$_4$O CH$_3$), 3.88 (1H, br s, 6-H), 4.62 (1H, d, J=15.7 Hz, N—C̲H$_2$C$_6$H$_4$OCH$_3$), 4.80 (1H, d, J=15.7 Hz, N—C̲H$_2$C$_6$H$_4$OCH$_3$), 5.66 (1H, s, 9-H), 5.71 (1H, d, J=4.7 Hz, 8-H), 6.80 (2H, d, J=8.8 Hz, N—CH$_2$C$_6$H$_4$OCH$_3$), 7.11 (2H, d, J=8.8 Hz, N—CH$_2$C$_6$H$_4$OCH$_3$); MS (FAB) m/z 396 (M+H)$^+$; [α]$^{20}_D$ −175° (c 1.0, MeOH).

The structures of the respective compounds prepared in the above examples are summarized below.

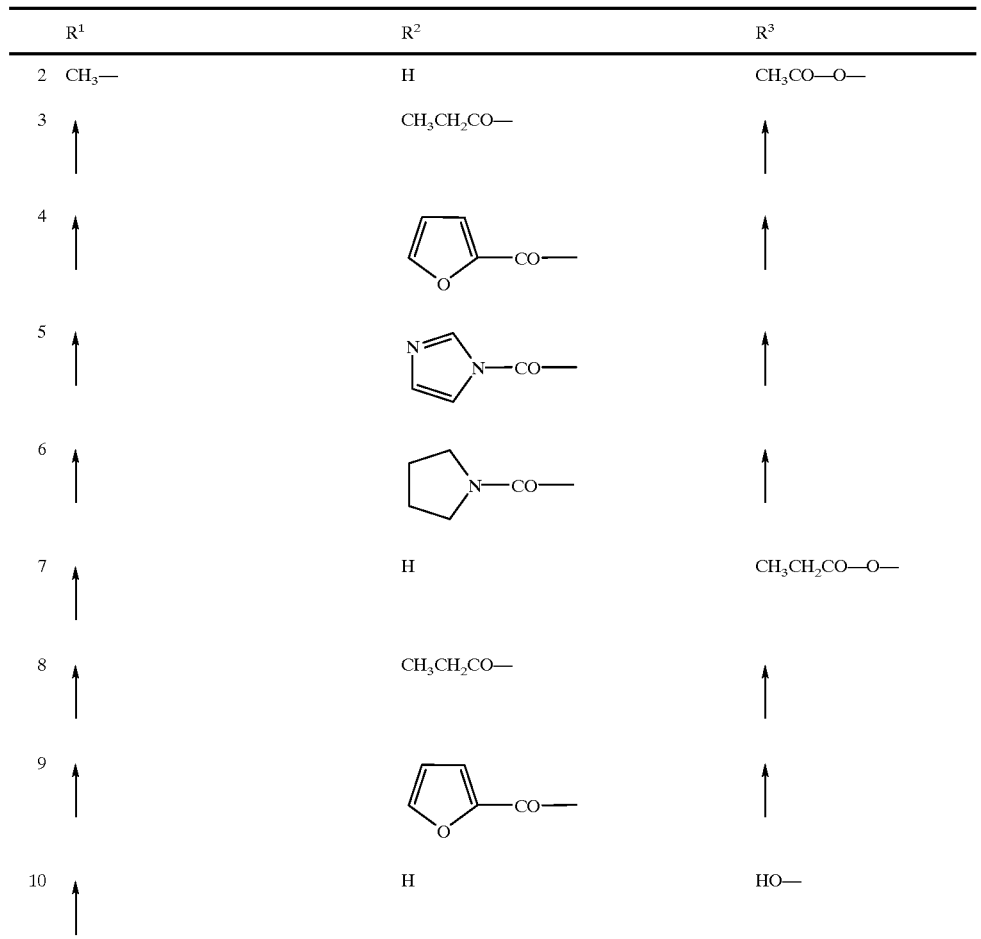

-continued

| | R¹ | R² | R³ |
|---|---|---|---|
| 11 | ↑ | H | (CH₃)₃C—Si(CH₃)₂—O— |
| 12 | ↑ | CH₃CO— | HO— |
| 13 | CH₃— | CH₃CH₂CO— | HO— |
| 14 | ↑ | (cyclopropyl)-CO— | ↑ |
| 15 | ↑ | (cyclohexyl)-CO— | ↑ |
| 16 | ↑ | (phenyl)-CO— | ↑ |
| 17 | ↑ | (2-furyl)-CO— | ↑ |
| 18 | ↑ | CH₃(CH₂)₃— | ↑ |
| 19 | ↑ | (CH₃)₂CH(CH₂)₂— | ↑ |
| 20 | ↑ | (cyclopropyl)-CH₂— | ↑ |
| 21 | ↑ | CH₂=CH—CH₂— | ↑ |
| 22 | ↑ | CH₃(CH₂)₂—NH—CO— | ↑ |
| 23 | ↑ | (pyrrolidin-1-yl)-CO— | ↑ |
| 24 | CH₃— | H | CH₃—O— |
| 25 | ↑ | CH₃CO— | ↑ |
| 26 | ↑ | CH₃CH₂CO— | ↑ |
| 27 | ↑ | (cyclopropyl)-CO— | ↑ |

-continued
| | R¹ | R² | R³ |
|---|---|---|---|
| 28 | ↑ | 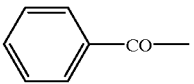 | ↑ |
| 29 | ↑ | 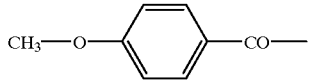 | ↑ |
| 30 | ↑ | 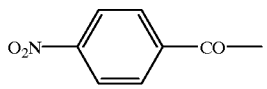 | ↑ |
| 31 | ↑ | 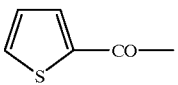 | ↑ |
| 32 | ↑ | 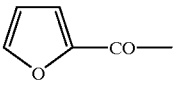 | ↑ |
| 33 | ↑ | 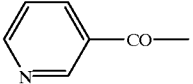 | ↑ |
| 34 | ↑ | $CH_3-$ | ↑ |
| 35 | $CH_3-$ | $CH_3CH_2-$ | $CH_3-O-$ |
| 36 | ↑ | $CH_3(CH_2)_2-$ | ↑ |
| 37 | ↑ | $CH_3(CH_2)_3-$ | ↑ |
| 38 | ↑ | $(CH_3)_2CH(CH_2)_2-$ | ↑ |
| 39 | ↑ | $CH_3CH_2(CH_3)CHCH_2-$ | ↑ |
| 40 | ↑ | 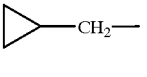 | ↑ |
| 41 | ↑ | $CH_2=CH-CH_2-$ | ↑ |
| 42 | ↑ | 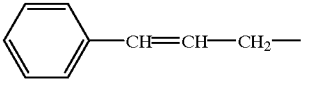 | ↑ |
| 43 | ↑ | 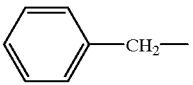 | ↑ |

-continued

| | R¹ | R² | R³ |
|---|---|---|---|
| 44 | ↑ | CH₃—O—⟨phenyl⟩—CH₂— | ↑ |
| 45 | ↑ | (HO)₂CHCH₂— | ↑ |
| 46 | CH₃— | HO—(CH₂)₂— | CH₃—O— |
| 47 | ↑ | ⟨imidazol-1-yl⟩—CO— | ↑ |
| 48 | ↑ | H₂N—CO— | ↑ |
| 49 | ↑ | CH₃NH—CO— | ↑ |
| 50 | ↑ | C₂H₅NH—CO— | ↑ |
| 51 | ↑ | CH₃(CH₂)₂NH—CO— | ↑ |
| 52 | ↑ | (CH₃)₂CHNH—CO— | ↑ |
| 53 | ↑ | (CH₃)₂CHCH₂NH—CO— | ↑ |
| 54 | ↑ | CH₃(CH₂)₅NH—CO— | ↑ |
| 55 | ↑ | ⟨cyclopropyl⟩—NH—CO— | ↑ |
| 56 | ↑ | ⟨phenyl⟩—CH₂—NH—CO— | ↑ |
| 57 | CH₃— | ⟨phenyl⟩—NH—CO— | CH₃—O— |
| 58 | ↑ | HO—(CH₂)₂—NH—CO— | ↑ |
| 59 | ↑ | (C₂H₅)₂N—CO— | ↑ |
| 60 | ↑ | ⟨pyrrolidin-1-yl⟩—CO— | ↑ |

-continued

| | R¹ | R² | R³ |
|---|---|---|---|
| 61 | ↑ | piperidine-N-CO— | ↑ |
| 62 | ↑ | 2-(methoxymethyl)pyrrolidine-N-CO— (CH₃—O—CH₂ substituent) | ↑ |
| 63 | ↑ | 4-ethylpiperazine-N-CO— (C₂H₅—N piperazine N—CO—) | ↑ |
| 64 | ↑ | morpholine-N-CO— | ↑ |
| 65 | ↑ | C₂H₅O—CO— | ↑ |
| 66 | ↑ | C₆H₅—O—CO— | ↑ |
| 67 | ↑ | imidazole-N—C(=S)— | ↑ |
| 68 | CH₃— | CH₃(CH₂)₂NH—C(=S)— | CH₃O— |
| 69 | ↑ | pyrrolidine-N—C(=S)— | ↑ |
| 70 | ↑ | H | C₂H₅O— |
| 71 | ↑ | CH₃CO— | ↑ |
| 72 | ↑ | C₂H₅CO— | ↑ |
| 73 | ↑ | furan-2-CO— | ↑ |
| 74 | ↑ | (CH₃)₂CH(CH₂)₂— | ↑ |
| 75 | ↑ | imidazole-N—CO— | ↑ |

-continued
| | R¹ | R² | R³ |
|---|---|---|---|
| 76 | ↑ | CH₃(CH₂)₂NH—CO— | ↑ |
| 77 | ↑ | H | (CH₃)₂CH—O— |
| 78 | ↑ | C₂H₅CO— | ↑ |
| 79 | CH₃— | 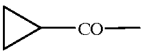—CO— | (CH₃)₂CH—O— |
| 80 | ↑ | 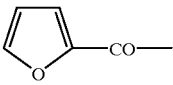—CO— | ↑ |
| 81 | ↑ | 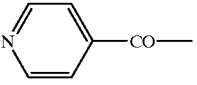—CO— | ↑ |
| 82 | ↑ | C₂H₅— | ↑ |
| 83 | ↑ | CH₃(CH₂)₂— | ↑ |
| 84 | ↑ | CH₃(CH₂)₃— | ↑ |
| 85 | ↑ | (CH₃)₂CH(CH₂)₂— | ↑ |
| 86 | ↑ | 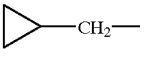—CH₂— | ↑ |
| 87 | ↑ | 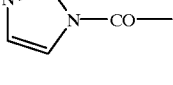—CO— | ↑ |
| 88 | ↑ | CH₃NHCO— | ↑ |
| 89 | ↑ | CH₃(CH₂)₂NHCO— | ↑ |
| 90 | CH₃— | H | (CH₃)₂CHCH₂—O— |
| 91 | ↑ | 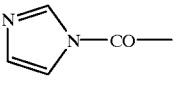—CO— | ↑ |
| 92 | ↑ | CH₃(CH₂)₂NHCO— | ↑ |

-continued
| | R¹ | R² | R³ |
|---|---|---|---|
| 93 | ↑ | H | 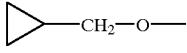—CH₂—O— |
| 94 | ↑ | 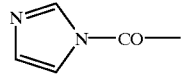—CO— | ↑ |
| 95 | ↑ | CH₃(CH₂)₂NHCO— | 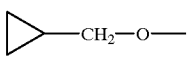—CH₂—O— |
| 96 | ↑ | H | CH₃—S— |
| 97 | ↑ | C₂H₅CO— | ↑ |
| 98 | ↑ | 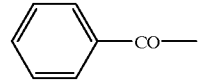—CO— | ↑ |
| 99 | ↑ | 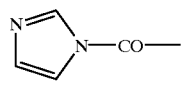—CO— | ↑ |
| 100 | ↑ | H | C₂H₅—S— |
| 101 | CH₃— | C₂H₅CO— | C₂H₅—S— |
| 102 | ↑ | 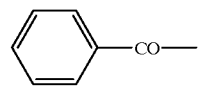—CO— | ↑ |
| 103 | ↑ | CH₃(CH₂)₃— | ↑ |
| 104 | ↑ | (CH₃)₂CH(CH₂)₂— | ↑ |
| 105 | ↑ | 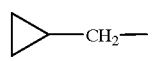—CH₂— | ↑ |
| 106 | ↑ | 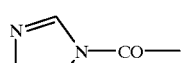—CO— | ↑ |
| 107 | ↑ | CH₃(CH₂)₂NHCO— | ↑ |
| 108 | ↑ | 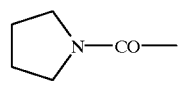—CO— | ↑ |

-continued

| | R¹ | R² | R³ |
|---|---|---|---|
| 109 | ↑ | H | C₆H₅—S— |
| 110 | ↑ | C₂H₅CO— | ↑ |
| 112 | CH₃— | H | H |
| 113 | ↑ | C₂H₅CO— | H |
| 114 | ↑ | C₆H₅—CO— | H |
| 115 | ↑ | (imidazol-1-yl)—CO— | H |
| 116 | ↑ | CH₃(CH₂)₂NHCO— | H |
| 117 | ↑ | (pyrrolidin-1-yl)—CO— | H |
| 118 | C₂H₅— | H | HO— |
| 119 | ↑ | H | CH₃O— |
| 120 | ↑ | C₂H₅CO— | ↑ |
| 121 | ↑ | (furan-2-yl)—CO— | ↑ |
| 122 | C₆H₅—CH₂— | H | CH₃O— |
| 123 | ↑ | (furan-2-yl)—CO— | ↑ |
| 124 | CH₃O—C₆H₄—CH₂— | H | ↑ |

Preparation

Tablets

An intimate powder mixture of the compound prepared in Example 8, lactose, crosslinked polyvidone, and hydroxypropylmethyl cellulose was prepared and wet-granulated by a conventional method, and magnesium stearate in an amount of 0.5 mg/tablet was added thereto.

The resultant mixture was compressed by a conventional method to prepare tablets. Each tablet had the following composition.

| | |
|---|---|
| Compound of Example 8 | 5.0 mg |
| Lactose | 185 mg |
| Crosslinked polyvidone | 7.0 mg |
| Hydroxypropylmethyl cellulose | 2.5 mg |
| Magnesium stearate | 0.5 mg |
| | 200 mg |

Biological Activity

The progesterone receptor binding activity of the compounds of the present invention was measured in the following manner in accordance with the method of H. Kondo et. al. (J. Antibiotics, Vol. 43, pp. 1533–1542, 1990).

Uteri taken from hogs in 5 mM phosphate buffer were disrupted using Polytron homogenizer, and the resulting solution was centrifuged (100,000×g, 30 min) to separate the supernatant, thereby preparing a cytosol containing progesterone receptor. A given concentration of a test drug solution (10 μl) was added to a solution composed of 50 μl of the cylosol obtained just above (2–3 mg protein/ml) and 40 μl of a solution of [$^3$H]-progesterone as a ligand (3.84 TBq/mmol, 18.5 kBq/ml), and they were incubated in a test, tube for 60 min at 4° C. to effect a reaction. Then, 100 μl of a 0.5% activated carbon solution was added to the reaction solution, and the mixture was allowed to stand for 10 min and then centrifuged (2,000×g, 10 min). The radioactivity of the supernatant was measured with a liquid scintillation counter.

Separately, the radioactivity was measured in the same manner as described above, except that no test drug was added. Further, the radioactivity was measured in the same manner as described above, except that 10 μl of Medroxyprogesterone Acetate (MPA) (10 μg/ml) was added instead of the test drug. The radioactivity with no test drug added was defined as the amount of total binding of [$^3$H]-progesterone to the cytosol, and the radioactivity with MPA added was defined as the amount of non-specific binding. The inhibition ratio was calculated from these measured values by the following equation to determine the binding inhibitory activity (IC$_{50}$).

Inhibition ratio (%)=

$$\text{Inhibition ratio }(\%) = \left\{ 1 - \frac{(\text{total binding amount with test drug added}) - (\text{non-specific binding amount})}{(\text{total binding amount with no test drug added}) - (\text{non-specific binding amount})} \right\} \times 100$$

The compounds prepared in Examples 3, 4, 25, 26, 31, 32, 34, 35, 36, 41, 97, 99, 100, 101, 106, 107, 108, 113, 115, 116, and 117 and Mifepristone (RU38486) had the following inhibitory activity against progesterone receptor binding.

TABLE 1

| Inhibitory activity against progesterone receptor binding | |
|---|---|
| Ex. No. of compound | Inhibitory activity (IC$_{50}$) (nM) |
| 3 | 28 |
| 4 | 32 |

TABLE 1-continued

| Inhibitory activity against progesterone receptor binding | |
|---|---|
| Ex. No. of compound | Inhibitory activity (IC$_{50}$) (nM) |
| 25 | 25 |
| 26 | 17 |
| 31 | 47 |
| 32 | 27 |
| 34 | 42 |
| 35 | 36 |
| 36 | 51 |
| 41 | 44 |
| 97 | 64 |
| 99 | 66 |
| 100 | 119 |
| 101 | 164 |
| 106 | 137 |
| 107 | 156 |
| 108 | 155 |
| 113 | 99 |
| 115 | 22 |
| 116 | 19 |
| 117 | 31 |
| RU38486 | 106 |

Test on Toxicity upon Continuous Administration

A homogeneous suspension of the compound, according to the present invention, prepared in Example 8 in a 0.2% aqueous methyl cellulose solution was subcutaneously administered to 16 week-old male SD rats (five rats). The dose of the compound prepared in Example 8 was 60 mg/kg. All the rats remained survived without no special symptom.

Chemical Stability Test

In order to evaluate the chemical stability of the compound according to the present invention, a test on comparison of the compound (a) prepared in Example 24 with 3β-hydroxy-2α-methoxy-1(10),7(11),8-eremophilatrien-12,8-olide (b) (a compound prepared in WO 97/30040) which is a compound provided by replacing the nitrogen atom in the compound (a) with an oxygen atom was performed. In this comparison test, a change of the compounds (a) and (b) with the elapse of time was traced.

The test was performed by the following method.

The compounds (a) and (b) (each 1.0 mg) were accurately weighed and each dissolved in 2.0 ml of methanol to prepare methanol solutions. An aqueous NaOH solution (2.0 ml), which had been previously accurately adjusted to pH 11.5, was added to each of the methanol solutions, and the amount of the residual compounds (a) and (b) was traced with the elapse of time by liquid chromatography (data processing device: Shimadzu CHROMATOPAC C-R4A, detector: Shimadzu LC-6A, column: GL Science Inertsil ODS 4.6×100 mm, mobile phase: a 2:1 solution mixture of a buffer, prepared by adding 1000 ml of deionized water to 770 ml of ammonium acetate and 175 ml of dipotassium phosphate and adjusting the mixture to pH 6.5 by addition of phosphoric acid, and acetonitrile, detection wavelength: 323 nm for the compound (a) and 320 nm for the compound (b), temperature: 25° C., flow rate: 1 ml/min). The initial amount (time 0)of the compounds (a) and (b) was presumed to be 100% to determine the percentage of the residual compounds (a) and (b). The results were as shown in FIG. 1.

As is apparent from the results shown in FIG. 1, the novel mother nucleus according to the present invention has much better chemical stability than compounds having a ligularenolide type sesquiterpene mother nucleus with a lactone ring structure in its molecule.

What is claimed is:

1. A compound represented by the following formula (I) or a pharmaceutically acceptable salt thereof:

$$\text{(I)}$$

[Chemical structure with substituents $R^1$, $R^2O$, $R^3$, Me, Me, Me, and =O]

wherein
$R^1$ represents
a hydrogen atom,
optionally substituted $C_1$–$C_{10}$ alkyl,
optionally substituted $C_2$–$C_{10}$ alkenyl,
optionally substituted $C_2$–$C_{10}$ alkynyl,
optionally substituted $C_3$–$C_{10}$ cycloalkyl, or
optionally substituted $C_7$–$C_{15}$ aralkyl;
$R^2$ represents
a hydrogen atom,
optionally substituted $C_1$–$C_{10}$ alkylcarbonyl,
optionally substituted $C_2$–$C_{10}$ alkenylcarbonyl,
optionally substituted $C_2$–$C_{10}$ alkynylcarbonyl,
optionally substituted $C_3$–$C_{15}$ cycloalkylcarbonyl,
optionally substituted $C_7$–$C_{15}$ aralkylcarbonyl,
optionally substituted $C_7$–$C_{15}$ aromatic acyl,
optionally substituted $C_2$–$C_{15}$ heteroaromatic acyl having at least one hetero atom selected from the group consisting of nitrogen, oxygen, and sulfur atoms,
optionally substituted $C_3$–$C_{15}$ saturated heterocyclic acyl having at least one hetero atom selected from the group consisting of nitrogen, oxygen, and sulfur atoms,
optionally substituted $C_1$–$C_{10}$ alkyl,
optionally substituted $C_2$–$C_{10}$ alkenyl,
optionally substituted $C_2$–$C_{10}$ alkynyl,
optionally substituted $C_3$–$C_{10}$ cycloalkyl,
optionally substituted $C_7$–$C_{15}$ aralkyl, carbamoyl,
optionally substituted N—$C_1$–$C_{10}$ alkylcarbamoyl,
optionally substituted N—$C_6$–$C_{15}$ aromatic carbamoyl,
optionally substituted N—$C_7$–$C_{15}$ aralkylcarbamoyl,
optionally substituted N,N-di-$C_1$–$C_{10}$ alkylaminocarbonyl,
optionally substituted N—$C_3$–$C_{10}$ cycloalkylcarbamoyl,
optionally substituted $C_1$–$C_{10}$ alkoxycarbonyl,
optionally substituted $C_6$–$C_{15}$ aryloxycarbonyl,
optionally substituted $C_7$–$C_{15}$ aralkyloxycarbonyl,
optionally substituted $C_1$–$C_{15}$ heteroaromatic thiocarbonyl having at least one hetero atom selected from the group consisting of nitrogen, oxygen, and sulfur atoms,
optionally substituted $C_2$–$C_{15}$ saturated heterocyclic thiocarbonyl having at least one hetero atom selected from the group consisting of nitrogen, oxygen, and sulfur atoms, or
optionally substituted N—$C_1$–$C_{10}$ alkylthiocarbamoyl; and
$R^3$ represents
a hydrogen atom,
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
optionally substituted $C_3$–$C_{10}$ cycloalkyloxy,
optionally substituted $C_7$–$C_{15}$ aralkyloxy,
optionally substituted $C_1$–$C_{10}$ alkylcarbonyloxy,
optionally substituted $C_2$–$C_{10}$ alkenylcarbonyloxy,
optionally substituted $C_2$–$C_{10}$ alkynylcarbonyloxy,
optionally substituted $C_3$–$C_{10}$ cycloalkylcarbonyloxy,
optionally substituted $C_7$–$C_{15}$ aromatic acyloxy,
optionally substituted $C_7$–$C_{15}$ aralkylcarbonyloxy,
optionally substituted $C_1$–$C_{10}$ alkylthio,
optionally substituted $C_2$–$C_{10}$ alkenylthio,
optionally substituted $C_2$–$C_{10}$ alkynylthio,
optionally substituted $C_3$–$C_{10}$ cycloalkylthio,
optionally substituted $C_6$–$C_{15}$ arylthio, or
optionally substituted $C_7$–$C_{15}$ aralkylthio.

2. The compound or pharmaceutically acceptable salt thereof according to claim 1, wherein
$R^1$ represents
optionally substituted $C_1$–$C_{10}$ alkyl or
optionally substituted $C_7$–$C_{15}$ aralkyl;
$R^2$ represents
a hydrogen atom,
optionally substituted $C_1$–$C_{10}$ alkylcarbonyl,
optionally substituted $C_3$–$C_{10}$ cycloalkylcarbonyl,
optionally substituted $C_7$–$C_{15}$ aromatic acyl,
optionally substituted $C_2$–$C_{15}$ heteroaromatic acyl having at least one hetero atom selected from the group consisting of nitrogen, oxygen, and sulfur atoms,
optionally substituted $C_3$–$C_{15}$ saturated heterocyclic acyl having at least one hetero atom selected from the group consisting of nitrogen, oxygen, and sulfur atoms,
optionally substituted $C_1$–$C_{10}$ alkyl,
optionally substituted $C_2$–$C_{10}$ alkenyl,
optionally substituted $C_7$–$C_{15}$ aralkyl, carbamoyl,
optionally substituted N—$C_1$–$C_{10}$ alkylcarbamoyl,
optionally substituted N—$C_6$–$C_{15}$ aromatic carbamoyl,
optionally substituted N—$C_7$–$C_{15}$ aralkylcarbamoyl,
optionally substituted N,N-di-$C_1$–$C_{10}$ alkylaminocarbonyl,
optionally substituted N—$C_3$–$C_{10}$ cycloalkylcarbamoyl,
optionally substituted $C_1$–$C_{10}$ alkoxycarbonyl,
optionally substituted $C_6$–$C_{15}$ aryloxycarbonyl,
optionally substituted $C_1$–$C_{15}$ heteroaromatic thiocarbonyl having at least one hetero atom selected from the group consisting of nitrogen, oxygen, and sulfur atoms,
optionally substituted $C_2$–$C_{15}$ saturated heterocyclic thiocarbonyl having at least one hetero atom selected from the group consisting of nitrogen, oxygen, and sulfur atoms, or
optionally substituted N—$C_1$–$C_{10}$ alkylthiocarbamoyl; and
$R^3$ represents
a hydrogen atom,
a hydroxyl group,
optionally substituted $C_1$–$C_{10}$ alkyloxy,
optionally substituted $C_1$–$C_{10}$ alkylcarbonyloxy,
optionally substituted $C_1$–$C_{10}$ alkylthio, or
optionally substituted $C_6$–$C_{15}$ arylthio.

3. The compound or pharmaceutically acceptable salt thereof according to claim 1, wherein
$R^1$ represents
$C_1$–$C_{10}$ alkyl or
$C_7$–$C_{15}$ aralkyl optionally substituted by $C_1$–$C_6$ alkoxy;
$R^2$ represents a hydrogen atom,
$C_1$–$C_{10}$ alkylcarbonyl,
$C_3$–$C_{15}$ cycloalkylcarbonyl,
$C_6$–$C_{15}$ aromatic acyl optionally substituted by $C_1$–$C_6$ alkoxy or nitro,
$C_2$–$C_{15}$ heteroaromatic acyl having at least one hetero atom selected from the group consisting of nitrogen, oxygen, and sulfur atoms,
$C_3$–$C_{15}$ saturated heterocyclic acyl, having at least one hetero atom selected from the group consisting of nitrogen, oxygen, and sulfur atoms, optionally substituted by $C_1$–$C_6$ alkyl or $C_1$–$C_6$ alkoxy-$C_1$–$C_6$ alkyl,
$C_1$–$C_{10}$ alkyl optionally substituted by $C_3$–$C_{15}$ cycloalkyl or hydroxyl,
$C_2$–$C_{10}$ alkenyl optionally substituted by phenyl,
$C_7$–$C_{15}$ aralkyl optionally substituted by $C_1$–$C_6$ alkoxy, carbamoyl,
N—$C_1$–$C_{10}$ alkylcarbamoyl with hydrogen atom(s) in the alkyl being optionally substituted by a hydroxyl group,
N—$C_6$–$C_{15}$ aromatic carbamoyl,
N—$C_7$–$C_{15}$ aralkylcarbamoyl,
N,N-di-$C_1$–$C_{10}$ alkylaminocarbonyl,
N—$C_3$–$C_{10}$ cycloalkylcarbamoyl,
$C_1$–$C_{10}$ alkoxycarbonyl,
$C_6$–$C_{15}$ aryloxycarbonyl,
$C_1$–$C_{15}$ heteroaromatic thiocarbonyl having at least one nitrogen atom,
$C_2$–$C_{15}$ saturated heterocyclic thiocarbonyl having at least one nitrogen atom, or
N—$C_1$–$C_{10}$ alkyl-thiocarbamoyl; and
$R^3$ represents
a hydrogen atom,
a hydroxyl group,
$C_1$–$C_{10}$ alkyloxy optionally substituted by $C_3$–$C_{10}$ cycloalkyl,
$C_1$–$C_{10}$ alkylcarbonyloxy,
$C_1$–$C_{10}$ alkylthio, or
$C_6$–$C_{15}$ arylthio.

4. The compound or pharmaceutically acceptable salt thereof according to claim 1, wherein
$R^1$ represents
$C_1$–$C_6$ alkyl or
benzyl optionally substituted by $C_1$–$C_6$ alkoxy;
$R^2$ represents
a hydrogen atom,
$C_1$–$C_6$ alkylcarbonyl,
$C_3$–$C_7$ cycloalkylcarbonyl,
benzoyl optionally substituted by $C_1$–$C_6$ alkoxy or nitro,
five- or six-membered heteroaromatic acyl having one or two nitrogen, oxygen, or sulfur atoms,
five- or six-membered heteroaromatic acyl having nitrogen and sulfur atoms,
five- or six-membered saturated heterocyclic acyl having a oxygen or sulfur atom,
$C_1$–$C_6$ alkyl optionally substituted by $C_3$–$C_7$ cycloalkyl or hydroxy,
$C_2$–$C_6$ alkenyl optionally substituted by phenyl,
benzyl optionally substituted by $C_1$–$C_6$ alkoxy, carbamoyl,
N—$C_1$–$C_6$ alkylcarbamoyl with hydrogen atom(s) in the alkyl being optionally substituted by a hydroxyl group,
N-phenylcarbamoyl,
N-benzylcarbamoyl,
N,N-di-$C_1$–$C_6$ alkylaminocarbonyl,
N—$C_3$–$C_7$ cycloalkylcarbamoyl,
$C_1$–$C_6$ alkoxycarbonyl,
phenyloxycarbonyl,
pyrimidylthiocarbonyl,
pyrrolidylthiocarbonyl, or
N—$C_1$–$C_6$ alkyl-thiocarbamoyl; and
$R^3$ represents
a hydrogen atom,
a hydroxyl group,
$C_1$–$C_6$ alkyloxy optionally substituted by $C_3$–$C_7$ cycloalkyl,
$C_1$–$C_6$ alkylcarbonyloxy,
$C_1$–$C_6$ alkylthio, or
phenylthio.

5. A pharmaceutical composition comprising as an active ingredient the compound according to any one of claims 1 to 4.

6. The pharmaceutical composition according to claim 5, which is a therapeutic or prophylactic agent for progesterone-related diseases, or an abortifacient or a contraceptive.

7. The pharmaceutical composition according to claim 5, which is a carcinostatic agent for breast cancer or ovarian cancer, a therapeutic agent for hysteromyoma, endometriosis, meningioma, or myeloma, a therapeutic or prophylactic agent for osteoporosis or climacteric disturbance, an abortifacient, or an oral contraceptive pill.

8. A method for treating or preventing progesterone-related diseases, for having an abortion, or for orally preventing conception, wherein the compound according to any one of claims 1 to 4 is administered to a mammal including a human being.

9. A method for treating or preventing breast cancer, ovarian cancer, hysteromyoma, endometriosis, meningioma, myeloma, osteoporosis, or climacteric disturbance, for having an abortion, or for orally preventing conception, wherein the compound according to any one of claims 1 to 4 is administered to a mammal including a human being.

10. A compound represented by the following formula (II) or a pharmaceutically acceptable salt thereof:

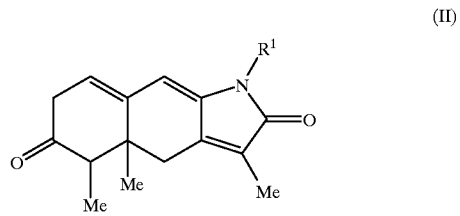

(II)

wherein
$R^1$ represents
a hydrogen atom,
optionally substituted $C_1$–$C_{10}$ alkyl,
optionally substituted $C_2$–$C_{10}$ alkenyl,
optionally substituted $C_2$–$C_{10}$ alkynyl,
optionally substituted $C_3$–$C_{10}$ cycloalkyl, or
optionally substituted $C_7$–$C_{15}$ aralkyl.

* * * * *